United States Patent [19]

Gausing et al.

[11] Patent Number: 5,789,657
[45] Date of Patent: Aug. 4, 1998

[54] POTATO α-AMYLASE GENES

[76] Inventors: Kirsten Gausing, Studstrupvej 9, DK-8541 Skødstrup; Jette D. Kreiberg, Silkeborgvej 698, DK-8220, Brabrand, both of Denmark

[21] Appl. No.: 455,691

[22] Filed: May 31, 1995

Related U.S. Application Data

[62] Division of Ser. No. 131,931, Oct. 5, 1993, Pat. No. 5,498,832, which is a continuation of Ser. No. 651,408, filed as PCT/DK90/00108, Apr. 24, 1990, published as WO90/12876, Nov. 1, 1990, abandoned.

[30] Foreign Application Priority Data

Apr. 24, 1989 [DK] Denmark ................................. 1980/89

[51] Int. Cl.$^6$ .......................... A01H 5/00; C12N 15/63; C12N 15/82; C12N 15/56
[52] U.S. Cl. ........................ 800/205; 800/DIG. 40; 800/DIG. 42; 435/6; 435/91.1; 435/91.4; 435/172.1; 435/172.3; 435/204; 435/252.2; 435/252.3; 435/320.1; 435/375; 536/24.5
[58] Field of Search ................ 800/205, 250, 800/DIG. 42, 255, DIG. 40; 536/24.3, 24.33, 24.5; 435/6, 91.1, 91.4, 172.3, 204, 240.4, 320.1, 375, 252.2, 252.3, 172.1; 935/3, 5, 8, 10, 22, 24, 35, 44, 67, 77, 78

[56] References Cited

U.S. PATENT DOCUMENTS

| | | | |
|---|---|---|---|
| 4,736,866 | 4/1988 | Leder et al. | 800/1 |
| 4,769,327 | 9/1988 | Stephens et al. | 435/68 |
| 4,771,002 | 9/1988 | Gelvin | 435/172.3 |
| 4,794,175 | 12/1988 | Nonberg et al. | 536/27 |
| 5,498,832 | 3/1996 | Gausing et al. | 800/205 |

OTHER PUBLICATIONS

Shaffer et al., Plant Physiol. 87: 431–436 (1988).
Mohapatra et al., Plant Physiol. 89: 375–380 (1989).
Kurkela et al., Plant Cell Reports 7: 495–498 (1988).
Mignery et al., Nucleic Acids Research 12(21): 7987–8000 (1984).
Teeri et al., The EMBO Journal 5(8): 1755–1760 (1986).
W. James Antiviral Chem. & Chemotheraphy (1991) 2(4):191–214.
J. Wetmur Crit. Rev. in Biochem. & Mol. Biol. ('91) 26(3) 227–59.
A. van der Krol Biotechniques ('88) 6(10) 958–76.
Khursheed et al., "Barley Alpha–Amylase Genes. Quantitative Comparison Of . . . ", *Journal of Biological Chemistry*, vol. 263, No.35, pp. 18953–18960, (1988).
Chandler, P. et al., Chemical Abstracts, vol. 102, (1985), Abstract No. 18778u.
Gatenby et al., "Expression Of A Wheat Alpha–Amylase Gene in Escherichia Coli: Recognition of The Translational Initiation Site. . .", *Gene*, vol. 45., No. 1, pp. 11–18, (1986).
Fan, M.L., Chemical Abstracts, vol. 83, (1975), Abstract No. 39317x.

J.C. Rogers, "RNA Complementary To Alpha–Amalyse mRNA In Barley", *Plant Molecular Biology*, vol. 11:125–138, (1988).
Huttly et al., "GA Regulated Expression From A Wheat Alpha–Amylase Promoter In Oat Aleurone . . . ", *Journal of Cellular Biochemistry*, Supp. 12C, pp. 207, Abstract No. L600, (1988).
J. Rogers, Chemical Abstracts, vol. 102, (1985), Abstract No. 200280c.
J.C. Rodgers et al., "Isolation And Sequence Analysis Of A Barely α–Amylase cDNA Clone*", *Journal of Biological Chemistry*, vol. 258, No. 13, (1983), pp. 8169–8174.
M.L. Fan, "Purification And Properties Of Potato Alpha–Amylase", *Taiwania*, vol. 20, No. 1, pp. 71–76, (1975).
Knox et al., "Structure And Organization of Two Divergent α–Amylase Genes From Barley", *Plant Molecular Biology*, vol. 9:3–17, (1987).
Huang et al., "Expression And Regulation Of α–Amylase Gene Family in Barley Aleurones", *Journal of Molecular And Applied Genetics*, vol. 2:579–588, (1984).
Whittier et al., "Nucleotide Sequence analysis Of α–Amylase And Thiol Protease Genes That Are Hormonally Regulated In Barley Aleurone Cells", *Nucleic Acids Research*, vol. 15(6):2515–2535, (1987).
Baulcombe et al., "A Novel Wheat α–Amylase Gene (α–Amy3)", *Mol. Gen. Genet.*, vol.209:33–40, (1987).
Rogers, "Two Barley α–Amylase Gene Families Are Regulated Differently In Aleurone Cells", *The Journal of Biological Chemistry*, vol. 260(6):3731–3738, (1985).
Miller et al., "Potato", in *Handbook of Plant Cell Culture*, vol. 3, (NY, MacMillan, 1984), pp.291–326.
Nickell, "Proteins", in *Plant Tissue Culture As A Source of Biochemicals*, (Bora Raton, FL., CRC Press, 1980), pp. 235–245.
Watson et al., *Molecular Biology Of The Gene*, 4th f.d. Monto Part, CA, Benjamin/Cummings, 1987, pp.231, 233, 574–575, 703–704 and 716.
Salanavbat et al., *Gene*, vol. 60:47–56, (1987).

(List continued on next page.)

*Primary Examiner*—Charles C. P. Rories
*Attorney, Agent, or Firm*—Foley & Lardner

[57] ABSTRACT

α-Amylase, an enzyme that hydrolyzes starch, can be found in all plants. The modification of potato starch production, in particular, is important in the preparation of various food products. The present invention pertains to expression vectors for producing antisense α-amylase RNA which is complementary to, or which hybridizes specifically to, potato α-amylase mRNA. This invention also includes a vector system which operates to introduce into the genome of a plant an expression vector for producing antisense α-amylase RNA, and a microorganism of the genus Agrobacterium which contains such a vector system and which is capable of infecting a plant. This invention also provides a genetically modified plant containing in its genome an expression vector for producing antisense α-amylase RNA.

25 Claims, 36 Drawing Sheets

OTHER PUBLICATIONS

Salinas et al., *Nucleic Acids Research*, vol. 16:4261–4285, (1988).

Wenzler et al., *Plant Molecular Biology*, vol. 12:41–40, (1989).

Pikaard et al., *Nucleic Acids Research*, vol. 14:5564–5566, (1986).

Manatis et al., *Molecular Cloning*, Coldspring Harbor, NY, CSH Press, (1982) pp. 248.250–251, 309–401, 504–506.

Grant, *Hackh's Chemical Dictionary*, 4th Ed., N.Y., McGraw Hill, (1969), p.44.

Derynck et al., *Cell*, vol. 38, (1984), pp. 287–297.

Rogers et al., *J. Biological Chemistry*, vol. 259, (1984), pp. 12234–12240.

Lewin, R., *Science*, vol. 237, (1987)

Kay et al., *Science*, Voo. 236, pp. 1299–1302, (1987).

Rogers, *Biochem. Biophys. Res. Comm.*, vol. 128, pp. 470–476, (1985).

Beltz et al., *Meth. in Enzymol*, vol.100, pp. 266–274 (1983).

Rychlik et al., *Nucleic Acids Research*, vol. 18, No.21 pp. 6409–6412, (1990).

Lowe et al., *Nucl. Acids Res.*, vol. 18, No 7, pp. 1757–1761, (1990).

Sambrook et al., "Molecular Cloning", *A Lab. Manual*, 2nd Ed. CSH Lab. Press, CSH NY, pp 11.45–11.46, (1989).

Gerherdt et al., *Plant Physiology*, vol. 83, pp. 399–407, (1987).

Rogers, *J. Biol. Chem.*, vol. 258, No. 13, pp. 8169–8174, (1983).

Salanoubat et al., *Gene*, vol. 60, pp. 47–56, (1987).

Sambrook et al., "Molecular Cloning, A Lab. Manual", CSHL Press, (1989), CSH, NY, pp. 9.50–9.51, 11.2–11.19, 11.45–1161.

Aebersold et al., PNAS, vol. 84, (Oct. 1987), pp. 6970–6974.

Taiwania, vol. 20, No. 1, (Feb. 1975), pp. 71–76.

FIG. 1A

Amyz3/4

```
  1  CGA CAG TCG CCG TCA CCG CCA CAC TAT TCT CGA CGC GTC GTC   48
 49  TAT CTC CTC CAC CCC ACA GCC GTC AAT TCC AAG CTT CCA ATG AAC CGT   96
 97  TGC CAT GTG TCA CTG CCT ATT CAC CGC GAA ACA TGA ATA TCA CTG ACG  144
145  AAC GAT TTC GGA GCG GAA CGA ATC CAG AAA ATG GAT TAC TTT CTA TAA  192
193  ATT CCT CGA ATC TCA ACT CCA TTT CGT AAA AAT AAA ATT AAA AAT ATT  240
241  GTT TCT TTT TTG ATT TCT GGT TTA TGT GGT GAT CGA ATT TTC AAT TTT  288
289  TTT ACT GGT AGT GAT TCC TAC TTT TCT TCA ATT CGA TTT CTC CTT TTT  336
337  CCA TTT CAC GGT TGA GAA TTC ATG ATT CCT TAT CAG AGG AAT CGA TCC  384
385  GAT TTG ACT AAT TTC ACT TTT CGT CTG TAT AAA TAC CAG AGT ATC TAG  432
433  GTT GAG GAA CGT AAT TTC AAG CTG CGA TCG GCT TTT TCC CCT GAA CGA  480
481  GCA AAC ACA GGT TGT GGG TTC GAG TTA GCA AGG GAC GTA TAA TCT CAA  528
529  CTA CAA TCC ATT ATG GCG CTT GAT GAA AGT CAG CAG TCT GAT CCA TTG  576
  1                          M   A   L   D   E   S   Q   Q   S   D   P   L   12
```

FIG. 1B

| | | | | | | | | | | | | | | | | |
|---|---|---|---|---|---|---|---|---|---|---|---|---|---|---|---|---|
| 577 | GTT | GTG | ATA | CGC | AAT | GGA | AAG | GAG | ATC | ATA | TTG | CAG | GCA | TTC | GAC | TGG | 624 |
| 13 | V | V | I | R | N | G | K | E | I | I | L | Q | A | F | D | W | 28 |
| 625 | GAA | TCT | CAT | AAA | CAT | GAT | TGG | TGG | CTA | AAT | TTA | GAT | ACG | AAA | GTT | CCT | 672 |
| 29 | E | S | H | K | H | D | W | W | L | N | L | D | T | K | V | P | 44 |
| 673 | GAT | ATT | GCA | AAG | TCT | GGT | TTC | ACA | ACT | GCT | CTG | CCT | CCG | GTG | TGT | 720 |
| 45 | D | I | A | K | S | G | F | T | T | A | L | P | P | V | C | 60 |
| 721 | CAG | TCA | TTG | GCT | CCT | GAA | GGT | TAC | CTT | CCA | CAG | AAC | CTT | TAT | TCT | CTC | 768 |
| 61 | Q | S | L | A | P | E | G | Y | L | P | Q | N | L | Y | S | L | 76 |
| 769 | AAT | TCT | AAA | TAT | GGT | TCT | GAG | GAT | CTC | TTA | AAA | GCT | ATA | GTC | ATT | AAC | AAG | 816 |
| 77 | N | S | K | Y | G | S | E | D | L | L | K | A | I | V | I | N | K | 92 |
| 817 | ATG | AAG | CAG | TAC | AAA | ACT | GTT | AGA | GCG | ATG | GAC | TAC | AAC | CGC | TAT | GAT | 864 |
| 93 | M | K | Q | Y | K | T | V | R | A | M | D | Y | N | R | Y | D | 108 |
| 865 | CGT | GTT | GGG | ACT | ACT | CAA | GGG | CAT | GAA | CAT | GCT | ATT | TGC | ACT | GGT | 912 |
| 109 | R | V | G | T | T | Q | G | H | E | H | A | I | C | T | G | 124 |
| 913 | GGA | ATT | CCT | ATG | TCT | TGG | GAT | GAA | ATG | GGA | GAT | GTT | CCA | AAT | 960 |
| 125 | G | I | P | M | S | W | D | E | M | G | D | V | P | N | 140 |
| 961 | GGA | AGG | GGT | AAC | AAA | AGC | ACT | GGA | GAC | AAC | TTT | AAT | GGA | GTT | CCA | AAT | 1008 |
| 141 | G | R | G | N | K | S | T | G | D | N | F | N | G | V | P | N | 156 |
| 1009 | ATA | GAT | CAT | ACA | CAA | TCC | TTT | GTT | CGG | AAA | GAT | CTC | ATT | GAC | TGG | ATG | 1056 |
| 157 | I | D | H | T | Q | S | F | V | R | K | D | L | I | D | W | M | 172 |

FIG. IC

```
AmyZ3/4
1057 CGG TGG CTA AGA TCC TCT GTT GGC TTC CAA GAT TTT CGT TTT GAT TTT 1104
 173  R   W   L   R   S   S   V   G   F   Q   D   F   R   F   D   F   188
1105 GCC AAA GGT TAT GCT TCA AAG TAT GTA AAG GAA TAT ATC GAG GGA GCT 1152
 189  A   K   G   Y   A   S   K   Y   V   K   E   Y   I   E   G   A   204
1153 GAG CCA ATA TTT GCA GTT GGA GAA TAC TGG GAC ACT TGC AAT TAC AAG 1200
 205  E   P   I   F   A   V   G   E   Y   W   D   T   C   N   Y   K   220
1201 GGC AGC AAT AAT GCA TAC TAT GAT CAA AAC CAA GAT AGT CAC AGG ATC ATC 1248
 221  G   S   N   L   D   Y   N   Q   D   S   H   R   I   I   236
1249 AAT TGG ATT GAT GGC GCG GGA CAA CTT TCA ACT GCA TTC GAT TTT ACA 1296
 237  N   W   I   D   G   A   G   Q   L   S   T   A   F   D   F   T   252
1297 ACA AAA GCA GTC CTT CAG GAA GCA GTC AAA GGA GAA TTC TGG AGG TTG 1344
 253  T   K   A   V   L   Q   E   A   V   K   G   E   F   W   R   L   268
1345 CGT GAC TCT AAG GGG AAG GGG CCA CCC CAG GTT TTA GGA TTG TGG CCT TCA 1392
 269  R   D   S   K   G   K   P   P   G   V   L   W   P   S   284
1393 AGG GCT GTC ACT TTT ATT GAT AAT CAC GAC ACT GGA TCA ACT CAG GCG 1440
 285  R   A   V   T   F   I   D   N   H   D   T   G   S   T   Q   A   300
1441 CAT TGG CCT TTC CCT TCA CGT CAT GTT ATG GAG GGC TAT GCA TAC ATT 1488
 301  H   W   P   F   P   S   R   H   V   M   E   G   Y   A   Y   I   316
```

FIG. ID

```
1489  CTT ACA CAC CCA GGG ATA CCA TCA GTT TTC TTT GAC CAT TTC TAC GAA  1536
317   L   T   H   P   G   I   P   S   V   F   F   D   H   F   Y   E    332

1537  TGG GAT AAT TCC ATG CAT GAC CAA ATT GTA AAG CTG CTT GCT ATT CGG  1584
333   W   D   N   S   M   H   D   Q   I   V   K   L   L   A   I   R    348

1585  AGG AAT CAA GGC ATA CAC AGC CGT TCA TCT ATA AGA ATT CTT GAG GCA  1632
349   R   N   Q   G   I   H   S   R   S   S   I   R   I   L   E   A    364

1633  CAG CCA AAC TTA TAC GCT GCA ACC ATT GAT GAA AAG GTT AGC GTG AAG  1680
365   Q   P   N   L   Y   A   A   T   I   D   E   K   V   S   V   K    380

1681  ATT GGG GAC GGA TCA TGG AGC CCT GCT GGG AAA GAG TGG AAG CTC GCG  1728
381   I   G   D   G   S   W   S   P   A   G   K   E   W   K   L   A    396

1729  ACC AGT GGC CAT CGC TAT GCA GTC TGG CAG AAG TAA TCT TAC AGC TAT  1776
397   T   S   G   H   R   Y   A   V   W   Q   K   *                    407

1777  TCC GTT ACT TAA TAT ATT AGT AGA AAT ATA TGT TTA AAC CCG AGC
1825  ACC TAC TTC TAA CAC TAG ATC CGC CTC TAC AGG CTT GGA TGG AGT GAT
1873  GAG TTT TTT CCT GTT CAT TAG ACA TTG CAA CAT GGG ATG TAT GTT
1921  TTG TTA ATA AAA GTG TTC TTG ATC AAT GCA ATG TAA TAA GGG           1962
```

FIG. 2A

```
Amy27
    1   G GCG CTT GAT GAA AGT CAG CAG TCT GAT CCA TTG GTT GTG ATA CGC        46
    1     A   L   D   E   S   Q   Q   S   D   P   L   V   V   I   R         15

47   AAT GGA AAG GAG ATC ATA TTG CAG GCA TTC GAC TGG GAA TCT CAT AAA      94
   16    N   G   K   E   I   I   L   Q   A   F   D   W   E   S   H   K      31

95   CAT GAT TGG TGG ATA AAT TTA GAT ACG AAA GTT CCT GAT ATT GCA AAG     142
   32    H   D   W   W   I   N   L   D   T   K   V   P   D   I   A   K      47

143   TCT GGT TTC ACA ACT GCT TGG CTG CCT CCG GTG TGT CAG TCA TTG GCT     190
   48    S   G   F   T   T   A   W   L   P   P   V   C   Q   S   L   A      63

191   CCT GAA GGT TAC CTT CCA CAG AAC CTT TAT TCT CTC AAT TCT AAA TAT     238
   64    P   E   G   Y   L   P   Q   N   L   Y   S   L   N   S   K   Y      79

239   GGT TCT GAG GAT CTC TTA AAA GCT TTA CTT AAT AAG ATG AAG CAG TAC     286
   80    G   S   E   D   L   L   K   A   L   L   N   K   M   K   Q   Y      95

287   AAA GTT AGA GCG ATG GCG GAC ATA GTC ATT AAC CAT CGT GTT GGG ACT     334
   96    K   V   R   A   M   A   D   I   V   I   N   H   R   V   G   T     111

335   ACT CAA GGG CAT GGT ATG TAC AAC CGC TAT GAT GGA ATT CCT ATG         382
  112    T   Q   G   H   G   M   Y   N   R   Y   D   G   I   P   M         127

383   TCT TGG GAT GAA CAT GCT ATT ACA TCT TGC ACT GGT GGA AGG GGT AAC     430
  128    S   W   D   E   H   A   I   T   S   C   T   G   G   R   G   N     143
```

FIG. 2B

```
431  AAA AGC ACT GGA GAC AAC TTT AAT GGA GTT CCA AAT ATA GAT CAT ACA  478
144   K   S   T   G   D   N   F   N   G   V   P   N   I   D   H   T  159

479  CAA TCC TTT GTC CGG AAA GAT CTC ATT GAC TGG ATG CGG TGG CTA AGA  526
160   Q   S   F   V   R   K   D   L   I   D   W   M   R   W   L   R  175

527  TCC TCT GTT GGC TTC CAA GAT TTT CGT TTT GAT TTT GCC AAA GGT TAT  574
176   S   S   V   G   F   Q   D   F   R   F   D   F   A   K   G   Y  191

575  GCT TCA AAG TAT GTA AAG GAA TAT ATC GAG GGA GCT TTT CCA ATA TTT  622
192   A   S   K   Y   V   K   E   Y   I   E   G   A   F   P   I   F  207

623  GCA GTT GGA GAA TAC TGG GAC ACT TGC AAT TAC AAG GGC AGC CCA GAG  670
208   A   V   G   E   Y   W   D   T   C   N   Y   K   G   S   P   E  223

671  GAT TAC AAC CAA GAT AGT CAC AGG CAA TTC GCA ACT AAA ATC AAT TGG  718
224   D   Y   N   Q   D   S   H   R   Q   F   A   T   K   I   N   W  239

719  GGC GCG GGA GAA TTC TGG CGT TTG CGT GAC TTC GAT TTT ACA AAA ATT  766
240   G   A   G   E   F   W   R   L   R   D   F   D   F   T   K   I  255

767  CTT CAG GAA GAA GGA TTC TGG CGT TTG CGT GAC TCT AAG GCA GTC ACT  814
256   L   Q   E   E   G   F   W   R   L   R   D   S   K   A   V   T  271

815  GGG AAG CCA CCA GGA GTT TTA GGA TGG TGG CCT TCA AGG GCT GTC ACT  862
272   G   K   P   P   G   V   L   G   W   W   P   S   R   A   V   T  287
```

FIG. 2C

| Pos | | | | | | | | | | | | | | | | | | End |
|---|---|---|---|---|---|---|---|---|---|---|---|---|---|---|---|---|---|---|
| 863 / 288 | TTT F | ATT I | GAT D | AAT N | CAC H | GAC D | ACT T | GGA G | TCA S | ACT T | CAG Q | GCG A | CAT H | TGG W | CCT P | TTC F | | 910 / 303 |
| 911 / 304 | CCT P | TCA S | CGT R | CAT H | GTT V | CAT H | ATG M | GAG E | GGC G | TAT Y | ATT I | CTT L | ACA T | CAC H | CCA P | | | 958 / 319 |
| 959 / 320 | GGG G | ATA I | CCA P | TCA S | GTT V | TTC F | TAT Y | GAC D | CAT H | TAC Y | GAA E | ATT I | TGG W | GAT D | AAT N | TCC S | | 1006 / 335 |
| 1007 / 336 | ATG M | CAT H | GAC D | CAA Q | ATT I | GTA V | AAG K | CTG L | ATT I | GCT A | ATT I | CGG R | AGG R | AAT N | CAA Q | GGC G | | 1054 / 351 |
| 1055 / 352 | ATA I | CAC H | AGC S | CGT R | TCA S | TCT S | ATA I | AGG R | ATT I | CTT L | GAG E | GCA A | CAG Q | CCA P | AAC N | TTA L | | 1102 / 367 |
| 1103 / 368 | TAC Y | GCT A | GCA A | ACC T | ATT I | GAT D | GAA E | AAG K | GTT V | AGC S | ATG M | AAG K | ATT I | GGG G | GAC D | GGA G | | 1150 / 383 |
| 1151 / 384 | TCA S | TGG W | AGC S | CCT P | GCT A | GGG G | AAA K | GAG E | TGA * | ACT T | CTC L | GCG A | TAT Y | TCC S | GTT V | ACT T | TAA * | 1198 / 399 |
| 1199 / 400 | CGC R | TAT Y | GCA A | GTC V | TGG W | CAG Q | AAG K | TGA * | TCT S | TAC Y | AGC S | TAT Y | TCC S | GTT V | ACT T | TAA * | | 1246 / 406 |
| 1247 | TAT | ATT | AGT | AGA | AAT | ATA | GTT | TTA | AAC | CCG | AGC | ACC | TAC | TTC | TAA | | | 1294 |
| 1295 | TAC | TAG | ATC | CGC | CTC | TAC | AGG | CTT | GGA | TGG | AGT | GAT | GAG | TTT | TTT | | | 1342 |
| 1343 | TCT | GTT | CAT | TAG | ACA | TTG | CAA | CAT | GGG | ATG | TAG | TTT | TGG | TAA | AAG | | | 1390 |
| 1391 | TGT | TCT | TGA | TCA | ATG | CAA | AAA | AAA | A | | | | | | | | | 1415 |

FIG. 3A

```
Amy21
     1  TC  TGA TCA GTT TTC AGT TCC AGG AAC GAT TCC AAG TTT GGG AAT CAG    47
     1                S   V   F   S   S   R   N   D   S   K   F   G   N   Q   15

48  CAA CAA CTG AAA ACT CTT ATT AAG AAG GCT TTA CAT GAC CAC GGG ATC AAA    95
    16   Q   Q   L   K   T   L   I   K   K   A   L   H   D   H   G   I   K    31

96  TCG GTT GCT GAT ATA GTG ATA AAT CAT AGA ACT GCT GAT AAA AAA GAT   143
    32   S   V   A   D   I   V   I   N   H   R   T   A   D   N   K   D    47

144  AGC AGG ATA TAC AGC ATC TTT GAA GGA GGA ACG TCT GAT GAC CGG   191
    48   S   R   I   Y   S   I   F   E   G   G   T   S   D   D   R    63

192  CTT GAT TGG GGT CCA TCT TTC ATT TGC AAG AAC GAC ACA CAA TAT TCT   239
    64   L   D   W   G   P   S   F   I   C   K   N   D   T   Q   Y   S    79

240  GAT GGC ACA GGG AAT CCA GAC ACG GGT TTG GAC TTT GAA CCT GCC CCT   287
    80   D   G   T   G   N   P   D   T   G   L   D   F   E   P   A   P    95

288  GAT ATC GAT CAT CTT AAT ACA AGA GTG CAG AAA GAG TTA TCA GAC TGG   335
    96   D   I   D   H   L   N   T   R   V   Q   K   E   L   S   D   W   111

336  ATG AAT TGG CTG AAA TCT GAA ATT GGA TTT GAT GGT TGG CGT TTC GAT   383
   112   M   N   W   L   K   S   E   I   G   F   D   G   W   R   F   D   127

384  TTT GTT AGG GGA TAT GCA CCT TGC ATT ACC AAG ATT TAT ATG AGA AAC   431
   128   F   V   R   G   Y   A   P   C   I   T   K   I   Y   M   R   N   143
```

FIG. 3B

| | | | | | | | | | | | | | | | |
|---|---|---|---|---|---|---|---|---|---|---|---|---|---|---|---|
| 432 | ACA | TCC | CCG | GAT | TTT | GCA | GTT | GGT | GAA | TTT | TGG | AAC | TCT | CTT | GCT | TAT | 479 |
| 144 | T | S | P | D | F | A | V | G | E | F | W | N | S | L | A | Y | 159 |
| 480 | GGC | CAG | GAT | GGG | AAA | CCG | GAA | TAT | AAC | CAG | GAC | AAT | CAT | AGG | AAT | GAG | 527 |
| 160 | G | Q | D | G | K | P | E | Y | N | Q | D | N | H | R | N | E | 175 |
| 528 | CTA | GTT | GGT | TGG | GTT | AAA | AAT | GCA | GGG | CGG | GCT | GTA | ACA | GCC | TTT | GAT | 575 |
| 176 | L | V | G | W | V | K | N | A | G | R | A | V | T | A | F | D | 191 |
| 576 | TTT | ACA | ACT | AAG | GAT | CCC | CAA | ATT | CTT | CAA | GTT | CAA | GGA | GAG | TTA | TGG | 623 |
| 192 | F | T | T | K | D | P | Q | I | L | Q | V | Q | G | E | L | W | 207 |
| 624 | AGA | TTG | AAG | GAT | CCC | AAT | GGA | AAA | CCT | CCT | ATG | ATA | GGT | GTT | TTG | 671 |
| 208 | R | L | K | D | P | N | G | K | P | P | M | I | G | V | L | 223 |
| 672 | CCT | CGA | AAA | GCT | GTG | ACT | TTT | ATC | GAT | AAT | CAT | GAT | ACT | GGA | TCG | ACA | 719 |
| 224 | P | R | K | A | V | T | F | I | D | N | H | D | T | G | S | T | 239 |
| 720 | CAA | AAT | ATG | TGG | CCT | TTC | CCT | TCA | GAC | AAA | GTT | ATG | CAA | GGA | TAT | GCA | 767 |
| 240 | Q | N | M | W | P | F | P | S | D | K | V | M | Q | G | Y | A | 255 |
| 768 | TAC | ATT | CTA | ACT | CAT | CCA | GGA | ATC | CCA | TCA | GTG | TTT | TAT | GAC | CAT | TTC | 815 |
| 256 | Y | I | L | T | H | P | G | I | P | S | V | F | Y | D | H | F | 271 |
| 816 | TTT | GAT | TGG | GGC | TTC | ATG | GAT | GGA | ATT | TCA | GCA | CTA | ATC | TCT | ATT | AGG | 863 |
| 272 | F | D | W | G | F | M | D | G | I | S | A | L | I | S | I | R | 287 |

FIG. 3C

```
Amy21
 864 AAG AGG AAT AGG ATT TGT GCA ACA AGC AAT GTG CAA ATA ATG GCT TCT  911
 288  K   R   N   R   I   C   A   T   S   N   V   Q   I   M   A   S   303

912 GAT TCA GAT CTT TAT ATA GCA ATG ATT CAT CAC AAA ATT GTC AAG        959
 304  D   S   D   L   Y   I   A   M   I   H   H   K   I   V   K        319

960 ATT GGG CCA AAA CTT GAT CTT GGA AAT CTT ATT CCA CCT AAT TAT GAG  1007
 320  I   G   P   K   L   D   L   G   N   L   I   P   P   N   Y   E   335

1008 GTG GCA ACT TCT GGA CAA GAC TAT GCT GTA TGG GAG CAA AAG GCA TAA  1055
 336  V   A   T   S   G   Q   D   Y   A   V   W   E   Q   K   A   *   350

1056 TCA TAT TGT AGT ACC ATT TAT TTA CCA CAC TAA AAG TGA CCA TGG ACA  1103

1104 AAA TGG TTC TTA GTG TTA ATG TTA TAT GAT TGA AAA TGT AAT TTA TAT  1151

1152 CGG CAT AAT GAA GGC CAA AAA TTC AAG AAA TTA TAT TCA ATT CGA TAG  1199

1200 ACC TTG CTC AAT TCA C                                             1215
```

FIG. 4A

```
Amy26
   1    GT  CCG TCT TTA ATT TGC AAG GAT GAC ACA CAA TAT TCT GAT GGC ACG    47
   1        P   S   L   I   C   K   D   D   T   Q   Y   S   D   G   T     15

48    GGG AAT CTA GAC ACG GGT TTG GAC TTT GAA CCT GCC CCT GAT ATT GAT    95
  16     G   N   L   D   T   G   L   D   F   E   P   A   P   D   I   D    31

96    CAT CTT AAT ATC AGA GTG CAG AAA GAG TTA TCA GAT TGG ATG AAT TGG   143
  32     H   L   N   I   R   V   Q   K   E   L   S   D   W   M   N   W    47

144    CTC AAG TCT GAA ATT GGA TTT GAT CGT ATG TCA GTT CGT TTT GTT AGG   191
  48     L   K   S   E   I   G   F   D   R   M   S   V   R   F   V   R    63

192    GGA TAT GCA CCT AGC ATC ACC AAG ATT TAT ATG GGA AAC ACG TCC CCG   239
  64     G   Y   A   P   S   I   T   K   I   Y   M   G   N   T   S   P    79

240    GAT TTT GCA GTT GAA ATT GGT GAA TTT TGG AAC TCT CTT GCG TAT GGC   287
  80     D   F   A   V   E   I   G   E   F   W   N   S   L   A   Y   G    95

288    GGG AAA CCG TAT AAC CAG GAC AAT CAT AGG AAT GAG CTA TTC ACA CAG   335
  96     G   K   P   Y   N   Q   D   N   H   R   N   E   L   F   T   Q   111

336    TGG GTT CAA AAT GGG GGT GCT GTA AAA GCC TTT GAT TTC AGA TTG GTT   383
 112     W   V   Q   N   G   G   A   V   K   A   F   D   F   R   L   V   127

384    AAG GGA ATT CTT CAA GCT GCA GTT GAA GGA TTA TGG AGA TTG AAG ACT   431
 128     K   G   I   L   Q   A   A   V   E   G   L   W   R   L   K   T   143
```

FIG. 4B

| Pos | | | | | | | | | | | Pos |
|---|---|---|---|---|---|---|---|---|---|---|---|
| 432 | GAT | TCC | AAT | GGA | AAA | CCT | CCT | GGG | ATG | ATA | 479 |
| 144 | D | S | N | G | K | P | P | G | M | I | 159 |
| | GGT | GTT | TTG | CCT | CAA | AAT | | | | | |
| | G | V | L | P | Q | N | | | | | |
| 480 | GCT | GTG | ACT | TTT | ATC | GAT | CAC | AAT | CAC | AAT | 527 |
| 160 | A | V | T | F | I | D | H | N | H | N | 175 |
| | TCG | ACA | CAA | AAT | ATG | | | | | | |
| | S | T | Q | N | M | | | | | | |
| 528 | TGG | CCT | TTC | CCT | TCA | GAC | AAA | GTT | ATG | CAA | 575 |
| 176 | W | P | F | P | S | D | K | V | M | Q | 191 |
| | GGA | TAT | GCA | TAC | ATT | CTC | | | | | |
| | G | Y | A | Y | I | L | | | | | |
| 576 | ACT | CAT | CCA | GGA | ATT | CCA | TCA | CTG | TTT | TAT | 623 |
| 192 | T | H | P | G | I | P | S | L | F | Y | 207 |
| | CAT | TTC | TTG | ATT | GGG | | | | | | |
| | H | F | L | I | G | | | | | | |
| 624 | GCT | GGA | AGG | ATG | GAA | TTT | CAG | CAC | TAA | TCT | 671 |
| 208 | A | G | R | M | E | F | Q | H | * | S | 215 |
| | CTA | TTA | GGA | AGA | GGA | ATG | | | | | |
| | L | L | G | R | G | M | | | | | |
| 672 | GGA | TTT | GTG | CAA | CAA | GCA | ATG | TGC | AGA | TAA | 719 |
| 720 | TTT | ATA | TAG | CAA | TGA | TTG | ATC | AGA | AAA | TTA | 767 |
| 768 | AAC | TTG | ATC | TTG | GAA | ATC | TTA | TCC | CAC | CTA | 815 |
| 816 | CTG | GAC | AAG | ACT | ATG | ATG | CTG | TAT | GGG | AGC | 863 |
| 864 | CAA | AAT | GTC | ATC | ATG | GAC | CAA | ATG | TCA | GCA | 911 |
| 912 | GTG | TTT | AAT | GTC | ATT | TGA | CTG | AAA | ATG | TAG | 959 |
| 960 | AAT | GAA | GGC | AAA | AAA | TTC | AAG | AAA | TTA | TAT | 1007 |
| 1008 | TG | | | | | | | | | | 1009 |

FIG. 5A

```
Amy22P

1      A TCC TTT GTC CGG AAA GAT CTC ATT GAC TGG ATG CGG TGG CTA AGA    46
  1      A  S   F   V   R   K   D   L   I   D   W   M   R   W   L   R    15

47     TCC TCT GTT GGC TTC CAA GAT TTT CGT TTT GAT TTT GCC AAA GGT TAT    94
 16      S   S   V   G   F   Q   D   F   R   F   D   F   A   K   G   Y    31

95     GCT TCG AAG TAT GTA AAG GAA TAT ATC GAG GGG GCT GAG CCA ATA TTT   142
 32      A   S   K   Y   V   K   E   Y   I   E   G   A   E   P   I   F    47

143     GCA GTT GGA GAA TAC TGG TGG GAC ACT TGC AAT TAC AAG GGC        190
 48      A   V   G   E   Y   W   W   D   T   C   N   Y   K   G           63

191     GAT TAC AAC CAA GAT AGT CAC AGG CAA AGA ATC ATC AAT TGG ATT GAT   238
 64      D   Y   N   Q   D   S   H   R   Q   R   I   I   N   W   I   D    79

239     GGC GCG GGA CAA CTT TCA ACT GCA TTC GAT TTT ACA AAA ACA AAA GCA   286
 80      G   A   G   Q   L   S   T   A   F   D   F   T   K   T   K   A    95

287     CTT CAG GAA GCA GTC AAA GGA GAA TTC TGG CGT TTG CGT GAC TCT AAG   334
 96      L   Q   E   A   V   K   G   E   F   W   R   L   R   D   S   K   111

335     GGG AAG CCA GGA GTT TTA GGA TGG TGG CCT TCA AGG GCA GTC ACT       382
112      G   K   P   G   V   L   G   W   W   P   S   R   A   V   T       127
```

FIG. 5B

```
383  TTT ATT GAT AAT CAC GAC ACT GGA TCA ACT CAG GCG CAT TGG CCT TTC  430
128   F   I   D   N   H   D   T   G   S   T   Q   A   H   W   P   F   143
431  CCT TCA CGT CAT GTT ATG GAG GGC TAT GCA TAC ATT CTT ACA CAC CCA  478
144   P   S   R   H   V   M   E   G   Y   A   Y   I   L   T   H   P   159

479  GGG ATA CCA TCA GTT TTC TAT GAC CAT TTC TAC GAA TGG GAT AAT TCC  526
160   G   I   P   S   V   F   Y   D   H   F   Y   E   W   D   N   S   175

527  ATG CAT GAC CAA ATT GTA AAG CTG ATT GCT ATT CGG AGG AAT CAA GGC  574
176   M   H   D   Q   I   V   K   L   I   A   I   R   R   N   Q   G   191

575  ATA CAC AGC CGT TCA TCT ATA AGG ATT CTT GAG  CA CAG CCA AAC TTA  622
192   I   H   S   R   S   S   I   R   I   L   E       Q   P   N   L   207

623  TAC GCT GCA ACC ATT GAT GAA AAG GTT AGC ATG AAG ATT GGG GAC GGA  670
208   Y   A   A   T   I   D   E   K   V   S   M   K   I   G   D   G   223

671  TCA TGG TGC CCT GCT GGG AAA GAG TGG ACT CTC GCG ACC AGT GGC CAT  718
224   S   W   C   P   A   G   K   E   W   T   L   A   T   S   G   H   239

719  CGC TAT GCA GTC TGG C                                            734
240   R   Y   A   V   W                                               244
```

FIG. 14

```
         EcoRI
1330   GAATTCTGGCGTTTGCGTGACTCTAAGGGGAAGCCCCCAGGAGTTTTAGGATTGTGGCCT
       ||| ||||| ||||| |||| | | | ||| || | ||  ||| | | ||| ||||| 
308    GAGCUGUGGGGCUGCGCGGCGCACAGACGGUAAGGCGCCAGGCAUGGGGUGGGGCCG

1390   TCAAGGGCTGTCACTTTTATTGATAATCACGACACTGATCAACTCAGGCGCAT TGGCC
       |||||| |||| |  |||  ||||  |  |  ||| ||||  || ||| || | ||| 
368    GCCAAGGCGGUGACCUUUGUGGACAACCACGACACCGGCUCCACGGA GCACAUGGGCC

1449   TTTCCCTTCACGTCAT GTTATGGAGGCTATGCATACATTCTTACACCCAGGATACC
       |||||||| || |||| || ||||| ||| | |||||  | || || |||||| ||| 
427    CUUCCCUUCUGACAGGGUCAUGCAGGGAUAUGCCUACGACAUCCUCACGCACCCAGGACGCC

1509   ATCAGTTTCTTTGACCATTTCTACGAATGGGATAATTCCATGACCAAATTGTAAA
       || || | ||  |||| ||| |   |  |||||  |   | | |||| | ||||  
487    AUGCAUCUUCUACGAUCAUUUCUUCGACUGGG              GCC UGAAGGAGGAGAUCG AUC
                                                                    EcoRI

1569   GCTGATTGCTATTC GGAGGAATCAAGGCATACACAGC CGTTC ATCTATAAGAATTC
       |||  | || ||  ||| || | ||||| || || || ||    ||||| ||  | 
540    GCUUGGUGUCAGUCAGGACCCGGCACGGGAUACACAACGAGAGCAAGCUGCAAAUCAUA

MATCHES = 190    MISMATCHES = 97    UNMATCHED = 12
LENGTH = 299    MATCHES/LENGTH = 63.5 PERCENT
```

FIG. 15A

Potato amylase Amy23/4
Barley amylase B (pM/C)

| Pos | | | | | | | | | | | | | | | | | | | | |
|---|---|---|---|---|---|---|---|---|---|---|---|---|---|---|---|---|---|---|---|---|
| 19 | K | E | I | L | A | Q | L | W | E | S | H | K | D | H | G | W |
| 25 | | Q | L | F | G | V | K | G | A | A | F | H | K | N | A | Y |
| 37 | L | N | L | H | G | S | S | V | G | A | G | P | W | S | V | L |
| 44 | | F | L | G | D | L | P | D | H | A | Y | L | L | Y | L | L |
| 57 | N | P | V | C | P | S | Y | E | P | A | S | N | R | L | K | Q |
| 64 | N | D | A | S | Q | G | L | D | E | K | L | A | M | G | L | G |
| 77 | Y | K | R | V | S | D | K | L | A | K | Y | G | M | H | D | Q |
| 84 | K | G | K | V | P | H | K | L | N | K | A | S | H | P | K | D |
| 96 | Y | K | V | R | A | V | M | A | D | V | H | A | G | V | H | W |
| 104 | K | G | K | G | H | M | Y | A | R | D | Y | R | E | K | M | W |
| 115 | G | G | H | K | G | I | A | H | P | D | F | L | M | S | D | |
| 124 | | G | R | G | H | I | Y | C | H | E | I | T | D | A | L | |

```
             80        90       100       110       120       130
pM/C    GRLYDLDASKYGNKAQLKSLIGALHGKGVKAIADIVINHRTAEHKDGRGIYCIFEGDTPD
            :::::::  :::   ::: : :: :::::::::::::::: ::::::::::::
Amy21   SVFSSRNDSKFGNQQQLKTLIKALHDHGIKSVADIVINHRTADNKDSRGIYSIFEGGTSD
             10        20        30        40        50        60

140       150       160       170       180       190
pM/C    ARLDWGPHMICRDDRPYADGTGNPDTGADFGAAPDIDHLNLRVQKELVEWLNWLKADHRL
          ::::::  ::::: :::::::::::: :  :::::::: ::::::: ::: :
Amy21   DRLDWGPSFICKNDTQYSDGTGNPDTGLDFEPAPDIDHLNTRVQKELSDWMNWLKSEIGF
             70        80        90       100       110       120

200       210       220       230       240       250
pM/C    DGWRFDFAKGYSADVAKIYIDRSEPSFAVAEIWTSLAYGGDGKPNLNQDQHRQELVNWVD
        ::::::: ::  :: :::  :::::  ::::  ::::: ::  :::: ::::::::::
Amy21   DGWRFDFVRGYAPCITKIYMRNTSPDFAVGEFWNSLAYGQDGKPEYNQDNHRNELVGWV-
             130       140       150       160       170
```

FIG. 16B

```
            260       270       280       290       300       310
pM/C        KVGGKGPATTFDFTTKGILNVAVEGELWRLRGTDGKAPGMIGWWPAKAVTFVDNHDTGST
            :  :::::::::::::::  :::::::::: :  : :::::::::::
Amy21       KNAGR-AVTAFDFTTKGILQAAVQGELWRLKDPNGKPPGMIGVLPRKAVTFIDNHDTGST
            180       190       200       210       220       230

320       330       340       350       360       370
pM/C        QHMWPFPSDRVMQGYAYILTHPGTPCIFYDHFFDWGLKEEIDRLVSVRTRHGIHNESKLQ
            : ::::::::: :::::::::::  ::::::::::::  :  :: ::: :: :::
Amy21       QNMWPFPSDKVMQGYAYILTHPGIPSVFYDHFFDWGFMDGISALISIRKRNRICATSNVQ
            240       250       260       270       280       290

380       390       400       410       420
pM/C        IIEADADLYLAEIDGKVIVKLGPRYDVGNLIPGGFKVAAHGNDYAVWQKI
            : ::::: ::  ::::::: :::: :::::::  ::   :::::::::
Amy21       IMASDSDLYIAMIHHKIIVKIGPKLDLGNLIPPNYEVATSGQDYAVWEQK
            300       310       320       330       340
```

64.1% identical amino acids in 343 amino acid overlap between barley clone pM/C and Amy21

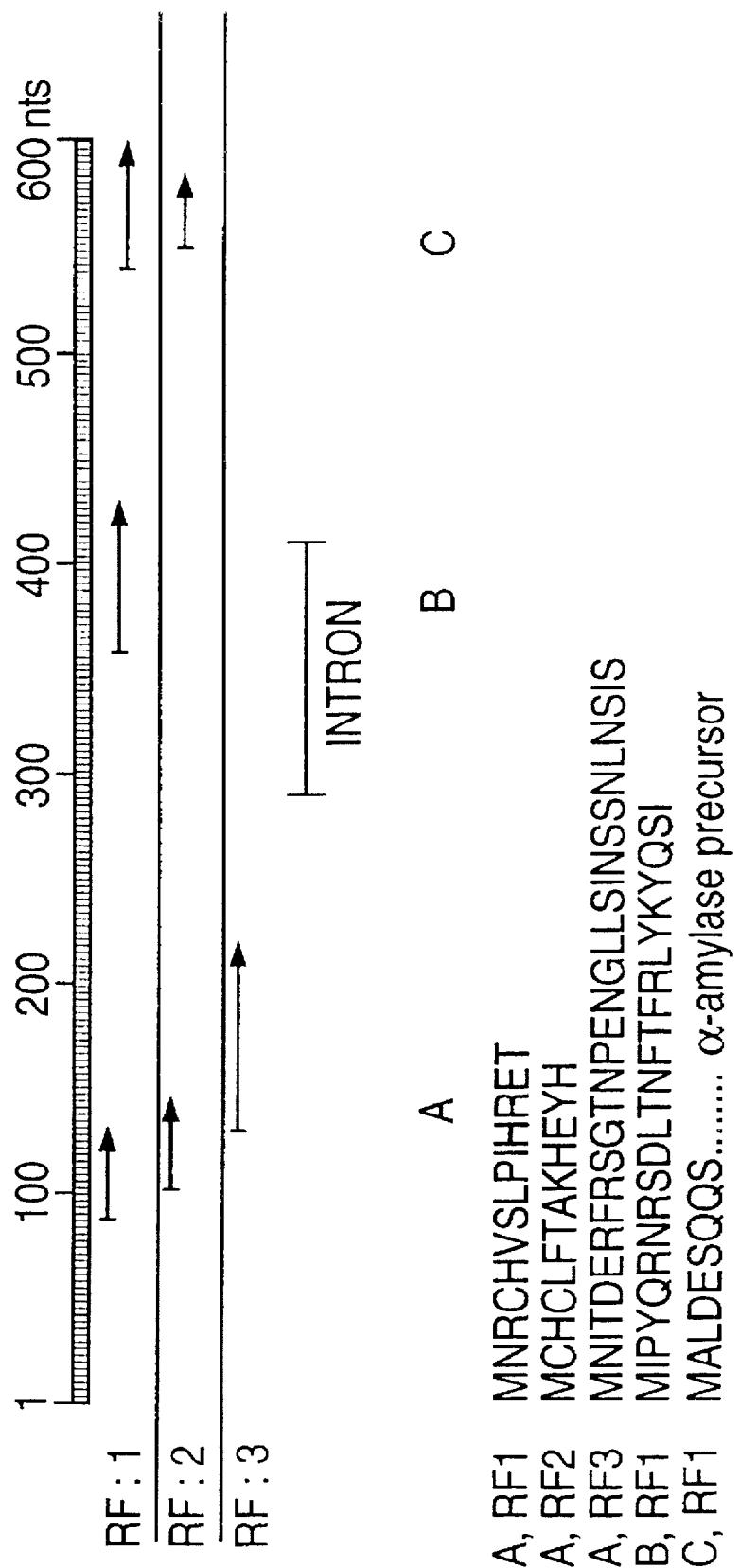

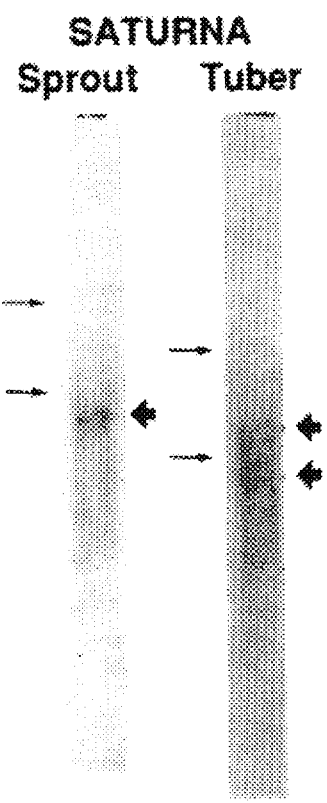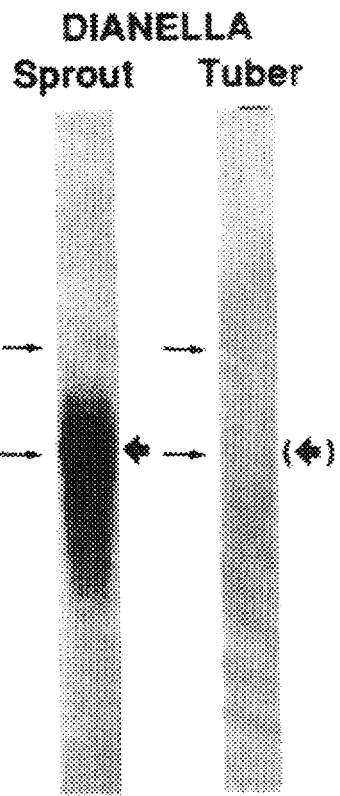

POTATO α-AMYLASE GENES

CROSS-REFERENCE TO RELATED APPLICATIONS

This application is a divisional application of U.S. Ser. No. 08/131,931, filed Oct. 5, 1993, now U.S. Pat. No. 5,498,832, issued May 12, 1996 which is a continuation application of U.S. Ser. No. 07/651,408, filed Feb. 25, 1991, now abandoned, which is the national stage of PCT/DK90/00108, filed Apr. 24, 1990, published as WO90/12876, Nov. 1, 1990.

BACKGROUND OF THE INVENTION

Within recent years, plant genes and regulation thereof have been the object of intensive investigations. The plant genomes are complex and contain a large number of chromosomes which makes the elucidation of genes and especially the regulation thereof very difficult. Also, many plant genes are expressed at different times in the plant development providing differentiation of the plant cells.

α-Amylase, which is involved in the hydrolysis of starch, is present in all plants. α-Amylase in monocotyledonous plants such as barley and wheat has been extensively investigated and α-amylase genes from these monocotyledonous plants have been isolated. α-amylase from dicotyledonous plants has also been investigated, but only at the enzymatic level. It has not been possible to isolate or characterize α-amylase genes from dicotyledonous plants.

The present invention concerns DNA fragments related to the encoding of α-amylase in dicotyledonous plants and to important developments based on the provision of such DNA fragments.

The DNA fragments according to the invention and variants thereof, e.g., an α-amylase encoding part of a nucleotide sequence shown in FIGS. 1–5, as well as subsequences and analogues thereof constitute the basis for transgenic plant strategies for modifying various essential properties of plants, e.g. of the genus Solanum tuberosum, such as deliberately decreasing α-amylase activity to reduce the risk of Maillard reactions and taste modification/degradations in connection with the production of potato chips etc., or for deliberately increasing α-amylase activity in potatoes which are to be used for fermentation for the production of spirits. These strategies, as well as other economically important transgenic plant strategies resulting in modification of the properties of plants made possible through the present invention are explained in greater detail below.

Besides their very important use for direct consumption, potatoes are used for many different industrial purposes such as in a raw material in the production of potato chips and in the production of alcohol. In both types of production, the degradation of starch in the potatoes is of importance and thus, α-amylase involved in the degradation of starch is an important enzyme, as explained below.

In the production of potato chips, the degradation of starch to reducing sugars is critical. A high degree of starch degradation resulting in a high content of reducing sugars causes a problem, since reducing sugar is subjected to the so-called Maillard reactions during the frying of the potatoes in vegetable oil, which causes the chips to acquire an undesirable brown colour and an unpleasant burned taste, accompanied by undesirable alterations in the flavour and texture of the potato chips.

On the other hand, a high content of reducing sugar resulting from a high α-amylase activity is desirable when potatoes are to be used for the production of alcohol.

For reference purposes, a very brief discussion of the use of potatoes for the production of chips and alcohol, respectively, is given below:

The production of potato chips starts with the peeling of the potatoes in special peeling machines. Next, the potatoes are sorted, whereby unfit potatoes, for instance green tubers or potatoes which have been damaged during harvesting, are removed. The potatoes then move on the slicing machines, where they are cut into slices of the appropriate thickness, typically about 1.5 mm. The sliced potatoes are then washed and drained, after which the potato slices are led to a large fryer, which typically has a capacity of about 2000 kg of potato chips per hour. After frying in the hot vegetable oil in the fryer, the potato slices emerge as finished potato chips and are ready for packaging. As mentioned above, undesired Maillard reactions will take place during the frying if reducing sugars are present in the potato slices.

For the production of alcohol from potatoes, the process starts with the boiling of the washed potatoes. The boiling gelatinizes the starch. The potatoes are typically boiled in an autoclave of a temperature of about 150° C. or by use of a continuous process. During the heating to boiling, a thermolabile α-amylase, which has been added to the potato mass, is responsible for an initial saccharification in which an initial conversion of starch to reducing sugars is obtained. After boiling, the gelatinized starch is saccharified by the action of enzymes, whereby the viscous mash is liquified and the starch is converted to fermentable compounds such as glucose. The mash is cooled from a temperature of about 100° C. to about 30° C. before the addition of the enzymes. The enzymes are typically either enzymes extracted from green malt or dry malt (germinated barley) or e.g. bacterial α-amylase or fungal amyloglucosidase. Yeast is added to the mash after saccharification, and the fermentation of the fermentable sugars to alcohol and carbon dioxide takes place over a period of 2–3 days. The alcohol is then removed from the mash by continuous distillation, producing a crude alcohol of about 95% by volume, which can be further purified by rectification.

Starch exists in two different forms, amylose and amylopectin. Amylose, which is an unbranched form of starch, consists of D-glucose units connected by α-1,4 linkages. Amylopectin, which is a branched form of starch, comprises D-glucose units joined by α-1,6 linkages as well as α-1,4 linkages, the ratio between α-1,6 and α-1,4 linkages being on the order of about 1 to 30. It is believed that the branched amylopectins contain about 2000 to about 200,000 glucose units, while the unbranched amylose molecules contain a few thousand glucose units.

Both amylopectin and amylose are hydrolyzed by α-amylase, which hydrolyzes the internal α-1,4 linkages to yield maltose, which consists of two glucose units, maltotriose, which consists of three glucose units, and α-dextrin, which consists of several glucose units comprising an α-1,6 linkage and α-1,4 linkages. The products of hydrolysis by α-amylase, i.e. maltose, maltotriose and α-dextrin, are all further converted to glucose by the action of other enzymes. A different type of amylase, β-amylase, is found in e.g. malt, and hydrolyzes starch to maltose. Starch can in addition be hydrolyzed by the enzyme starch phosphorylase. However, it is believed that only α-amylase is able to hydrolyze intact starch molecules, while β-amylase and starch phosphorylase are only able to act on the products of α-amylase hydrolysis. Thus, while α-amylase hydrolyzes the internal α-1,4 linkages, β-amylase works only on residues at the non-reducing terminus. α-Amylase is therefore a necessary enzyme in the hydrolysis of starch and the conversion of starch to e.g. glucose and fructose.

Food is stored in plants in the form of starch, which is converted to sugar when necessary for use as a source of energy for plant growth. Potato tubers are rich in starch, the starch being converted to sugar upon sprouting and, as explained below, under conditions of storage at relatively low temperatures.

It is commonly known that a portion of the starch in stored potatoes becomes hydrolyzed to glucose during storage of the potatoes, and that the glucose is partially converted to fructose. The rate of hydrolysis of starch to the reducing sugars glucose and fructose increases with decreasing temperatures. Thus, potatoes which are stored for a period of time at a temperature of lower than about 7°–8° C. typically have a relatively higher sugar content, while potatoes stored at a temperature of about 8° C. or higher have a relatively lower sugar content. While this might indicate that the problem of a relatively higher content of reducing sugar in potatoes to be used for chips production could be solved by storing the potatoes at about 8° C. or higher, this is not an ideal solution, since potatoes begin to sprout at an unacceptable rate at such relatively high temperatures. Such sprouting may be prevented or counteracted by spraying the potatoes with an antisprouting agent, but from a consumer's point of view, this is not desirable.

It would be advantageous to be able to reduce the amount of sugar in potatoes of a given potato variety. Thus, as explained above, a reduction of the amount of sugar would be advantageous for potatoes used for the production of potato chips, etc. However, it has not previously been possible to achieve a satisfactory regulation of the sugar content in potatoes by traditional plant breeding methods.

The present invention now opens up the possibility of regulating α-amylase activity by transgenic plant strategies. This and other aspects of the invention will appear from the following description.

SUMMARY OF THE INVENTION

In one aspect, the present invention relates to a DNA fragment comprising a nucleotide sequence substantially as shown in FIGS. 1, 2, 3, 4 or 5 or a subsequence or analogue thereof. The nucleotide sequence shown in FIG. 1 was constructed on the basis of two potato α-amylase cDNA clones by hybridization with a barley α-amylase gene as described in Example 5 and subsequent sequencing (Example 6). The cDNA clones were obtained from a cDNA library constructed from polyA-rich potato RNA as described in Example 4. The potato from which the RNA had been isolated was a potato of the variety Dianella. The nucleotide sequences shown in FIGS. 1 and 2 encode one type of potato α-amylase and the nucleotide sequences shown in FIGS. 3–4 partially encode a second type of α-amylase. The corresponding amino acid sequences are also shown in FIGS. 1–4, respectively. All four α-amylase amino acid sequences are novel and unique. FIG. 5 shows the nucleotide sequence of a partial potato α-amylase cDNA similar to the sequences shown in FIGS. 1–2, the sequence being the product of a pseudo gene which does not encode an α-amylase protein.

In another aspect, the present invention relates to an α-amylase gene comprising a DNA fragment substantially as shown in FIGS. 1–5 or a subsequence or analogue thereof. The term "gene" is used in the present context to indicate a DNA sequence which is involved in producing a polypeptide chain and which includes regions preceding and following the coding region (leader and trailer sequences) as well as intervening sequences, the so-called introns, which are placed between individual coding segments (so-called exons) or in the leader or trailer region. The leader region comprises a regulatory sequence which controls the expression of the gene at the level of transcription and translation. The regulatory sequence includes a promoter. The trailer region comprises sequences which are involved in termination of transcription of the gene and optionally sequences responsible for polyadenylation of the transcript and the 3' untranslated region. The term "subsequence" is used in the present context to indicate a nucleotide sequence which is derived from a DNA fragment or gene of the invention and which has retained a characteristic nucleotide sequence thereof. Typically, the subsequence is a part of a nucleotide sequence shown in FIGS. 1–5, i.e. being a number of nucleotides shorter than one of these nucleotide sequences, the subsequence being either a consecutive stretch of nucleotides taken from a nucleotide sequence shown in FIGS. 1–5 or being composed of one or more separate nucleotides or nucleotide sequences of a nucleotide sequence shown in FIGS. 1–5.

In the present specification and claims, the term "subsequence" designates a sequence which preferably has a size of at least 15 nucleotides, more preferably at least 16 nucleotides, still more preferably at least 18 nucleotides, even more preferably at least 20 nucleotides and most preferably at least 50 nucleotides. It is well known that small fragments are useful in PCR techniques. In particularly preferred embodiments, the subsequence is one hybridizing to any of the DNA sequences referred to above and/or encoding a polypeptide displaying α-amylase activity. Particularly preferred DNA fragments and subsequences according the invention are derived from dicotyledonous plants. The DNA fragments according to the invention preferably have a GC content, calculated as an average for the coding region, in the range of 35–50%, preferably 40–50%.

The term "analogue" with regard to the DNA fragments of the invention is intended to indicate a nucleotide sequence which encodes a polypeptide identical or substantially identical to the polypeptide encoded by a DNA fragment of the invention or a subsequence thereof. It is well known that the same amino acid may be encoded by various codons, the codon usage being related, inter alia, to the preference of the organism in question expressing the nucleotide sequence. Thus, one or more nucleotides or codons of the DNA fragment of the invention may be exchanged by others which, when expressed, result in a polypeptide identical or substantially identical to the polypeptide encoded by the DNA fragment in question. The sequences in FIGS. 1, 2 and 5 represent an example of analogous sequences; the sequences in FIGS. 3 and 4 represent another example. Furthermore, the term "analogue" is intended to allow for variations in the sequence such as substitution, insertion (including introns), addition or rearrangement of one or more nucleotides, which variations do not have any substantial effect on the polypeptide encoded by the DNA fragment or a subsequence thereof. The term "substitution" is intended to mean the replacement of one or more nucleotides in the full nucleotide sequence with one or more different nucleotides. "addition" is understood to mean the addition of one or more nucleotides at either end of the full nucleotide sequence. "insertion" is intended to mean the introduction of one or more nucleotides within the full nucleotide sequence. "deletion" is intended to indicate that one or more nucleotides have been deleted from the full nucleotides sequence whether at either end of the sequence or at any suitable point within it, and "rearrangement" is intended to mean that two or more nucleotides residues have been exchanged with each other.

The terms "fragment", "sequence", "subsequence" and "analogue", as used in the present specification and claims with respect to fragments, sequences, subsequences and analogues according to the invention should of course be understood as not comprising these phenomena in their natural environment, but rather, e.g., in isolated, purified, in vitro or recombinant form.

In the present context, the conventional abbreviations for nucleotides are used, i.e. A represents adenine, T represents thymidine, G represents guanine, and C represents cytosine.

The DNA fragment of the present invention comprising a nucleotide sequence substantially as shown in FIGS. 1-5 may be used for diagnosis, e.g. for RFLP analysis used for detecting the organization of genes encoding α-amylase present in various organisms, preferably plants (see Example 28), and/or for identifying tissues of the organism containing a high amount of α-amylase genes and/or messenger RNA and tissues which do not contain any such genes and/or mRNA. The DNA fragments of the invention may also be used for screening of breeding material for its content of α-amylase messengers, thereby allowing the determination at an early stage of the tendency of the plant breeding material to form reducing sugars, the determination being based on a correlation between α-amylase activity and the amount of reducing sugars produced by a given plant. The present inventors were the first to recognize that such a correlation exists. The early screening of breeding material has a number of advantages and constitutes a novel and very useful approach to characterization of potato breeding material with respect to starch metabolism.

Furthermore, the DNA fragments shown in FIGS. 1 and 2 may be used for preparing a polypeptide, e.g. a potato α-amylase, by use of recombinant DNA techniques. The polypeptide produced constitutes an aspect of the present invention and may be used in the same manner as conventional α-amylase, e.g. in brewing or as a constituent in detergent compositions. As explained below, the DNA fragments shown in FIGS. 3 and 4 represent only partial nucleotide sequences of potato α-amylase messenger RNA and partial amino acid sequences of potato α-amylase precursor. However, although the full length sequences have not yet been deduced, the gene portions which are lacking may be obtained from cDNA or genomic clone libraries isolated by hybridization of α-amylase cDNA clones to the libraries.

BRIEF DESCRIPTION OF THE FIGURES

FIG. 1(A–D) shows the nucleotide sequence of the potato α-amylase messenger RNA deduced from overlapping cDNA clones AmyZ3 and AmyZ4, and the amino acid sequence of the encoded potato α-amylase precursor.

FIG. 2(A–C) shows the nucleotide sequence of the potato α-amylase messenger RNA deduced from cDNA clone AmyZ7, and the amino acid sequence of the encoded potato α-amylase precursor.

FIG. 3(A–C) shows the partial nucleotide sequence of the potato α-amylase messenger RNA deduced from cDNA clone AmyZ1, and the amino acid sequence of the encoded partial potato α-amylase precursor.

FIG. 4(A–B) shows the partial nucleotide sequence of the potato α-amylase messenger RNA deduced from cDNA clone AmyZ6, and the amino acid sequence of the encoded partial potato α-amylase precursor.

FIG. 5(A–B) shows the partial nucleotide sequence of the pseudo potato α-amylase messenger RNA deduced from cDNA clone AmyZ2, and the deduced amino acid sequence of the encoded potato α-amylase precursor before the corresponding gene suffered two deletions.

FIG. 14 shows the homology between potato AmyZ4 and barley α-amylase nucleotide sequences. FIG. 15(A–C) shows the homology between potato AmyZ3/4 and barley α-amylase amino acid sequences. FIG. 16(A–B) shows the homology between potato AmyZ1 and barley α-amylase amino acid sequences.

FIG. 17 shows the open reading frames in the 5' end of the AmyZ3 sequence.

FIGS. 21(a) and 21(b) show Northern hybridization of Saturna and Dianella potato RNA with potato α-amylase probes from AmyZ3.

DETAILED DISCLOSURE OF THE INVENTION

Figure 6:
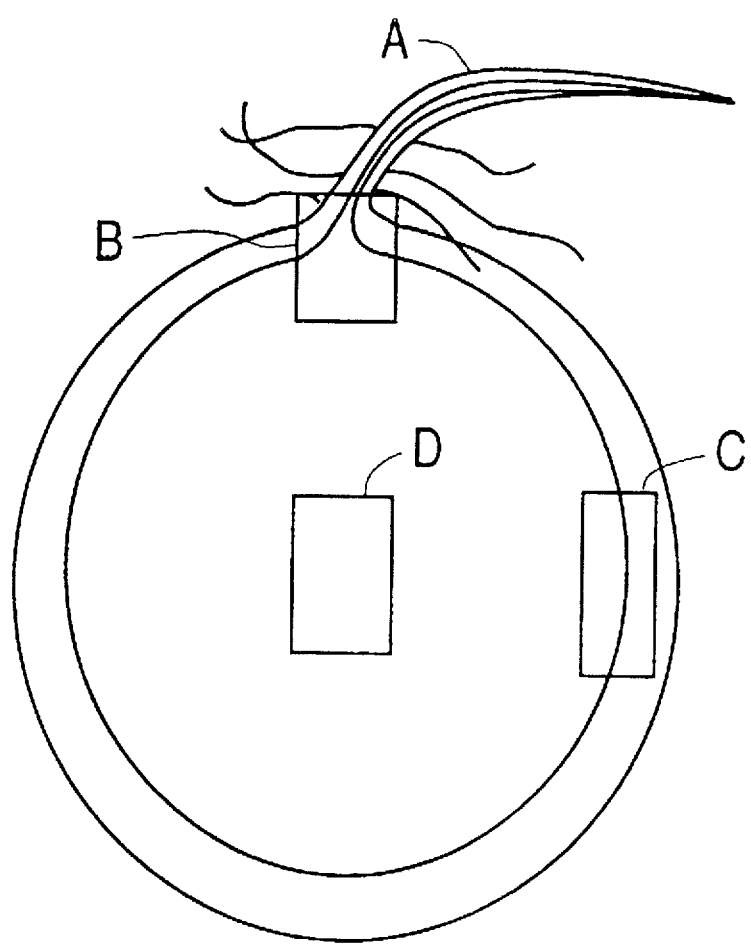
FIG. 6 is a schematic cross-sectional view of a potato showing the tissues from which samples were taken as described in Example 1.

As explained above, the nucleotide sequences shown in FIGS. 1-5 were obtained from a potato cDNA library. More specifically, the nucleotide sequence was obtained from a cDNA library prepared from polyA-rich RNA isolated from sprouts of a potato (*Solanum tuberosum*) of the variety Dianella, as explained below under "Materials and Methods". In the present context, "potato" and "*Solanum tuberosum*" are used interchangeably. The polypeptides encoded by the nucleotide sequences shown in FIGS. 1-4 have substantially the amino acid sequences of two different types of α-amylases from *Solanum tuberosum* of the variety Dianella. In particular, the nucleotide sequences of FIGS. 1 and 2 encode one type of α-amylase, while the nucleotide sequences of FIGS. 3 and 4 encode another type of α-amylase.

The nucleotide sequence shown in FIG. 1 contains one long open reading frame of 407 codons, starting at nucleotide 542 and terminating at nucleotide 1761, the reading frame encoding an α-amylase precursor. The α-amylase precursor comprises a signal peptide, presumably encoded by nucleotides 541–595 and a mature α-amylase enzyme, probably encoded by nucleotide 596 to 1761.

Furthermore, the nucleotide sequence shown in FIG. 1 comprises non-coding regions, i.e. a 5' untranslated region, a so-called 5' leader sequence, which comprises an intron sequence of 128 nucleotides (nucleotides 297–424) and a 3' untranslated region. The nucleotide sequence shown in FIG. 1 is further discussed in Example 8.

The nucleotide sequence shown in FIG. 2 contains one long open reading frame starting at nucleotide 2 and terminating at nucleotide 1219, which reading frame encodes an α-amylase precursor. The mature α-amylase enzyme is presumably encoded by nucleotides 53 to 1219.

As shown in the Examples, different α-amylase cDNA clones were obtained from the potato cDNA library, one of which did not contain an intron (Amy[4]) and one of which (Amy3) contained an intron of a length of 128 nucleotides. The distribution of introns in α-amylase genes, especially potato α-amylase genes, is not known. It has been demonstrated that the α-amylase genes are clustered in a gene family, possibly with only one gene for each of the two types of α-amylase genes characterized represented by different alleles (Example 16). Within a gene family, a high degree of homology between coding regions of the genes is expected, whereas less homology is expected between non-coding regions. For different alleles of the same gene, the homology is expected to be extensive throughout the alleles.

The sequence of events leading to the elucidation of the nucleotide sequences shown in FIGS. 1–5 is described in Examples 2–6. From the explanation given therein, it is evident that isolation of cDNA clones containing nucleotide sequences substantially as shown in FIGS. 1–5 required a great effort regarding the design of the experiments. Thus, it is evident from Example 5 that the frequency of positive clones isolated from the potato α-amylase cDNA library was very low, i.e. approximately 0.008%, which shows that for the construction of a potato cDNA library it was important to choose a tissue in which a sufficiently high amount of α-amylase mRNA is present. Furthermore, the preparation of useful barley α-amylase probes as described in Example 2 was essential, especially with regard to constructing a probe showing optimal hybridization properties to the cDNA clones obtained from potato α-amylase messenger RNA. Such a probe was constructed, which is shown by the fact that all clones hybridizing to the probe were clones having the desired α-amylase nucleotide sequence. Furthermore, it was important to choose suitable hybridization conditions which do not result in too many positive sequences (resulting in "black" filters from which no clear results can be obtained) or in filters which do not result in any hybridization at all. The hybridization conditions allowed isolation of two types of potato α-amylase cDNA clones that are so different that they do not cross-hybridize under normal conditions. Furthermore, in the hybridization DNA from *E. coli* was used as a carrier instead of salmon sperm DNA, which is the conventional carrier used. The use of *E. coli* DNA is very advantageous, since background signals are minimized or substantially avoided.

It was found that the fragments showing the highest degree of hybridization to barley α-amylase genes were DNA fragments comprising nucleotides 1330–1624 as shown in FIG. 1 or nucleotides 387–591 as shown in FIG. 4. It is therefore expected that these or similar fragments may be of particular value in the isolation of α-amylase genes from various dicotyledonous plants other than potato.

The polypeptide expressed from a DNA fragment comprising nucleotides 541–1761 of the nucleotide sequence shown in FIG. 1 or a subsequence or analogue thereof is an α-amylase precursor, i.e. comprising the mature α-amylase enzyme as well as a signal peptide separated by a cleavage or processing site. The signal peptide serves to mediate the transport of the precursor across membranes, e.g. out of the cell or tissue in which it is produced. As described in Example 13, the structure of the signal peptide is atypical, possibly because of an unusual transport mechanism. The α-amylase precursor also constitutes an aspect of the present invention.

Nucleotides 596–1761 of the nucleotide sequence shown in FIG. 1 probably encode a mature α-amylase enzyme, i.e. an enzyme without a signal peptide. While it is contemplated that the α-amylase enzyme in most cases will be prepared in a precursor form, i.e. containing a signal peptide which may subsequently be cleaved off by processing of the precursor by the organism producing it, thereby resulting in the mature α-amylase enzyme, the mature α-amylase may also be produced directly. Thus, in a further aspect, the present invention relates to a DNA fragment comprising substantially the nucleotide sequence starting at nucleotide 596 and terminating at nucleotide 1761 of the nucleotide sequence shown in FIG. 1 or a subsequence or analogue thereof.

Similarly, the present invention relates to a DNA fragment comprising substantially a nucleotide sequence starting at nucleotide 53 and terminating at nucleotide 1219 of the nucleotide sequence shown in FIG. 2 encoding a potato α-amylase, or a subsequence or analogue thereof, a DNA fragment comprising substantially a nucleotide sequence starting at nucleotide 6 and terminating at nucleotide 1052 of the nucleotide sequence shown in FIG. 3 encoding a partial potato α-amylase, or a subsequence or analogue thereof, and a DNA fragment comprising substantially a nucleotide sequence starting at nucleotide 3 and terminating at nucleotide 647 of the nucleotide sequence shown in FIG. 4 encoding a partial potato α-amylase, or a subsequence or analogue thereof.

The invention thus relates to a DNA fragment which is homologous to a nucleotide sequence shown in FIGS. 1–5 or an analogue or subsequence thereof, i.e. one which hybridizes to the DNA sequence under conventional hybridization conditions (12), or under low stringency conditions such as 6×SSC and 67° C. and subsequent wash at 4×SSC and 67° C., and which preferably has a GC content in the range of about 35–50%, more preferably about 40–50%. The term "homology" is used here to denote the presence of any degree of complementarity between a given probe and the nucleic acid species being analyzed. The minimum degree of homology which is detectable is a function of the experimental conditions employed during hybridization and of characteristics of the probe and the nucleic acid species being analyzed. Thus, the size of the probe as well as the complexity of the nucleotide sequence being isolated, e.g. with respect to purity, content of other nucleic acid sequences than the ones related to α-amylase genes, etc. are of importance. As explained in the Examples, sequences homologous to the nucleotide sequences shown in FIGS. 1–4 encoding a potato α-amylase are found in other organisms than the one analyzed, e.g. in other potato varieties or in other dicotyledonous plants of the types disclosed below and should also be considered to be within the scope of the present invention. Thus, corresponding nucleotide sequences encoding α-amylase from other dicotyledonous plants such as other plants of the family Solanaceae, e.g. other potato varieties, may easily be isolated by hybridization under the conditions stated above to a DNA fragment of the invention comprising substantially a nucleotide sequence as shown in FIG. 1 or an analogue or subsequence thereof.

Further, the invention relates to a DNA fragment which is an α-amylase pseudo-gene. The term "α-amylase pseudo-gene" refers to an originally active α-amylase gene which has been mutated in such a way, e.g. by substitutions or deletions, that it is no longer active, but still can be identified as an α-amylase gene by hybridization to a DNA fragment comprising a nucleotide sequence substantially as shown in FIGS. 1–4, or a subsequence or analogue thereof. The cDNA sequence shown in FIG. 5 is an example of the product of an active pseudo-gene.

The α-amylase pseudo-genes will have utilities as explained below for the genes proper.

As described below in the examples, the DNA fragments of the invention may be isolated using a method comprising the steps of:

preparing a cDNA library from poly A-rich RNA isolated from a tissue of a dicotyledonous plant, preferably from poly A-rich RNA from a tissue of a potato plant, in a vector, preferably a λ vector, preferably the λ-ZAP vector;

screening said cDNA library by hybridization with a probe comprising a barley α-amylase gene sequence, under hybridization conditions allowing detection of hybridization without creating an excessive background hybridization, but at the same time allowing the detection of weak hybridization; and isolating recombinant clones which hybridize with the probe, obtaining the DNA fragment from the isolated clones, and optionally producing a subsequence of the DNA fragment by digestion with a restriction enzyme.

The DNA fragments of the invention may be used for isolating similar DNA fragments from various dicotyledonous plants using a method comprising the steps of:

preparing a cDNA library from poly A-rich RNA isolated from a tissue of a dicotyledonous plant, preferably from poly A-rich RNA from a tissue from a potato plant, in a vector, preferably a λ vector, preferably the λ-ZAP vector;

screening said cDNA library by hybridization with a probe comprising a DNA fragment obtainable as described above; and isolating recombinant clones which hybridize with the probe, obtaining the DNA fragment from the isolated clones, and optionally producing a subsequence of the DNA fragment by digestion with a restriction enzyme.

The DNA fragments described above may be produced by various methods, e.g. by building the oligonucleotide sequence of the fragment by oligonucleotide synthesis. In the case of DNA fragment of the invention which is part of a fragment encoding a fusion protein, the fragment may be produced by ligating a DNA fragment of the invention obtainable as described above to a second DNA fragment encoding a second polypeptide or part thereof, preferably using a DNA ligase.

As it will be apparent from the above disclosure, the nucleotide sequences shown in FIGS. 1–5 were derived from a dicotyledonous plant, namely a potato of the variety Dianella. Although nucleotide sequences which may be isolated from other plants, especially other potato varieties than the variety Dianella, may not have the same sequence, they are expected to be homologous to a DNA fragment of the invention to an extent which allows them to hybridize to a DNA fragment comprising a nucleotide sequence substantially as shown in FIGS. 1–5 under the hybridization conditions specified above. As mentioned above, such nucleotide sequences constitute an aspect of the present invention. Typically, nucleotide sequences hybridizing to the DNA fragments of the invention are found in plants of the family Solanaceae, in particular of the genus Solanum, especially *Solanum tuberosum*, or *S. melongena* (aubergine). Other examples are plants of the genus Lycopersicon, e.g. *Lycopersicon esculentum* (tomato), the genus Capsicum, e.g. *Capsicum annuum* (pepper), the genus Nicotiana, e.g. *Nicotiana tabacum* (tobacco), the genus Ipomoea, e.g. *Ipomoea batatus* (sweet potato), the genus Brassica, e.g. *Brassica napus* (rapeseed), the genus Medicago, especially *Medicago sativa* (lucerne), the genus Trifolium spp. (clover), *Glycine max* (soya bean), the genus Arachis, especially *Arachis hypogaea* (peanut), Phaseolus spp., Vicia spp., Vigna spp. (beans), the genus Pisum, especially *Pisum sativum*, root crops such as of the genus Beta, especially *Beta vulgaris* (sugar beet) and the genus Daucus, especially *Daucus carota* (carrots).

A DNA fragment of the invention may comprise one or more second nucleotide sequences encoding a second polypeptide or part thereof so as to encode a fusion protein, at least part of the DNA fragment of the invention being expressed in conjunction with another DNA fragment or gene. For certain purposes, it may be desirable that the polypeptide encoded by a DNA fragment of the invention is in the form of a fusion protein, i.e. a protein in which a polypetide having an amino acid sequence substantially as shown in FIGS. 1–4 or a fragment or an analogue thereof is fused to a second polypeptide. It may be advantageous that the second polypeptide is one which contributes to the properties of the fusion protein, e.g. by modifying, e.g. decreasing or increasing, the activity, e.g. the enzymatic activity of a polypeptide of the invention. Also, a fusion protein may have two or more enzymatic activities, one being an α-amylase activity and the other(s) being an α-amylase activity or an enzymatic activity which, e.g., is normally used together with an α-amylase. Thus, as explained above for the production of alcohol, several different enzymes are used, i.e. one or more cellulases and β-glucosidases. Thus, a fusion protein having α-amylase activity together with cellulase and/or β-glucosidase activity may be advantageous for the production of alcohol. Furthermore, the DNA fragments of the invention or part thereof may be fused to a polypeptide involving transport out of cells or tissues, e.g. a so-called exoenzyme. Signal peptides involving transport will be discussed in further detail below.

The fusion protein may function when expressed in a higher organism such as a plant, but may also be useful in expression from lower organisms such as bacteria or yeasts. Thus, when the polypeptide is to be produced by use of recombinant DNA techniques, e.g. as described below, the recovery or isolation of the polypeptide may be easier and more economical when the polypetide to be recovered is a fusion protein. The second polypeptide to which the polypeptide defined above is fused may be one containing antigenic determinants, against which antibodies may be raised, which antibodies may be used for the recovery of the fusion product, e.g. by using the principles of chromatography such as affinity chromatography, in which the polypeptide may be recovered by means of immobilized antibodies. Procedures for isolating the polypeptide will be dealt with in further detail in the following.

As explained above and in the following examples, the nucleotide sequences shown in FIGS. 1–5 were obtained from a cDNA library constructed from mRNA isolated from the potato variety Dianella. Other sequences, either subsequences, analogues or homologues to the DNA fragment comprising a nucleotide sequence as shown in FIGS. 1–5, in accordance with the definitions given above, obtained from another organism or the same organism and encoding another α-amylase than the ones outlined in FIGS. 1–5, may be obtained in the same manner. Homologous nucleotide sequences may be obtained from complementary cDNA obtained by preparing a cDNA library on the basis of mRNA from an organism producing α-amylase, e.g. by employing a method similar to the one used to obtain the nucleotide sequences shown in FIGS. 1–5. Alternatively, the nucleotide sequence may be derived from the genome of an organism producing α-amylase by screening for genomic sequences hybridizing to a DNA fragment of the invention, e.g. as described below. This may be accomplished by establishing a genomic library of the plant, e.g. potato, and screening for α-amylase clones by hybridization with a DNA fragment of the invention. DNA fragments of the invention comprising a nucleotide sequence substantially as shown in FIGS. 1–5 or a subsequence or analogue thereof may, however, also be synthetic DNA prepared by DNA synthesis in accordance with well known methods.

Most eucaryotic genes contain introns which, as explained above, vary in both size, composition and position between genes belonging to the same gene family. Thus, α-amylase genes or DNA fragments constituting parts thereof may contain introns of varying size, composition and position. These introns may be different from the introns shown in FIG. 1 and thus, the invention also relates to a DNA fragment comprising a nucleotide sequence as shown in FIG. 1 or an analogue or subsequence thereof, especially the part of the sequence encoding a mature α-amylase, i.e. corresponding to nucleotides 596–1761 of the sequence shown in FIG. 1, which DNA fragment further includes one or more non-coding regions such as one or more regulatory sequences and/or introns. In the present context, the term "intron" is used in its conventional meaning, i.e. as a DNA segment which is transcribed, but not translated, since it is removed from within the transcript by splicing together RNA sequences transcribed from the DNA sequences on either side of the intron. An intron may be of a wide variety of sizes and is typically of a size of about 50–500 nucleotides in plants. A DNA fragment of the invention may also contain one or more 5' or 3' untranslated regions which always have to be present in order to obtain expression of the gene or DNA sequence position between the regions. The 5' and 3' untranslated regions are specific for the organism which expresses the DNA fragment or gene and accordingly, the α-amylase encoding sequence should be preceded and followed by 5' and 3' untranslated regions, respectively, which allow for expression in the organism. The untranslated region may be one which is naturally present in the sequence or one which synthetically has been introduced instead of or in addition to the 5' and/or 3' untranslated regions shown in FIGS. 1–4, which regions may vary in composition and/or length, preferably so as to comply with specific requirements of the organism expressing a DNA fragment of the invention.

As explained above, the nucleotide sequence shown in FIG. 1 contains a sequence encoding a signal peptide which is atypical in composition and length. It may furthermore be noted that AmyZ3/4 and AmyZ7 encode identical signal peptides, with the exception that AmyZ7 lacks a Met initiation codon. The nature of a signal peptide used by a given organism depends, inter alia, on the organism and the part thereof, e.g. the specific cell or tissue, in which the polypeptide (precursor) is produced and to which part of the same cell or another location in the organism the polypeptide optionally is to be transported. Thus, a DNA fragment comprising the nucleotide sequence shown in FIG. 1 or a subsequence or analogue thereof, especially nucleotides 596–1761 of the sequence, may have another signal peptide than that of the nucleotide sequence shown in FIG. 1, resulting in a precursor protein different from the one encoded by the nucleotide sequence shown in FIG. 1. The signal peptide may be chosen so as to comply with specific requirements of the organism which is to produce the precursor, including an optional subsequent transport of the precursor within the organism. Typical signal peptides have a core of hydrophobic amino acids and thus, a DNA fragment of the present invention preferably contains a stretch of codons encoding hydrophobic amino acids.

Other peptides that mediate transport are transit peptides that function in the transport into chloroplasts (plastids) and mitochondria. In plants, these peptides are specific for the transport into either organel. Amyloplasts, which are one form of plastid, are the organels in which starch is stored. It may be advantageous to make a fusion of a mature α-amylase and a transit peptide specific for plastids, preferably taken from a soluble plastid peptide, e.g. from the small subunit of ribulose bisphosphate carboxylase, e.g. from potato (Wolter, F. P., Fritz, C. C., Willmitzer, L., Schell, J., and Scheier, P. H. (1988), *Proc. Natl. Acad. Sci., USA* 85, pp. 846–850) or tomato (Sugita, M., Manzara, T., Pichersky, E., Cashmore, A. and Gruissem, W. (1987), *Mol. Gen. Genet.* 209, pp. 247–256). A DNA fragment expressing a transit peptide-α-amylase fusion in a plant would be directed into the amyloplasts, thus facilitating starch degradation.

To procure mature α-amylase in a eukaryotic cell or organism, it may be advantageous to construct a fusion between the 76 amino acid peptide ubiquitin and α-amylase. A DNA fragment expressing a ubiquitin-α-amylase fusion peptide will be processed inside the cells by the poly-ubiquitin processing enzymes, thus precisely producing mature α-amylase without an N-terminal methionine residue (Butt, T. R., Khan, M. I., Marsh, J., Ecker, D. J., and Crooke, S. T. (1988), *J.Biol. Chem.* 263, pp. 16364–16371). The ubiquitin coding region may come from any eukariotic organism, e.g. a plant such as barley (17).

The expression of genes in all organisms is subjected to regulation, which in plants generally has been found to be very complicated, requiring that a network of different regulatory systems and factors function together. Although very little is known about the regulation of plant genes at present, various regulatory mechanisms have been elucidated, two important types of regulation being tissue specific regulation and developmental regulation. To alter the expression of a DNA fragment of the invention or a gene comprising said DNA fragment, a regulatory sequence say be functionally connected to the DNA fragment or gene so as to obtain expression of said fragment or gene under the control of the inserted regulatory sequence. Accordingly, a DNA fragment comprising a nucleotide sequence substantially as shown in FIGS. 1–4 or a subsequence or analogue thereof which further comprises one or more regulatory sequences is within the scope of the present invention. Typically, the regulatory sequence is a promoter which may be constitutive or regulatable. The term "promoter" is intended to mean a short DNA sequence to which RNA polymerase binds prior to transcription of the DNA to which the promoter is functionally connected, allowing transcription to take place. However, in its broader scope, the term "promoter" includes the RNA polymerase binding site as well as regulatory sequence elements located within several hundreds of base pairs, occasionally even further away, from the transcription start site. A "constitutive promoter" is a promoter which is subjected to substantially no regulation such as induction or repression, but which allows for a steady and substantially unchanged transcription of the DNA sequence to which it is functionally bound in all active cells of the organism provided that other requirements for the transcription to take place is fulfilled.

A "regulatable promoter" is a promoter whose function is regulated by one or more factors. These factors may either be ones which by their presence ensure expression of a DNA fragment of the invention or may, alternatively, be ones which suppress the expression of said DNA fragment so that their absence causes the DNA sequence to be expressed. Thus, the promoter and optionally its associated regulatory sequence may be activated by the presence or absence of one or more factors to affect transcription of the DNA fragment comprising a nucleotide sequence substantially as shown in FIG. 1 or an analogue or subsequence thereof.

Other types of regulatory sequences are upstream and downstream sequences involved in control of termination of transcription and removal of introns, as well as sequences responsible for polyadenylation, and initiation of translation. When the regulatory sequence is to function in a plant such as a dicotyledonous plant, e.g. a potato plant, such a regulatory sequence is preferably one which is derived from a dicot plant, e.g. derived from an α-amylase gene.

Factors regulating promoter activity may vary depending, inter alia, on the kind of promoter employed as well as on the organism in which it is to function. Tissue specific regulation may be regulated by certain intrinsic factors which ensure that genes encoding proteins specific to a given tissue are expressed. Such factors are known to exist in mammals and plants so as to allow for specific tissues to develop, and a low number of tissue specific sequences have been described. Among these is the patatin promoter which is known to function in tubers and to a lesser degree in leaves of potato plants. The patatin promoter is a strong promoter and is further described in (44). Also leaf specific promoters have been elucidated. Developmental regulation of plants is involved in structural as well as functional differentiation of cells, tissues or organs during development, e.g. embryonic or regenerative development, which results in the appearance of structures and functions that characterize the different kinds of cells, tissues or organs in different parts of the plant. The mechanisms involved in developmental regulation are far from elucidated, but it has been shown that phytohormones are involved in regulation. Furthermore, it is contemplated that different hormones and other intrinsic factors such as compounds synthesized during seed or plant development and growth are involved in the regulation. It is contemplated that developmental regulation may prove to be useful in the regulation of α-amylase gene expression.

Another type of promoter which has been elucidated is a promoter derived from a plant virus, e.g. a cauliflower mosaic virus (CaMV), a strong constitutive promoter.

Other promoters may be derived from the Ti-plasmid such as the octopine synthase promoter, the nopaline synthase promoter, the mannopine synthase promoter, and promoters from other open reading frames in the T-DNA such as ORF7.

Generally, in order to ensure that the promoters are accepted by the host organism it is advantageous to use a promoter which is isolated from the host organism in question, although a promoter from the same subclass of organisms, e.g. dicots, as a rule functions accurately and efficiently. The regulatory sequence may be an α-amylase promoter, i.e. a promoter which is naturally found in connection with α-amylase genes and involved in the transcription thereof. An α-amylase promoter may be obtained from an isolated α-amylase gene, which may be obtained by hybridization, e.g. as explained in further detail below, to a DNA fragment of the invention comprising a nucleotide sequence substantially as shown in FIGS. 1–5 or a subsequence of analogue thereof. Typically, the α-amylase promoter should be obtained from the same organism as the one in which it is to function, but could also be obtained from another organism, preferably of the same subclass. Optionally, and if desired, the natural promoter may be modified for the purpose, e.g. by modifications of the promoter nucleotide sequence so as to obtain a promoter functioning in another manner than the natural promoter, e.g. being weaker or stronger. Thus, an α-amylase promoter would be suitable for the construction of a transgenic potato plant (which will be discussed in further detail below).

A certain basic α-amylase activity is needed to allow a given plant to grow and develop and to perform its essential metabolical functions. Thus, when designing new plant constructs, especially new potato plant constructs, in which a reduced α-amylase activity is desirable, these constructs are preferably designed so as to allow for a lower expression of α-amylase compared to the expression in the natural plant, while maintaining an expression level which is sufficient to ensure that the metabolic functions essential for growth and development of the plant can be carried out. This may, for instance, apply in the construction of transgenic potatoes for use in the production of potato chips.

A method of decreasing the expression of the intrinsic α-amylase in a plant is at the level of translation. This may be done by providing an anti-sense RNA capable of inhibiting the translation of an mRNA encoded by the intrinsic α-amylase genes, the anti-sense RNA comprising a nucleotide sequence substantially in the opposite orientation as those shown in FIGS. 1–5 or a subsequence or analogue thereof. The terms "intrinsic α-amylase" and "intrinsic α-amylase genes", respectively, refer to the naturally abundant α-amylase enzyme and α-amylase genes in plants, of which there may be several.

As explained in further detail below (see Example 7), the nucleotide sequences shown in FIGS. 1–5 represent two distinctly different types of cDNA clones. One type is represented by clones AmyZ3/4, AmyZ7 and AxyZ2 (FIGS. 1, 2 and 5; "AmyZ3/4 type"), and the other type is represented by clones AmyZ1 and AmyZ6 (FIGS. 3 and 4; "AmyZ1 type"). The mucleotide sequence homology between clones of the two types is low, about 55–60%. Therefore, translation of mRNA from either of the two types may be prevented independently of the other, since the two types are so different. (On the other hand, the homology within each of the types is very high, well over 90%). In order to prevent translation of mRNA from both types of DNA, constructs must be prepared with both types of anti-messenger genes (see Example 24).

For this purpose, the fact that clones AmyZ1 and AmyZ6 are not full length is of relatively little importance.

Thus, in one aspect, the present invention provides a DNA fragment which encodes an anti-sense RNA, i.e. a mRNA molecule capable of hybridizing to a mRNA transcribed from the intrinsic α-amylase genes, thereby inhibiting the translation thereof. The expression of the nucleotide sequence coding for the anti-sense RNA may be either constitutive or regulated. The strength of the promoter regulating the transcription of the nucleotide sequence should be of a magnitude which allows for sufficient quantities of anti-sense RNA to be produced per unit of time to inhibit the translation of the α-amylase mRNA produced by the intrinsic α-amylase genes. The transcription of a DNA fragment encoding an anti-sense RNA may be regulated as described above, for instance by a promoter initiated transcription "in opposite orientation" of a DNA fragment of the invention. As an example, an α-amylase gene promoter may be useful for this purpose, and other types of promoters or other regulatory sequences such as those mentioned above say also be used. The anti-sense RNA must be present in tissues or cells in which the α-amylase genes to be controlled are expressed, so as to be able to hybridize to the intrinsic α-amylase mRNA and thereby inhibit the translation thereof. The DNA sequence encoding the anti-sense RNA must be present in the genome of the plant in order to ensure that the DNA sequence is stably maintained in the host organism.

Preferably, the DNA fragment encoding an antisense RNA molecule is substantially complementary to a DNA fragment of the invention so as to provide an efficient hybridization of the two RNA molecules, thereby ensuring an efficient inhibition of the translation of an α-amylase mRNA to α-amylase. The DNA fragment encoding an antisense RNA molecule is preferably of a size which provides a sufficient degree of homology between the antisense RNA and the mRNA to which it is to hybridize, e.g. the complementary strand of a complete sequence of FIGS. 1–5. Generally, the DNA fragment should be as long as possible, resulting in a high probability of collision and thus hybridization between the RNA transcribed therefrom and the mRNA to which it is to hybridize. Antisense regulation in plants is further discussed in references (59), (60) and (61).

As mentioned above, the present invention also relates to polypeptides encoded by a DNA fragment as defined above, i.e. a DNA fragment comprising a nucleotide sequence substantially as shown in any of FIGS. 1–4 or a subsequence or analogue thereof or a DNA fragment hybridizing therewith under the above specified hybridization conditions. Also an analogue or a fragment of said polypeptide is within the scope of the present invention.

The term "analogue" with regard to the polypeptides of the invention is used in the present context to indicate a protein or polypeptide with a similar amino acid composition and sequence as an amino acid sequence of α-amylase from *Solanum tuberosum* shown in FIGS. 1 or 2, allowing for minor variations in the amino acid sequence, e.g. substitution, deletion, addition, insertion or rearrangement of one or more amino acids in the polypeptide which do not have any substantial adverse effect on the enzymatic properties of the polypeptide as compared to the polypeptides shown in FIGS. 1 and 2. The terms "substitution", "insertion", "addition" and "rearrangement" are explained above in connection with the explanation of the DNA fragments of the invention and are to be understood accordingly. Variations in the carbohydrate moieties, etc. which do not have an adverse effect on the enzymatic properties of the analogue are also comprised by the term "analogue". The term "analogue" covers the term "homologue" in its conventional meaning, i.e. a protein or polypeptide which is developmentally related. The analogous polypeptide or protein may be derived from another organism than *Solanum tuberosum*, e.g. from another dicotyledonous plant, or may be partially or completely of synthetic origin. The term is further intended to mean any enzymatic subsequence, functional equivalent or derivative of an amino acid sequence shown in FIGS. 1 or 2.

The term "enzymatic subsequence" is intended to indicate an amino acid sequence comprising at least one active site of the α-amylase enzyme. By the term "active site" is meant the part of the amino acid sequence which directly or indirectly is involved in the conversion of starch to reducing sugar, i.e. in the hydrolysis of α-1,4 linkages in the starch.

The term "functional equivalent" is intended to included all enzymatically active substances with the ability to convert starch to reducing sugars such as glucose and fructose in a manner similar to α-amylase, i.e. to hydrolyze α-1,4-linkages. The functional equivalent may be derived from an organism different from *Solanum tuberosum*, e.g. from another dicotyledonous plant, or may partially or completely be of synthetic origin. It should be understood that the similarities between the amino acid sequences of α-amylase from *Solanum tuberosum* shown in FIGS. 1 and 2 and the functional equivalent are qualitative rather than quantitative, relating to the nature rather than the level of activity of the functional equivalent.

The present invention also relates to polypeptides derived from a dicotyledonous plant showing a high degree of homology, typically at least about 60%, for example at least about 70%, with an amino acid sequence of a potato α-amylase shown in any of FIGS. 1–4. The term "homology" is intended to indicate the presence of any degree of similarity between a given amino acid sequence and an amino acid sequence shown in FIGS. 1–4. It will be understood that the homology is dependent on the number of amino acid residues to be compared as well as the parts of the amino acid sequence which is actually compared. The term "degree of homology" is to be understood as the fraction of identical amino acid residues in the amino acid sequences to be compared. In the present context, the degree of homology between any two amino acid sequences is the number of identical amino acid residues at corresponding positions in the two amino acid sequences to be compared as compared to the total number of amino acid residues compared in the two amino acid sequences. The degree of homology between two amino acid sequences should be determined for the greatest possible overlap between the two amino acid sequences, i.e. the amino acid sequences to be compared should be placed so as to allow for the greatest possible overlap between identical amino acid residues, resulting in the maximal degree of homology obtainable between the two amino acid sequences to be compared.

The dicotyledonous plant from which the polypeptide is derived is preferably a member of the family Solanaceae, in particular of the genus Solanum, as a high degree of homology between polypeptides from these plants is expected. Thus, α-amylases from any potato plant are expected to be homologous with the polypeptides of the invention. Also, related plants of the family Solanaceae, such as plants of the genus Capsicum, e.g. *Capsicum annuum*, Lycopersicon, e.g. *Lycopersicon lycopersicum*, and Nicotiana, e.g. *Nicociana tabacum*, as well as dicotyledonous plants from other families, are expected to contain polypeptides homologous to the polypeptides of the invention, i.e. α-amylase.

Polypeptides homologous to the amino acid sequences substantially as shown in FIGS. 1–4 or a fragment or analogue thereof may be obtained by isolating genes or messenger RNAs encoding such polypeptides using a DNA fragment of the invention and preparing the polypeptides on the basis of the knowledge of such genes or mRNAs, such as will be explained in further detail below. In particular, it is expected that DNA fragments of the invention, particularly fragments comprising a nucleotide sequence as shown in FIGS. 1–3, can be used for isolating corresponding DNA fragments from plants closely related to potato, for example tomato (Lycopersicon). By preparing an α-amylase in the manner shown below, i.e. by use of recombinant DNA techniques or by liquid or solid phase polypeptides synthesis, it is possible to obtain a polypeptide of the invention in a substantially pure form, which is advantageous for certain purposes.

In the present context, the term "substantially pure" is understood to mean that the polypeptide in question is substantially free from other components, e.g. other components which may influence the enzymatic activity of the polypeptide, which other components may result from the production and/or recovery of the polypeptide or otherwise may be found together with the polypeptide. The high purity of the polypeptides of the invention is advantageous when the polypeptides are to be used because of their enzymatic properties, e.g. in the hydrolysis or decomposition of starch, e.g. in the production of spirits. Because of its high purity, it may have a higher enzymatic activity and thus may be used in a lower amount than a conventional α-amylase used for hydrolysis of starch. For instance, in the production of spirits, in which bacterial α-amylase is used at present, it may be advantageous to use a polypeptide of the invention, especially in its substantially pure form, as the polypeptide of the invention may resemble or be substantially identical to the natural α-amylase enzyme responsible for the hydrolysis of the starch in natural plants. The purity of polypeptides of the invention can be determined by Western blot analysis and visualization of the polypeptides by Coomasie Brilliant Blue staining or other conventionally used methods.

Polypeptides of the invention may be produced by any convenient method, e.g. a method involving the use of recombinant DNA technology or by solid or liquid phase peptide synthesis. Substantially pure polypeptides of the invention having substantially an amino acid sequence shown in FIGS. 1–4, or an analogue or α-amylase related fragment thereof, the polypeptide or analogue or fragment thereof being substantially free of naturally co-occuring enzymes, may be prepared by a method which comprises:

a) inserting a DNA fragment as defined above, i.e. a DNA fragment comprising a nucleotide sequence substantially as shown in FIG. 1 or an analogue or subsequence thereof, optionally in a suitable modified form, in an expression vector, b) transforming a suitable host microorganism with the vector produced in step a), c) cultivating the microorganism produced in step b) under suitable conditions or expressing the polypeptide, and d) harvesting the polypeptide from the culture.

The method may optionally comprise a further step in which the polypeptide produced is subjected to one or more modifications.

In step a) of the method, the modification of the sequence optionally carried out may be performed before or after the sequence has been inserted in the vector. The modification may be carried out in order to adapt the polypeptide expressed from the DNA sequence to a given purpose, e.g. to modify one or more active sites of polypeptide as discussed above. The modification may comprise substitution, addition, insertion or deletion of one or more nucleotides in the sequence or a combination thereof, in accordance with the explanation given above of substitution, addition, insertion, rearrangement or deletion of amino acid residues in the amino acid sequence.

The transformation in step b) of the method may be carried out by standard procedures, such as disclosed in Maniatis et al. (12). The cultivation of the host microorganism in step d) of the method may be carried out in a culture medium conventionally used for fermentation purposes and suited to the host organism in question, and under conditions of pH, temperature, aeration, etc. suited to the type of microorganism in question, e.g. as disclosed in Maniatis et al. (12).

In step d) of the method, the harvesting of the polypeptide or an analogue or fragment thereof may proceed by well-known methods such as by precipitation, gel filtration, ion exchange, HPLC reverse phase chromatography or immunoaffinity chromatography.

The polypeptide produced may be subjected to one or more modifications, e.g. in order to modify one or more active sites thereof, or in order to remove undesired parts of the polypeptide, e.g. a signal sequence, a part of a fusion protein, etc. The modification may be performed in accordance with well-known methods, for instance by thermal treatment, treatment with a chemical such as formaldehyde, glutaraldehyde or a suitable proteolytic enzyme, e.g. trypsin, or substitution, addition, insertion or deletion of one or more amino acids in the polypeptide as explained above.

In an alternative method, the polypeptide or an analogue or fragment thereof may be prepared by the well-known methods of liquid or solid phase peptides synthesis. In solid phase synthesis, the amino acid sequence in constructed by coupling an initial amino acid to a solid support and then sequentially adding the other amino acids in the sequence by peptide bonding until the desired length has been obtained. The solid phase synthesis may be prepared substantially as described by R. B. Merrifield (6). The solid support to which the initial amino acid is coupled may also serve as a carrier for a polypeptide of the invention in cases where it is desirable to couple the polypeptide of the invention to a solid support.

Alternatively, when producing a polypeptide of the invention by use of recombinant DNA techniques such as will be explained in more detail below, the signal sequence mediates transport out of the cell and the fermentation medium containing the recombinant polypeptide may be used as it is prior to any recovery or isolation of the α-amylase enzyme.

In a further aspect, the present invention relates to a vector which is capable of replicating in a host organism and which carries a DNA fragment as described above, i.e. a DNA fragment comprising a nucleotide sequence substantially as shown in FIGS. 1–5 or a subsequence or analogue thereof or an α-amylase gene comprising said DNA fragment or a DNA fragment encoding an antisense RNA molecule capable of hybridizing to a mRNA transcribed from a DNA fragment of the invention. The vector may either be one which is capable of autonomous replication, such as a plasmid, or one which is replicated with the host chromosome, such as a bacteriophage or integrated into a plant genome via the border sequences of Ti vectors. For production purposes, the vector is an expression vector capable of expressing the DNA fragment in the organism chosen for the production. Thus, the expression vector is a vector which carries the regulatory sequences necessary for expression such as the promoter, an initiation signal and a termination signal, etc. The vector may also be one used for diagnosis of α-amylase genes or messengers from potato and other organisms for which purpose expression is not required. Methods of diagnosis are further explained below.

In a still further aspect, the present invention relates to an organism which carries and which is capable of replicating or expressing an inserted DNA fragment as defined above, i.e. a DNA fragment comprising a nucleotide sequence substantially as shown in FIGS. 1–5 or a subsequence or analogue thereof or an α-amylase gene or pseudogene comprising said DNA fragment or a DNA fragment encoding an antisense RNA molecule capable of hybridizing to a mRNA transcribed from a DNA fragment of the invention.

The term "inserted" indicates that the DNA fragment (or subsegment or analogue, or gene or pseudo-gene) has been inserted into the organism or an ancestor thereof by means of genetic manipulation, in other words, the organism may be one which did not naturally or inherently contain such a DNA fragment in its genome, or it may be one which naturally or inherently did contain such a DNA fragment, but in a lower number so that the organism with the inserted DNA fragment has a higher number of such fragments than its naturally occurring counterparts.

The DNA fragment carried by the organism may be part of the genome of the organism, or may be carried on a vector as defined above which is harboured in the organism. The DNA fragment may be present in the genome or expression vector as defined above in frame with one or more second DNA fragments encoding a second polypeptide or part thereof so as to encode a fusion protein, e.g. as defined above.

The organism may be a higher organism such as a plant, preferably a dicotyledonous plant such as a plant of the family Solanaceae, or a lower organism such as a microorganism. A lower organism such as a bacterium, e.g. a gram-negative bacterium such as a bacterium of the genus Escherichia, e.g. *E. coli*, or a gram-positive bacterium such as of the genus Bacillus, e.g. *B. subtilis*, or a yeast such as of the genus Saccharomyces or a fungus, e.g. of the genus Aspergillus, is useful for producing a recombinant polypeptide as defined above. As most organisms inherently produce α-amylase, it may be desirable to modify, i.e. increase, reduce or destroy the inherent α-amylase production, so that the inherent α-amylase production will not influence the preparation of an α-amylase according to the present invention. However, it may be advantageous that the microorganism used for a given recombinant production also produces its natural α-amylase, for instance to obtain an additive effect between the two α-amylases produced. The recombinant production will be explained in further details below.

Examples of such microorganisms are the *E. coli* K-12 strain harbouring the plasmid pAmyZ3 which has been deposited at Deutsche Sammlung von Mikroorganismen (DSM) on 4 Apr., 1989 under the accession number DSM 5275, the *E. coli* K-12 strain harbouring the plasmid pAmyZ4 which has been deposited at DSM on 4 Apr., 1989 under the accession number DSM 5276, the *E. coli* harbouring the plasmid pAmyZ1 which has been deposited at DSM on 18 Apr., 1990 under the accession number DSM 5882, the *E. coli* harbouring the plasmid pAmyZ6 which has been deposited at DSM on 18 Apr., 1990 under the accession number DSM 5883, and the *E. coli* harbouring the plasmid pAmyZ7 which has been deposited at DSM on 18 Apr., 1990 under the accession number DSM 5884.

Also, the organism may be a cell line, e.g. a mammalian cell line, or, more preferably, a plant cell line. Most preferably, the organism is a plant, i.e. a genetically modified plant such as will be discussed in further detail below.

In a further aspect, the present invention relates to a genetic construct useful for inhibiting the translation of a mRNA molecule encoded by a DNA fragment as defined above, comprising a nucleotide sequence substantially as shown in FIGS. 1–5 or a subsequence or analogue thereof, which construct comprises 1) a regulatory sequence functionally connected to 2) a DNA fragment as defined above encoding a RNA molecule capable of inhibiting the translation of the intrinsic α-amylase mRNA, the DNA fragment comprising a nucleotide sequence substantially as shown in FIGS. 1–4 in the opposite orientation or an analogue or subsequence thereof, and 3) a transcription termination DNA sequence, functionally connected to the DNA fragment of 2). The principle of this genetic construct is the construction of a genetically modified plant in which the α-amylase production is reduced so as to obtain a plant having a reduced α-amylase activity. As an example, the genetic construct will be useful in constructing a genetically modified potato plant with a reduced α-amylase activity which results in a reduced amount of reducing sugars in the plant, i.e. a potato plant useful as a raw material for chips production. When the genetic construct is to be used in the construction of a potato plant for this purpose, it is preferred that the DNA fragment is based on a nucleotide sequence which is complementary to a sequence which is well-expressed in potato tubers or one which shows a sufficiently high degree of homology (i.e. hybridizes under the conditions outlined above) to an α-amylase messenger from the tuber, typically one which is normally expressed in another tissue than the tuber, such as in a shoot or leaf. Alternatively, the nucleotide sequence may be transcribed from a pseudogene.

The conditions under which the genetic construct is used should ensure that the antisense RNA-molecule expressed from the genetic construct is allowed to hybridize to an mRNA transcribed from the intrinsic α-amylase genes. Preferably, the genetic construct is active in the same cell or tissue where the intrinsic α-amylase genes are active. Preferably, the genetic construct is stably integrated into the genome to ensure that it is inherited from generation to generation. Useful genetic constructs for reducing the amount of reducing sugars in a potato plant are described in further detail in Example 24.

As discussed above, it may be advantageous to construct an organism with an increased α-amylase activity as compared to the organism in its natural form. Preferably, the organism is a plant, especially a potato plant. A potato plant with an increased α-amylase activity as compared to the potato in its natural form way be used as a raw material for the production of spirits, because an increased α-amylase activity will lead to an increased amount of reducing sugars in the potato, which is advantageous for the spirits production. Accordingly, the present invention relates to a genetic construct useful for producing a polypeptide as defined above, i.e. a polypeptide encoded by a DNA fragment of the invention comprising a nucleotide sequence substantially as shown in FIGS. 1 or 2 or a subsequence or analogue thereof or an α-amylase gene, which construct comprises 1) a regulatory sequence functionally connected to 2) a DNA fragment as defined above encoding the polypeptide, and 3) a transcription termination DNA sequence functionally connected to the DNA fragment of 2).

The genetic construct useful for producing a polypeptide of the invention, e.g. an α-amylase or a part thereof, is preferably used in the construction of a plant having an increased α-amylase activity as compared to a plant not containing the genetic construct. A genetically modified plant having an increased α-amylase activity is advantageous for certain industrial applications, such as in providing a potato raw material having a higher amount of reducing sugar as a consequence of a high α-amylase activity. When constructing a plant having an increased α-amylase activity, the genetic construct should be active in a tissue or cell in which the α-amylase is required for the desired activity or from which the α-amylase may be transported into the place of activity. Preferably, the genetic construct is inserted in connection with another α-amylase gene and may, if desired, be inserted under the control of the α-amylase regulatory sequence of the plant so that no additional regulatory sequence is required. A genetic construct useful for producing a polypeptide as defined above, i.e. an α-amylase or part thereof, may alternatively comprise an α-amylase gene of the invention, i.e. as defined above, from which the promoter has been removed, which gene is fused to a regulatory sequence, preferably a promoter, which is capable of controlling the transcription of the gene. A genetic construct comprising an α-amylase gene without a promoter may be inserted in a plant, i.e. a potato plant, in which an increased α-amylase activity is desirable.

The regulatory sequence contained in the above-defined genetic constructs is preferably a plant promoter such as a constitutive or regulatable plant promoter. The promoter may be of the type discussed above, and when the genetic construct is to be used in a genetically modified potato plant, the promoter is preferably a plant promotes, which may be the CaMV promoter or the NOS promoter, the α-amylase promoter or the promoter from a potato poly-ubiquitin gene. These examples of promoters are illustrative, and other sequences can fulfill the same role. The transcription termination sequence of the genetic construct is a nucleotide sequence capable of terminating the transcription of a DNA fragment and providing a polyadenylation signal and is preferably derived from a plant, i.e. it is preferably a plant transcription termination sequence. It may be derived from the α-amylase gene itself.

The genetic construct may further be provided with a marker which allows for the selection of the genetic construct in a plant cell into which it has been transferred. Various markers exist which may be used in plant cells, particularly markers which provide for antibiotic resistance. These markers include resistance to G418, hygromycin, bleomycin, kanamycin and gentamycin.

As mentioned above, the genetic construct is preferably to be used in modifying a plant. Accordingly, the present invention also relates to a genetically modified plant comprising in its genome a genetic construct as defined above. The genetic construct may be one which is active in reducing the α-amylase activity or one which is involved in increasing the α-amylase activity of the plant. The invention thus further relates to a genetically modified plant which has an increased or decreased α-amylase activity compared to a corresponding non-modified plant. It will furthermore often be desired that a genetically modified plant of the invention is one in which the α-amylase activity may be regulated by various factors, for example by factors such as temperature. For example, when the plant in question is a potato plant, it will for certain purposes be desirable that the α-amylase activity may be regulated, e.g. reduced, at relatively low temperatures, so that potatoes may be stored at low temperatures without the conversion of starch to reducing sugars. Thus, the invention further relates to a genetically modified plant in which the α-amylase activity may be regulated at low temperatures, in particular at temperatures of below about 8° C.

A genetically modified plant may also be one which produces antisense mRNA, which reduces starch decomposition by hybridizing to an mRNA which is transcribed by an α-amylase gene. The invention therefore further relates to a genetically modified plant, in particular Solanum tuberosum, which produces mRNA which is capable of hybridizing to an mRNA transcribed from a DNA fragment as shown in FIGS. 1–4, thereby inhibiting the translation thereof and reducing starch decomposition compared to a corresponding non-modified plant.

As explained above, α-amylase genes from other dicotyledonous plants than potato are expected to have a high degree of homology with a DNA fragment of the invention comprising the nucleotide sequence substantially as shown in FIGS. 1–5 or a subsequence or analogue thereof or an α-amylase gene of the invention as defined above. Thus, the plant to be modified by the genetic construct of the invention is preferably a dicotyledonous plant, since the genetic construct is expected to be active in such plants, especially with regard to reducing the amount of α-amylase in the plant, as a high degree of homology is expected from such constructs. Preferably, the plant is a member of the family Solanaceae, in particular of the genus Solanum, especially Solanum tuberosum. Alternatively, the nucleotide sequences shown in FIGS. 1–5 may be used to isolate corresponding sequences from other plants, whereupon they may be modified as described herein.

In recent years, a great effort has been focused on developing useful methods for constructing novel plants or plant cells having specific and desirable properties, and a number of such methods based on recombinant DNA technology and suitable plant transformation systems are now available. It is contemplated that plants of the invention, e.g. plants having the properties described above, may readily be constructed by use of such methods, examples of which will be explained in detail below.

The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. Thus, in another aspect, the present invention relates to a vector system which tarries a genetic construct as defined above and which is capable of introducing the genetic construct into the genome of a plant such as a plant of the family Solanaceae, in particular of the genus Solanum, especially Solanum tuberosum. The vector system may comprise one vector, but comprises preferably two vectors; in the case of two vectors, the vector system is normally referred to as a binary vector system. Binary vector systems are described in further detail in "Binary vectors" (53).

One extensively employed system for transformation of plant cells with a given genetic construct, e.g. as described above, is based on the use of a Ti plasmid from Agrobacterium tumefaciens or a Ri plasmid from Agrobacterium rhizogenes (42, 54). A. tumefaciens is known to elicit crown gall disease in plants resulting in the growth of plant tissue which produces one or more amino acid derivatives, known as opines, which are not normally produced by the plant. This tissue may be regenerated into whole plants that retain certain transformed phenotypes, e.g. phenotypes encoded by sequences carried on the Ti or Ri plasmid. The Ti and Ri plasmids carry so-called T-DNA (transferred DNA), which in tumors has been found to be stably integrated into the genome of the host plant, and further carry a virulence region which is essential for the formation of plant tumors but not involved in the maintenance thereof. The native T-DNA comprises several genes, each of which is under control of a T-DNA promoter, and further contains genetic information involved in the replication of the plasmid. The T-DNA promoters resemble eukaryotic promoters in structure, and apparently, function only in the plant host cell. Foreign DNA, e.g. a DNA fragment of the invention, may easily be inserted in a Ti or Ri plasmid by use of conventional methods in the field of genetic engineering and thus the Ti or Ri plasmid may serve as a vector for carrying genetic information into a suitable plant cell. Before using the Ti or Ri plasmid as a vector, the genes involved in the formation of tumors are preferably removed so as to avoid any interference from these.

Several different Ti and Ri plasmids have been constructed which are suitable for the construction of the plant or plant cell constructs described above. Non-limiting examples of such Ti plasmids are given in Example 24 and 25 below, a further example being pGV3850. Suitably, the vector to be used is provided with suitable markers, e.g. genes encoding antibiotic resistance or herbicide resistance, so as to be able to determine whether the DNA insert has been inserted in the desired position in the plasmid and to be able to select plant cells transformed with the vector.

The DNA fragment of the invention to be inserted into the Ti-plasmid should preferably be inserted between the terminal sequences of the T-DNA or adjacent to a T-DNA sequence so as to avoid that the sequences immediately surrounding the T-DNA borders are disrupted, as at least one of these regions appear to be essential for insertion of modified T-DNA into the plant genome.

As will be understood from the above explanation, the vector system of the invention is preferably one which contains a virulence function capable of infecting the plant and at least one border part of a T-DNA sequence, the border part being located on the same vector as the genetic construct. Furthermore, the vector system is preferably an *Agrobacterium tumefaciens* Ti-plasmid or an *Agrobacterium rhizogenes* Ri-plasmid or a derivative thereof, as these plasmids are well-known and widely employed in the construction of transgenic plants; many vector systems exist which are based on these plasmids or derivatives thereof.

In the construction of a transgenic plant using a vector it is preferred that the genetic construct to be inserted in the plant is first constructed in a microorganism in which the vector can replicate and which is easy to manipulate. An example of a useful microorganism is *E. coli*, but other microorganisms having the above properties may be used. When a vector of a vector system as defined above has been constructed in *E. coli*, it is transferred, if necessary, into a suitable Agrobacterium strain, e.g. *Agrobacterium tumefaciens*.

The Ti-plasmid harboring the DNA fragment of the invention is thus preferably transferred into a suitable Agrobacterium strain, e.g. *A. tumefaciens*, so as to obtain an Agrobacterium cell harboring the DNA fragment of the invention, which DNA is subsequently transferred into the plant cell to be modified. This transformation may be performed in a number of ways, e.g. as described in (53) and in EP 0 122 791. However, for potato and other Solanaceae, infection of leaf pieces using *A. tumefaciens* is most often employed (74).

Direct infection of plant tissues by Agrobacterium is a simple technique which has been widely employed and which is described in (54). Typically, a plant to be infected is wounded, e.g. by cutting the plant with a razor or puncturing the plant with a needle or rubbing the plant with an abrasive. The wound is then inoculated with the Agrobacterium, e.g. in a solution. Alternatively, the infection of a plant may be done on a certain part or tissue of the plant, i.e. on a part of a leaf, a root, a stem or another part of the plant. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

It is contemplated that a DNA fragment of the invention, especially its regulatory sequences, may be used in a method of expressing other polypeptides than the polypeptides of the invention, e.g. proteins or enzymes not related to α-amylase. In particular, this may apply for the production of plant polypeptides normally expressed in a developmental manner or a tissue or cell specific manner corresponding to the manner in which α-amylase is expressed, but also other biological substances are of interest, e.g. pharmaceutical products, colorants, flavorings, plant hormones, primary and secondary metabolites, etc., which may either be directly produced by expression of a DNA sequence encoding the substance or may be produced as a result of the action of a substance expressed from a DNA sequence. As described above, α-amylase gene expression is characteristic for genes encoding enzymes (as opposed to structural proteins or storage proteins), i.e. the level of expression is relatively low, on the order of about 0.01% of the total messenger RNA in shoots is an α-amylase messenger RNA, evaluated on the basis of the cloning frequency.

More specifically, other polypeptides may be expressed from a construct comprising a regulatory region normally involved in the transcription of an α-amylase gene, e.g. an α-amylase promoter, and a DNA sequence encoding the polypeptide to be produced fused to each other in such a manner that the expression of the DNA sequence is under control of the regulatory region. This construct may be inserted into a suitable plant transformation system, e.g. as described above, and introduced into the genome of a plant, in which it is stably maintained and expressed.

As will be understood from the introductory part of the present specification, the DNA fragment of the present invention may be used for diagnostic purposes, which will be further explained in the following.

Various types of diagnosis may be performed by use of the DNA fragment of the invention. In a given sample, α-amylase messenger RNA's may be qualitatively as well as quantitatively determined by hybridization to the DNA fragment of the invention under conditions suited for said hybridization. Furthermore, genes encoding α-amylase present in an organism such as a plant may be identified and isolated by use of the DNA fragment of the invention, e.g. by screening a gene library of such an organism.

When the DNA fragment is to be employed for diagnostic purposes, it will often be useful to provide it with a label which may be used for detection. Thus, in a further aspect the present invention relates to a DNA fragment as defined above which is provided with a label. Preferably, the label is selected from the group consisting of fluorophores, radioactive isotopes, isotopes and complexing agents such as biotin.

Examples of radioactive isotopes useful as label substances are $H^3$, $C^{14}$, $S^{35}$ and p32. The radioactivity emitted by these isotopes may be measured in a gamma-counter, a scintillation counter or by radioautography followed by densitometry in a manner known per se.

Complexing agents may be e.g. Protein A, biotin (which forms a complex with avidin and streptavidin) or lectin. In this case, the complex is not in itself directly detectable, necessitating labelling of the substance with which the completing agent forms a complex. Any of the labels disclosed above may be used for this purpose.

In a further aspect, the present invention relates to a method of isolating an α-amylase gene or messenger from an organism, e.g. a plant, in particular a dicotyledon, the method comprising hybridizing a nucleic acid containing sample obtained from a gene library or cDNA library from the organism with a DNA fragment of the invention comprising a nucleotide sequence substantially as shown in FIGS. 1–5 or a subsequence or analogue thereof, optionally in a labelled form, in a denatured form or an RNA copy thereof under conditions favorable to hybridization between the DNA fragment or RNA copy and the nucleic acid of the sample, and recovering the hybridized clone so as to obtain an α-amylase gene or cDNA of the organism.

The identification and isolation of an α-amylase gene or cDNA clone in a sample by use of the DNA fragment of the invention may be based on standard procedures, e.g. as described in Maniatis (12). For instance, to characterize α-amylase genes in other plants, it is preferred to employ standard Southern techniques, e.g as described in Example 16 and "Material and Methods".

In a still further aspect, the invention relates to a method of quantifying the amount of an α-amylase messenger present in different tissues in an organism, e.g. a plant, in particular a dicotyledon, the method comprising hybridizing a nucleic acid containing sample obtained from the organism with a DNA fragment of the invention comprising a nucleotide sequence substantially as shown in FIGS. 1–4 or a subsequence or analogue thereof, optionally in labelled form, in denatured form or an RNA copy thereof under conditions favorable to hybridization between the denatured DNA fragment or RNA copy and the RNA of the sample and determining the amount of hybridized nucleic acid (40).

Measurement of the α-amylase messenger may be of importance as it is contemplated that there is a relationship between the amount of α-amylase messenger in a cell and the amount of α-amylase enzyme produced. Establishing the amount of α-amylase messenger may therefore be used for plant breeding purposes, e.g. when it is desired to combine a plant's characteristic content of reducing sugars with another trait.

The hybridization should be carried out in accordance with conventional hybridization methods under suitable conditions with respect to e.g. stringency, incubation time, temperature, the ratio between the DNA fragment of the invention to be used for the identification and the sample to be analyzed, buffer and salt concentration or other conditions of importance for the hybridization. The choice of conditions will, inter alia, depend on the degree of complementarity between the fragments to be hybridized, i.e. a high degree of complementarity requires more stringent conditions such as low salt concentrations, low ionic strength of the buffer and higher temperatures, whereas a low degree of complementarity requires less stringent conditions, e.g. higher salt concentration, higher ionic strength of the buffer or lower temperatures, for the hybridization to take place.

The support to which DNA or RNA fragments of the sample to be analyzed are bound in denatured form is preferably a solid support and may have any convenient shape. Thus, it may, for instance, be in the form of a plate, e.g. a thin layer or a microtiter plate, a strip, a solid particle e.g. in the form of a bead such as a latex bead, a filter, a film or paper.

The solid support may be composed of a polymer, preferably nylon or nitrocellulose.

The DNA fragment used for detecting the presence of the α-amylase gene is preferably labelled, e.g. as explained above, and the presence of hybridized DNA is determined by autoradiography, scintillation counting, luminescence, or chemical reaction.

Another approach for detecting the presence of a specific α-amylase gene, e.g introduced by the genetic methods described previously, or a part thereof in an organism, e.g. a plant, in particular a dicotyledon, is to employ the polymerase chain reaction (5), i.e. using a method in which the DNA fragment which comprises the α-amylase gene or part thereof in a sample is subjected to multiple fold amplification. The polymerase chain reaction (PCR) is a procedure used for the amplification of DNA present in a sample. The procedure involves the use of two oligonucleotide primers which flank the DNA fragment to be amplified. The oligonucleotide primers may e.g. be 10- to 20-mers and comprise the flanking regions of the α-amylase gene or part thereof. The oligonucleotide primers are constructed so as to enable hybridization of one primer to the plus strand 5' of the target DNA, and of another primer to the minus strand 5' of the target DNA. The primers are hybridized with the opposite DNA strands to be amplified and are extended by using DNA polymerase, e.g. the Klenow fragment of $E.$ $coli$ DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, separated from the "parent DNA strings", and the parent strings as well as the newly synthesized DNA strings are subjected to a new PCR amplification cycle. In this manner, it is possible to obtain a substantial amplification of specific DNA sequences which are present in the organism to be analyzed. By use of the PCR amplification method, it is possible to detect the presence of DNA sequences encoding α-amylase in very small samples, e.g. embryos or even single cells.

The sample to be analyzed for the presence of an α-amylase gene or part thereof in accordance with the methods outlined above may be taken from the group of plant parts consisting of leaves, stems, tubers, flowers, roots, sprouts, shoots and seeds.

The methods outlined above for detecting the presence of α-amylase genes or messengers in a sample may be of particular importance in plant breeding programmes. Based on the observations that reducing sugar content in stored potatoes is correlated with α-amylase activity as described in the Examples, and that the correlation extends to shoots and presumably to other parts such as the leaves, potato varieties can be screened for their tendency to accumulate sugar in stored potatoes already at a stage when young plantlets have formed a few leaves, i.e. at a very early stage. This may, e.g., be performed by spotting RNA extracts from 0.1 to 0.5 grams of leaves (e.g. obtained as described below in "Materials and Methods") on filters suitable for hybridization and hybridizing with a DNA fragment of the invention, optionally provided with a label such as biotin or an radioactive isotope. As a reference, hybridization with similarly labeled ubiquitin coding regions from any organism, e.g. barley, may be used, as ubiquitin sequences are extremely well conserved and constitutively expressed in different plant tissues. The results are compared with similar dot blots obtained from analysis of potato varieties with known sugar characteristics, e.g. from the four potato varieties described in "Materials and Methods". A dot blot analysis as described above may be carried out on a large amount of breeding material and lead to early determination of the sugar characteristics of a given potato variety.

Restriction fragment length polymorphisms (RFLP) are increasingly used to follow specific alleles of genes in various organisms. The alleles are either themselves followed or they are used as markers (unlinked or linked) in crosses involving other characteristics, e.g. pathogen resistance and morphological characteristics such as tuber colour. So far, the method has primarily been employed in humans, but it has also been employed in plants, e.g. in potatoes (27). It is contemplated that a DNA fragment of the invention may be useful in RFLP-analysis of α-amylase genes, especially in dicotyledonous plants such as in potato, based on the results of genomic Southern hybridization of potato DNA with an isolated DNA fragment of the invention. Plants of the species *Solanum tuberosum* have few α-amylase genes and therefore yield a simple fragment pattern that make polymorphisms easy to evaluate. Thus, genomes may be analyzed for alleles encoding α-amylase as described above using the principles of restriction fragment length polymorphism, i.e. as described in (27). An example of the use of α-amylase genes in this technique is given in Example 28 and the accompanying FIGS. 19 and 20.

In the present context, the abbreviations for the amino acids are those conventionally used.

DETAILED DESCRIPTION OF THE DRAWINGS

FIG. 1 shows the nucleotide sequence of a potato α-amylase messenger and the deduced amino acid sequence of potato α-amylase precursor. The figure shows the sequence of the messenger RNA-like strand of the combined inserts of potato α-amylase cDNA clones AmyZ3 and AmyZ4 without the terminal EcoRI sites. AmyZ3 and AmyZ4 have identical nucleotide sequences in the regions where they overlap (cf. FIG. 11), except that AmyZ3 has an intron sequence of 128 nucleotides which is underlined in the figure (nucleotides 296 to 423, inclusive). The consensus 5' and 3' splice junction nucleotides, GT and AG, respectively, are double-underlined in the figure. A consensus branch point, (nucleotides 390 to 396) is boxed. The nucleotide sequence of the 3' leader until nucleotide 540 contains four open reading frames, which are shown in detail in FIG. 17. The region encoding the α-amylase precursor starts at nucleotide 541 and terminates at nucleotide 1761, and the length of the α-amylase precursor is 407 amino acids. In the figure, the derived amino acid sequence is shown using the one letter code for the amino acids. The probable processing site of the precursor is shown by an arrow. The 3' untranslated region is at least 200 nucleotides in length, not including the polyA tail, but probably not much longer, since a putative polyA signal is found 30 nucleotides from the end. The polyA signal is underlined in the figure.

FIG. 2 shows the nucleotide sequence of potato α-amylase messenger and deduced amino acid sequence of potato α-amylase precursor. The figure shows the sequence of the messenger RNA-like strand of the insert of potato α-amylase cDNA clone AmyZ7 without the terminal EcoRI sites. The nucleotide sequence encodes an α-amylase precursor starting at amino acid number two and the sequence includes the G residue (No. 1 in the figure) of the initiation codon ATG. The α-amylase reading frame terminates at position 1219, and the length of the α-amylase precursor is 407 amino acids, including the initiation codon. The probable processing site of the precursor is shown by an arrow. The sequence terminates with a 187 nucleotides long 3' untranslated region followed by a polyA tail nine residues long.

FIG. 3 shows the partial nucleotide sequence of potato α-amylase messenger and deduced amino acid sequence of a partial potato α-amylase precursor. The figure shows the sequence of the messenger RNA-like strand of the insert of potato α-amylase cDNA clone AmyZ1 without the terminal EcoRI sites. The partial α-amylase open reading frame starts at nucleotide 6 and terminates at nucleotide 1052 and the first amino acid aligns with amino acid 69 of the sequence shown in FIG. 1. The AmyZ1 clone thus lacks nucleotides encoding the signal peptide and approximately 50 codons from the N-terminus of mature α-amylase. The sequence terminates with a 163 nucleotides long 3' untranslated region.

FIG. 4 shows the partial nucleotide sequence of potato α-amylase messenger and deduced amino acid sequence of a partial potato α-amylase precursor. The figure shows the sequence of the messenger RNA-like strand of the insert of potato α-amylase cDNA clone AmyZ6 without terminal EcoRI sites. The partial α-amylase open reading frame starts at nucleotide 3 and terminates at nucleotide 647 and the first amino acid aligns with amino acid 133 of the sequence shown in FIG. 1. The sequence terminates with a 360 nucleotides long 3' untranslated region.

FIG. 5 shows the partial nucleotide sequence of a pseudo potato α-amylase messenger and deduced amino acid sequence of the α-amylase that the sequence encoded before the corresponding gene suffered two deletions. The figure shows the sequence of the messenger RNA-like strand of the insert of potato α-amylase cDNA clone AmyZ2 without the terminal EcoRI sites.

FIG. 6 is a schematic cross-sectional view of a potato showing the tissues from which samples were taken as described in Example 1; A: sprout in itself without any leaves or roots; B: connection between sprout and tuber; C: vascular tissue of the tuber; D: parenchym tissue.

Figure 7:
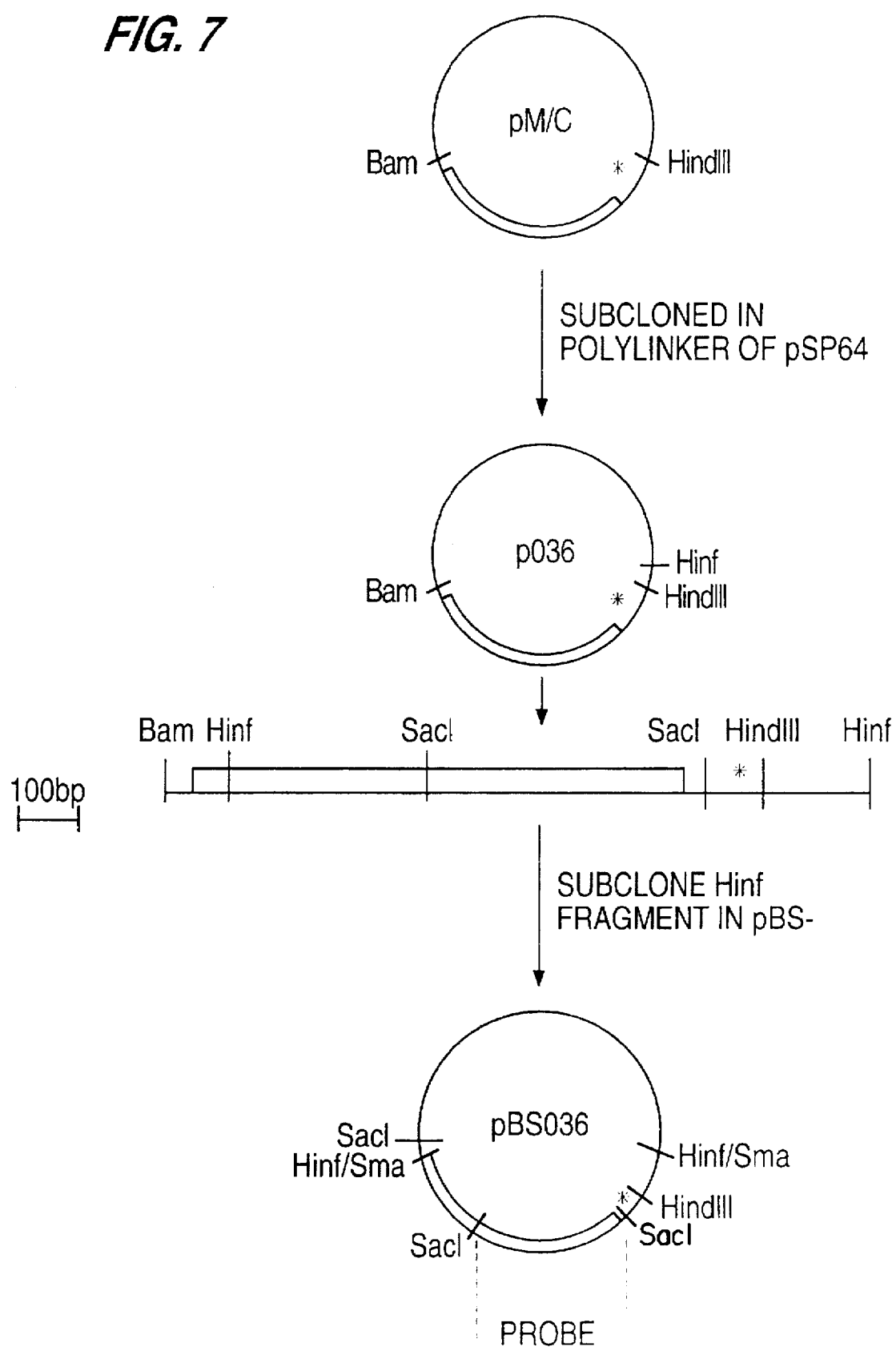
FIG. 7 shows the structure and subcloning of barley α-amylase cDNA clone PM/C.

FIG. 7 shows the structure and subcloning of barley α-amylase cDNA clone pM/C. Plasmid 036 was the clone received from J. C. Rogers with the information that it is a BamHI-HindIII subclone of pM/C (24).

However, the complete sequence was not published, and the short unknown sequence is indicated by a star. From plasmid 036, the indicated Hinf fragment was subcloned in pBS- to generate a plasmid yielding high copy numbers, pBS036, which was analyzed as described in Example 3 (the results of which are shown in FIG. 4), and used as a source of the hybridization probe which is the SacI fragment indicated at the bottom of the figure. Single lines indicate vector sequences and noncoding barley sequences; double lines indicate the barley α-amylase coding region.

Figure 8A:
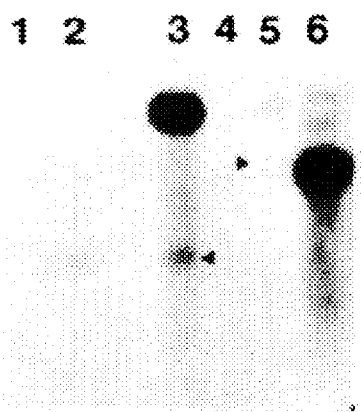
FIGS. 8a, 8b, and 8c show hybridization of barley α-amylase cDNA fragments with radioactive cDNA from polyA-rich RNA from Dianella potato sprouts.
Figure 8B:
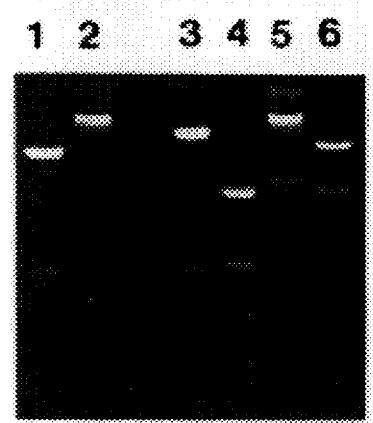
Figure 8C:
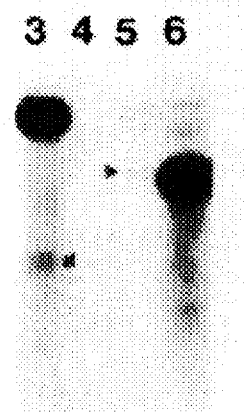

FIG. 8 shows hybridization of barley α-amylase cDNA fragments with radioactive cDNA from polyA-rich RNA from potato (Dianella) sprouts. Restriction enzyme fragments from barley α-amylase cDNA clones and control plasmids were fractionated in duplicate on a 2% agarose gel and the ethidium bromide stained fragments are shown in panel b). The fragments were transferred to nitrocellulose filters and one filter was hybridized with 5 million cpm of radioactive cDNA made from Dianella sprout polyA-rich RNA (panel a). The other filter was hybridized with 4 million cpm of radioactive cDNA made from barley leaf polyA-rich RNA. Both filters were hybridized at low stringency (hybridization at 67° C. in 6×SSC, wash at 67° C. in 4×SSC). The panels a) and b) show autoradiograms of the filters. The plasmid DNA in the different lanes (2 µg/lane) was as follows: Lane 1, pBR327 digested with EcoRI and PstI (liberates a 723 bp fragment that serves as a negative control); lane 2, pKG3730 digested with PstI (liberates a 780 bp fragment encoding barley ubiquitin, ubiquitin genes are highly conserved and found in all eukaryotes (17)—the fragment serves as a positive control); lane 3, pBS036 digested with SacI (liberates the 800 bp fragment subsequently used as probe); lane 4, pBR327 digested with BstNI (size markers, 1855 bp, 928 bp, and 475 bp); lane 5, plasmid pBS050 digested with PstI (liberates a cDNA fragment encoding barley α-amylase type A); lane 6, plasmid 036 digested with BamHI and HindIII (liberates the fragment subcloned from pM/C, see FIG. 7). Strong bands in panel a) and b) are unexplained, false hybridizations to the unknown region of plasmids 036 and pBS036, indicated with stars in FIG. 7. The weaker bands indicated with triangles are the specific hybridizations of the barley α-amylase coding regions. Lane 2 in panel a) shows that potato messenger RNA, as expected, contains ubiquitin coding sequences.

Figure 9:
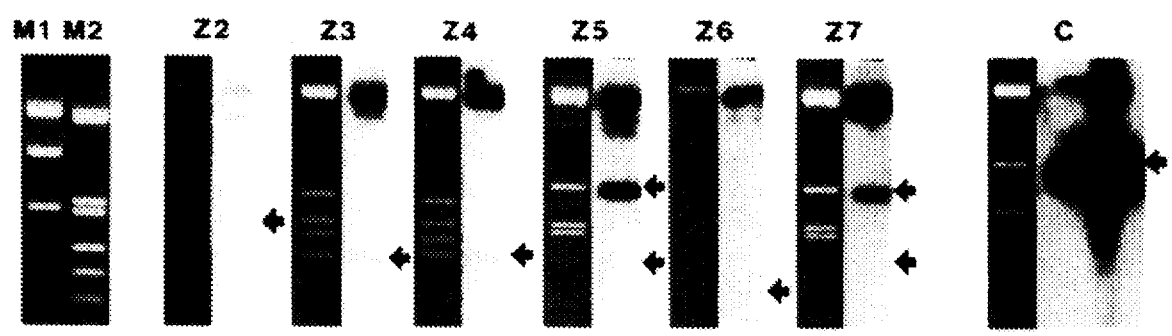
FIG. 9 shows Southern analysis of the putative potato α-amylase cDNA clones.

FIG. 9 shows analyses of the putative potato α-amylase cDNA clones. Plasmid DNA from six of the eight purified plasmids from the potato cDNA library was digested with EcoRI, fractionated on a 2% agarose gel, and stained with ethidium bromide (black lanes). The fragments were transferred to a nitrocellulose filter and the filter was hybridized at low stringency (hybridization at 67° C. in 6×SSC, wash at 67° C. in 4×SSC) with a nick-translated barley α-amylase SacI probe. The white lanes show the resulting autoradiograms, and the hybridizing EcoRI fragments seen in the original autoradiogram are indicated with arrows. The full names given to the plasmids are AmyZ2, AmyZ3, AmyZ4, AmyZ5 AmyZ6 and AmyZ7. M1 and M2 are size markers. M1 is pBR327 digested with BstNI (1855 bp, 928 bp, and 475 bp), M2 is pBR327 digested with HinfI (1631 bp, 517 bp, 452 bp, 298 bp and 154 bp) Panel C shows the homologous hybridization of pBS036 digested with SacI to the SacI probe performed in the same experiment.

Figure 10:
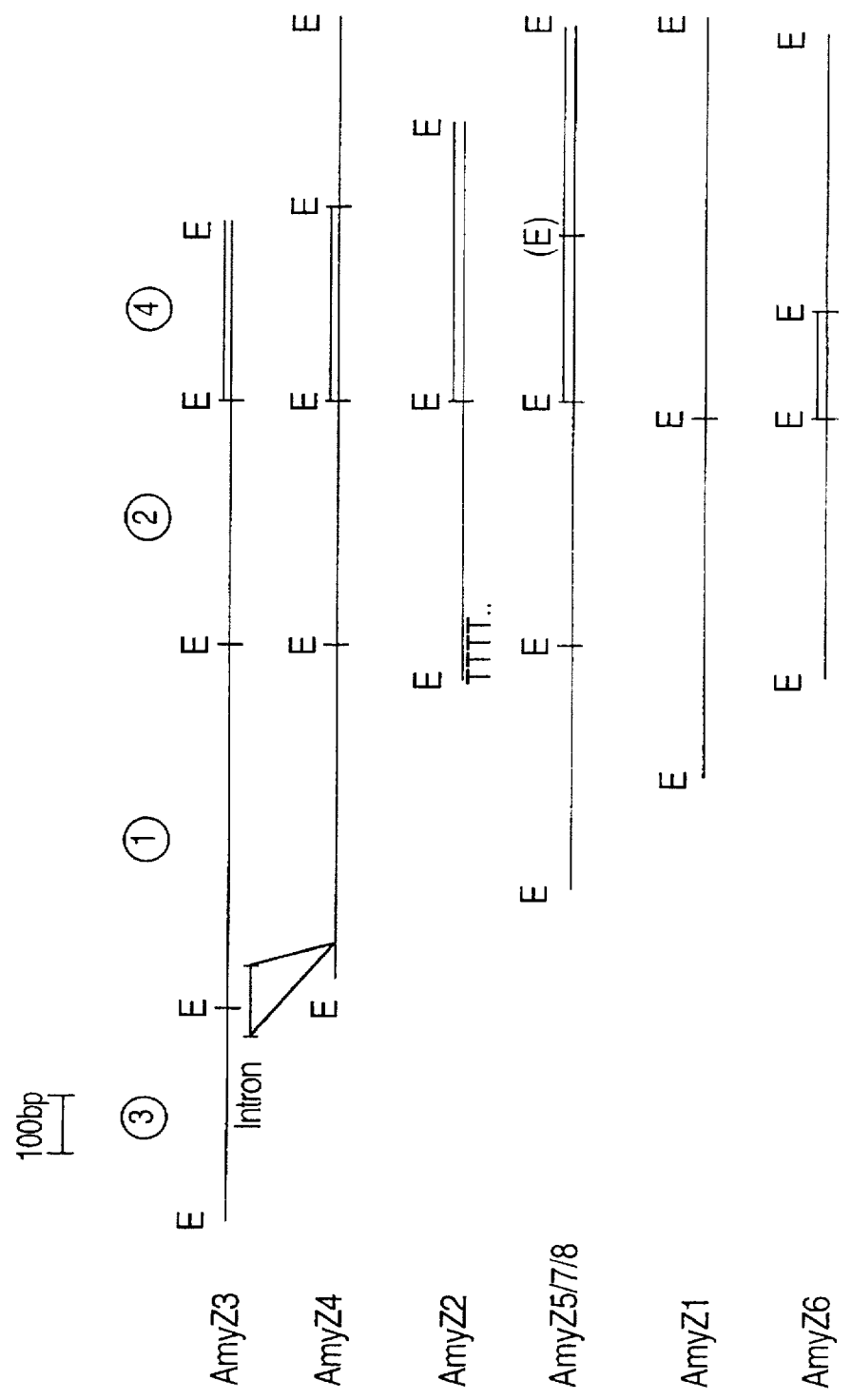
FIG. 10 shows Eco RI maps of potato α-amylase cDNA clones.
Figure 19:
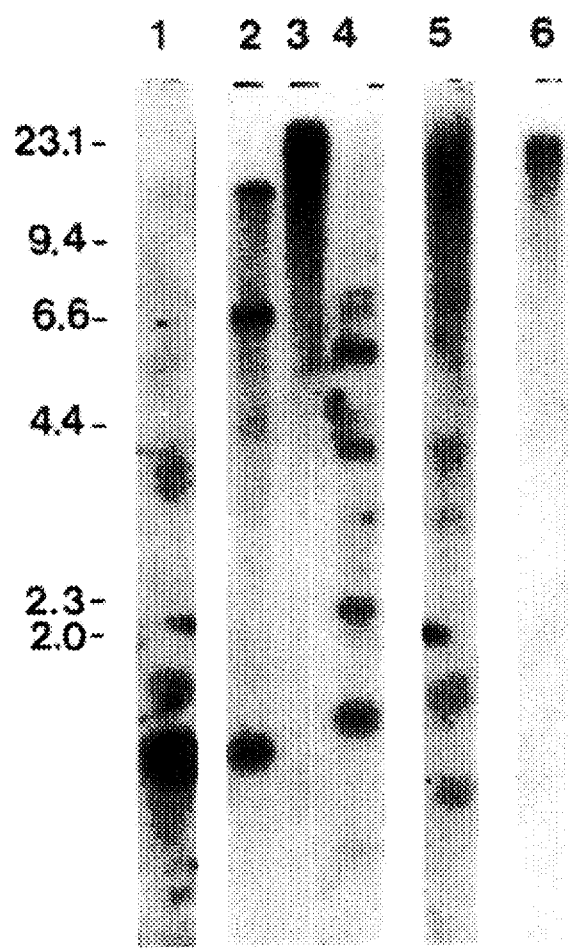
FIG. 19 shows Southern hybridizations of Saturna potato genomic DNA with potato α-amylase probes from AmyZ3.

FIG. 10 shows EcoRI maps of potato α-amylase cDNA clones. All maps have been refined after DNA sequence determination. In the maps of the clones only the EcoRI sites are shown and the terminal EcoRI sites are in the EcoRI linkers by which the inserts were inserted into the EcoRI site in the vector, pBluescript SK-. The sequences of the inserts of AmyZ5, 7, and 8 are completely identical. The EcoRI fragments that hybridize to the barley α-amylase probe are indicated with an extra thin line. In FIG. 9 weak bands, 285 base pairs long, that gave rise to these bands is shown in parentheses. The circled number above the figure indicates the EcoRI fragments used in Southern and Northern hybridizations (FIGS. 19 and 21, respectively). The clone AmyZ2 includes a row of 76 unstable T residues that is the result of a common cloning artefact.

Figure 11:
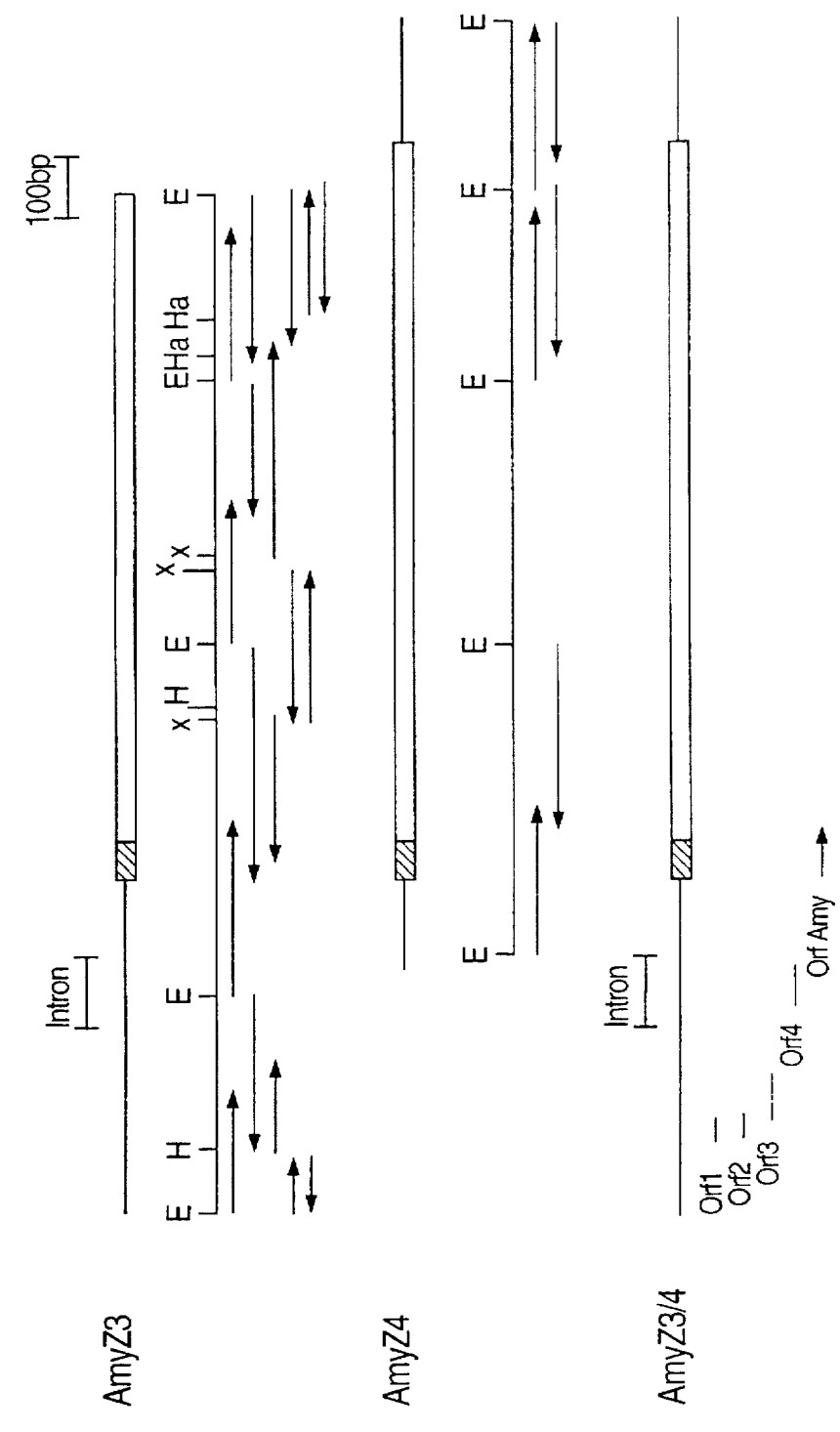
FIG. 11 shows the strategy for sequencing the inserts of plasmids AmyZ3 and AmyZ4 and a summary map of AmyZ3/4.

FIG. 11 shows the strategy for sequencing the inserts of plasmids AmyZ3 and AmyZ4 and a summary map of AmyZ3/4. The arrows show the direction and length of sequences obtained in individual sequence analyses. The abbreviations for the restriction enzyme sites are E=EcoRI, H=HindIII, Ha=HaeIII, X=XhoII. Above the maps, the location of the α-amylase precursor open reading frame is shown with boxes, the striped portions indicating the signal peptides and the white portions the mature α-amylase. In the combined map of AmyZ3 and 4 the location of the open reading frames in the 5' leader sequence is indicated; they are shown in more detail in FIG. 17.

Figure 12:
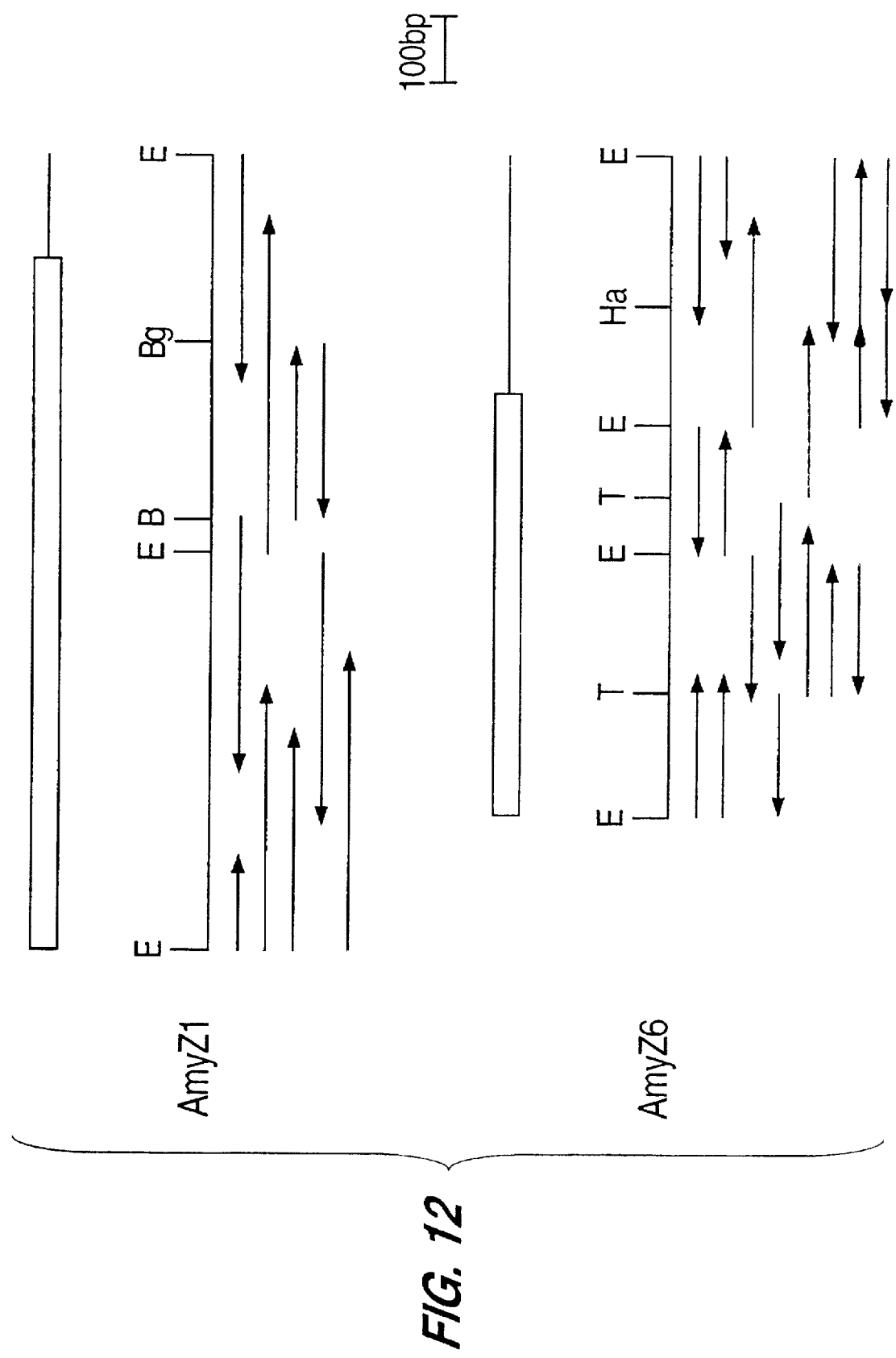
FIG. 12 shows the strategy for sequencing the inserts of plasmids AmyZ1 and AmyZ6.

FIG. 12 shows the strategy for sequencing the inserts of plasmids AmyZ1 and AmyZ6. The arrows show the direction and length of sequences obtained in individual sequence analyses. The abbreviations for the restriction enzyme sites are E=EcoRI, H=HindIII, B=BamHI, Bg=BglII, Ha=HaeIII, T=Taq. Above the maps, the location of the α-amylase open reading frame is shown with boxes.

Figure 13:
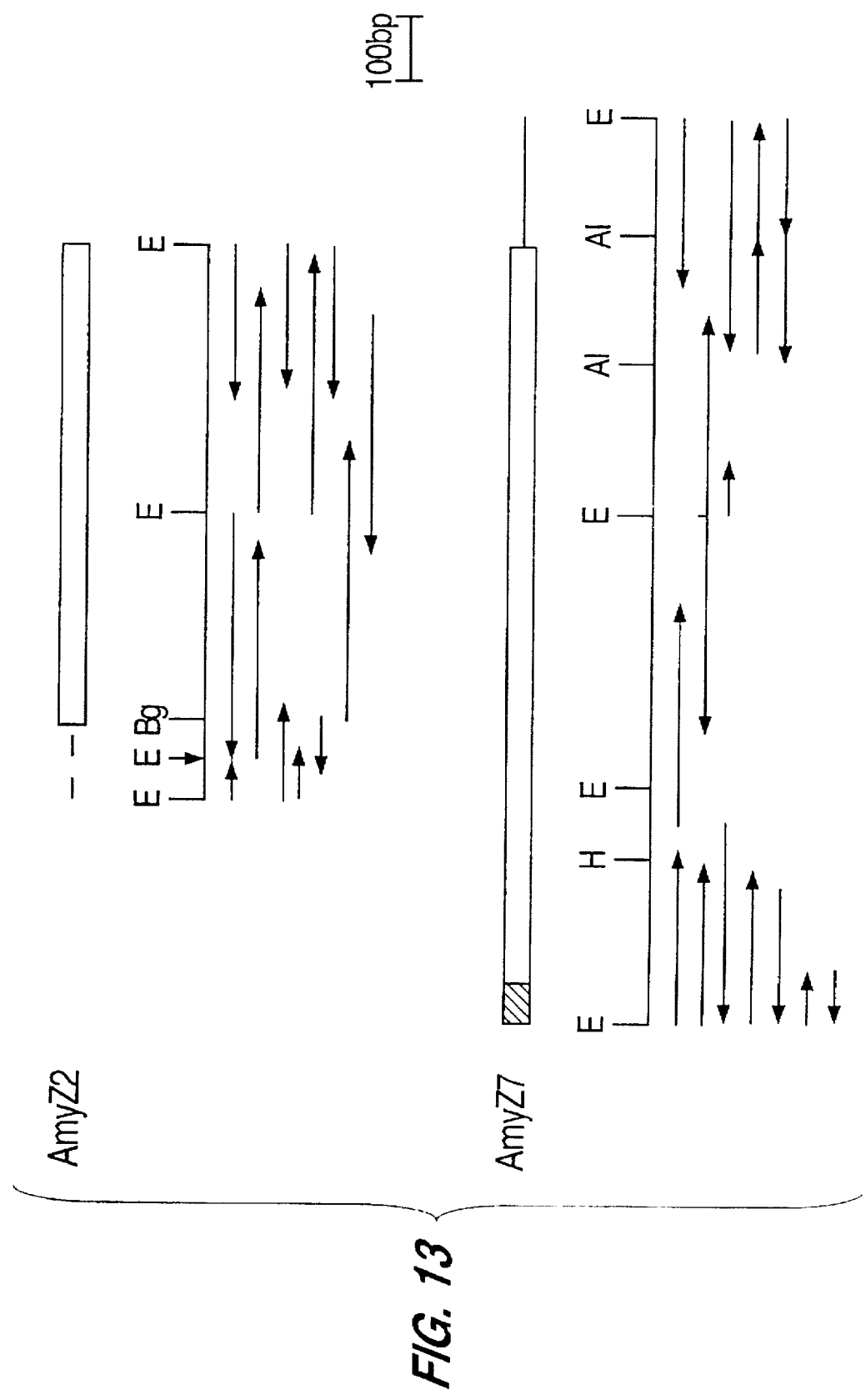
FIG. 13 shows the strategy for sequencing the inserts of plasmids AmyZ2 and AmyZ7.

FIG. 13 shows the strategy for sequencing the inserts of plasmids AmyZ2 and AmyZ7. The arrows show the direction and length of sequences obtained in individual sequence analyses. The insert in plasmid AmyZ2 has a string of 76 T residues at the left end that is the result of a common cloning artefact. In subclones used for sequence determination a portion of the Ts were deleted and this event is indicated by the arrow. The abbreviations for the restriction enzyme sites are A1=AluI, E=EcoRI, H=HindIII, Bg=BglII. Above the maps, the location of the α-amylase open reading frame is shown with boxes.

FIG. 14 shows the homology between potato and barley α-amylase encoding nucleotide sequences. The top lines show the sequence of the EcoRI fragment from AmyZ4 that hybridizes with the barley SacI probe (FIG. 7) as shown in FIG. 9. The potato sequence is aligned with the corresponding region from the SacI probe (U=Uracil replaces T, when a sequence is written as RNA). The total homology between the sequences is 63.5% (unmatched nucleotides are included in the total length). A region of 146 nucleotides with a homology of 73% is boxed, and within this region is shown a smaller box of 46 nucleotides with 80% homology.

Figure 15B:
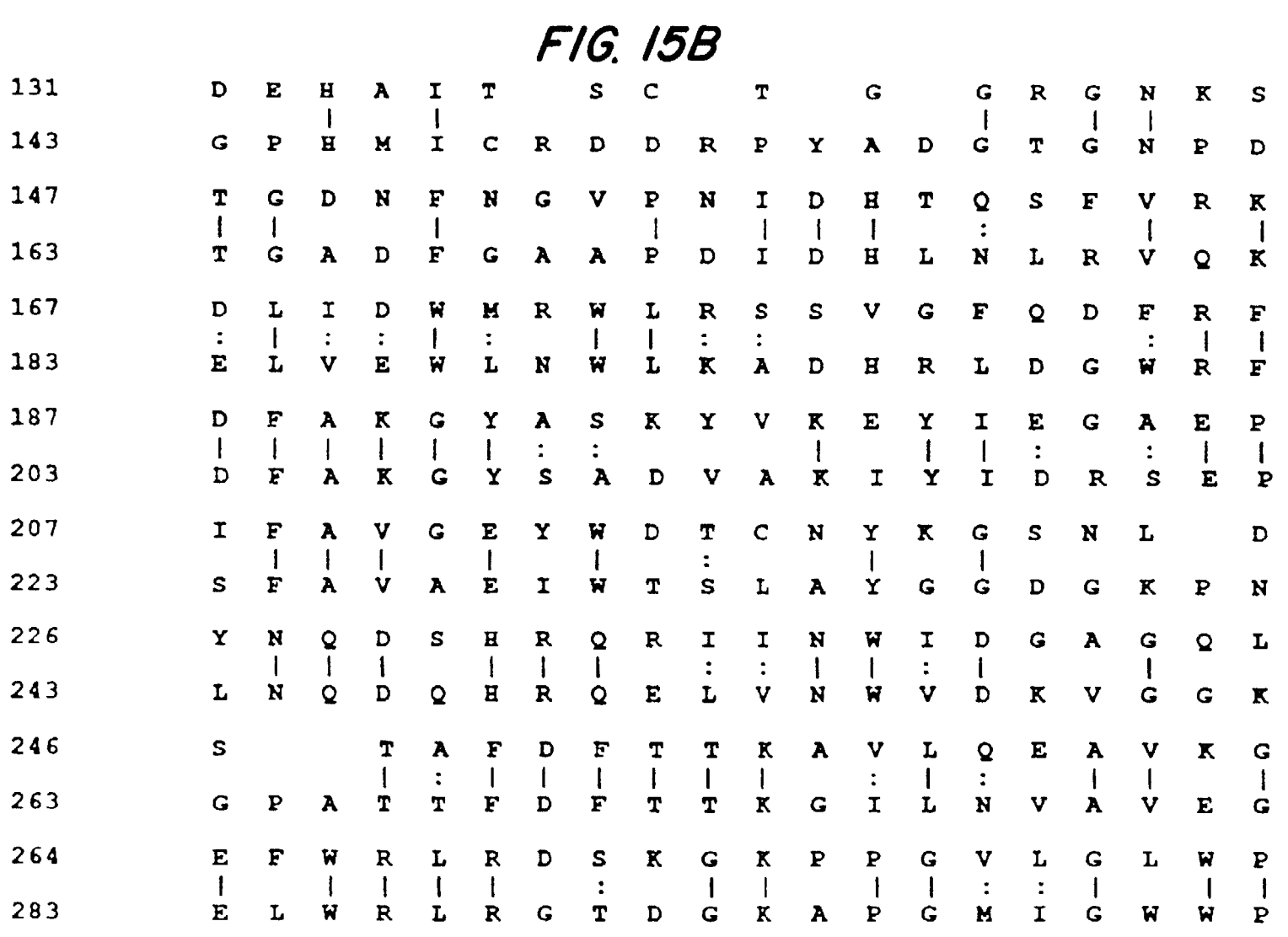
Figure 15C:
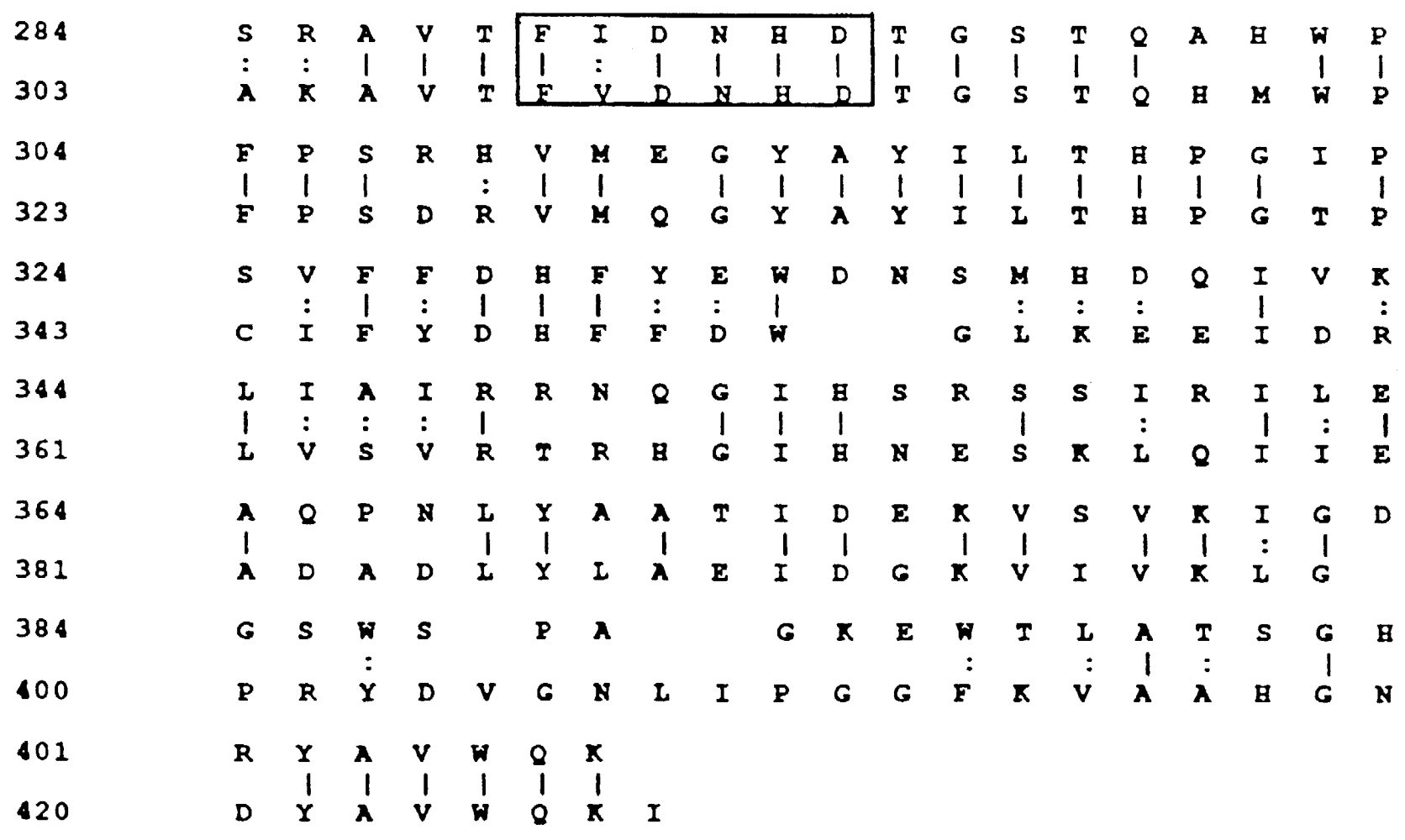

FIG. 15 shows the homology between potato AmyZ3/4 α-amylase and barley α-amylases. The figure shows the amino acid sequences of mature potato α-amylase from FIG. 1 (top lines) and mature barley amylase B, decoded from pM/C (bottom lines) (24). Identical amino acids are indicated by a dash and conserved amino acids by double dots. Gaps have been introduced to maximize the similarity. The percentage of identical amino acids is 45.6 (unmatched amino acids are included in the total length). The box indicates a peptide which is conserved in α-amylases found in mammals and insects.

FIG. 16 shows the homology between potato AmyZ1 α-amylase and barley α-amylase. The figure shows the partial amino acid sequence of mature potato α-amylase, bottom lines (from FIG. 3), and mature barley amylase B, decoded from pM/C, top lines (24). Identical amino acids are indicated by double dots and conserved amino acids by single dots. On gap has been introduced to maximize the similarity. The percentage of identical amino acids is 64.1 (the unmatched amino acid is included in the total length).

FIG. 17 shows open reading frames in the 5' end of the AmyZ3 sequence. The extent of the open reading frames and their frames are shown at the top, the amino acid sequences at the bottom. The position of the intron in AmyZ3 is also indicated.

Figure 18:
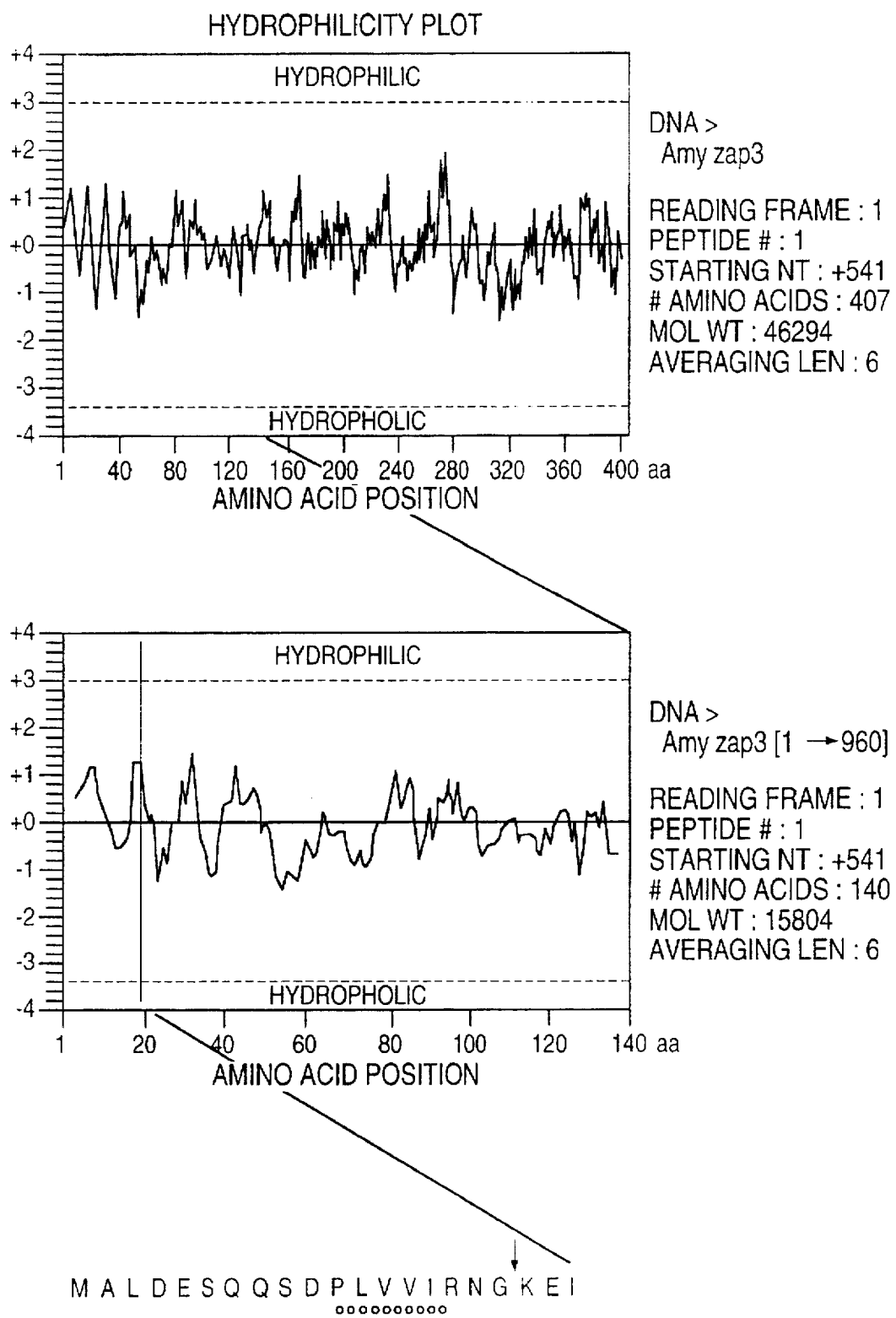
FIG. 18 shows the hydrophilicity profile of the potato α-amylase precursor with the amino acid sequence shown in FIG. 1.

FIG. 18 shows a hydrophilicity profile of potato α-amylase precursor with the amino acid sequence shown in FIG. 1. The analysis was performed by the method of Hopp and Woods (25). Part of the plot is expanded to illustrate the short hydrophobic region of the signal peptide. At the bottom the amino acids contributing to the hydrophobic stretch are indicated by small circles and the probable processing site by an arrow.

FIG. 19 shows Southern hybridizations of potato genomic DNA with potato α-amylase probes. Saturna DNA was digested with restriction enzymes and fractionated on an 8% agarose gel. The DNA fragments were transferred to nitrocellulose filters and the filters hybridized at medium high stringency with nick-translated EcoRI fragments from AmyZ3. The figure shows the resulting autoradiograms. Lanes 1 and 2 contain HindIII digested DNA, lane 3 contains BamHI digested DNA, and lanes 4 and 5 contain EcoRI digested DNA. Lane 6 is a weaker exposure of lane 3. The central lanes 2, 3, and 4 were hybridized with nick-translated EcoRI fragments 2, 3, and 4 from AmyZ3, and lanes 1 and 5 were hybridized with nick-translated EcoRI fragment 1 (FIG. 10). The numbers on the left are size markers in kbp from ethidium bromide stained HindIII fragments of phage λ DNA.

Figure 20A:
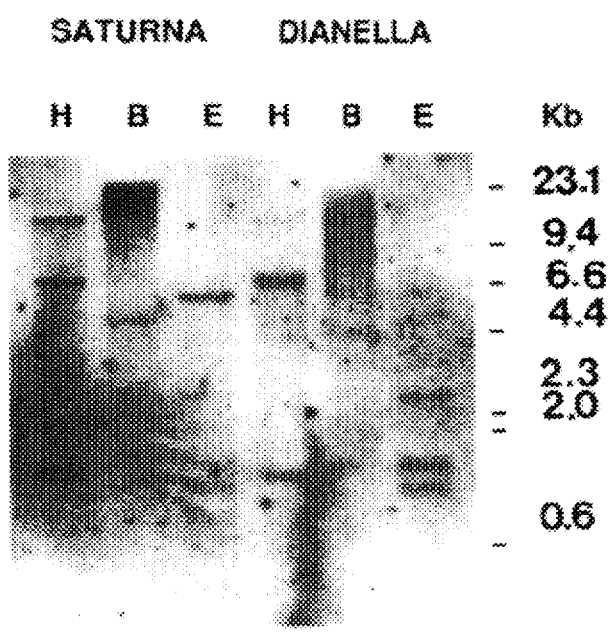
FIGS. 20(a) and 20(b) show Southern hybridizations of Saturna and Dianella potato genomic DNA with potato α-amylase probes from AmyZ3/4 and AmyZ1.
Figure 20B:
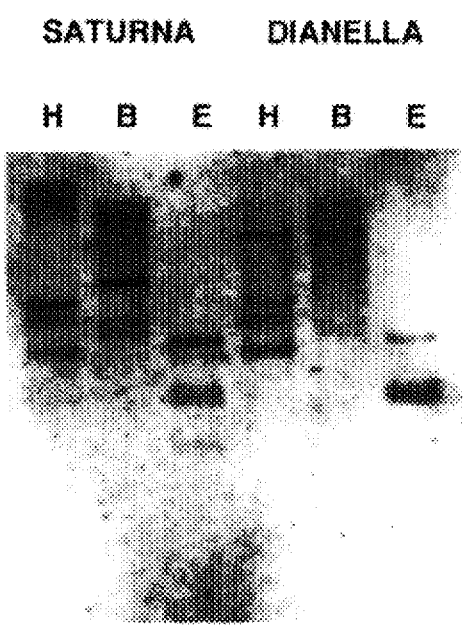

FIG. 20 shows Southern hybridizations of two varieties of potatoes with AmyZ3/4 and AmyZ1 types of α-amylase probes. The method used is described in FIG. 19. The left hand autoradiogram shows hybridization of the complete α-amylase insert from plasmid AmyZ3 to Saturna and Dianella potato variety genomic DNA. The right hand autoradiogram shows hybridization of the complete α-amylase insert from plasmid AmyZ6 to Saturna and Dianella potato variety genomic DNA. Abbreviations for restriction enzymes: H=HindIII, B=BamHI, E=EcoRI. Numbers in the middle are size markers in kbp from ethidium bromide stained HindIII fragments of phage λ DNA.

FIG. 21 shows northern hybridization of potato RNA. RNA from sprouts and tubers from varieties Saturna and Dianella was fractionated on agarose gels after denaturation and control lanes which also contained potato RNA were stained with methylene blue to visualize the ribosomal RNAs. Their migration is indicated by thin arrows; the top arrows show 26s RNA (approximately 4400 nucleotides) and the bottom arrows show 18s RNA (approximately 1850 nucleotides). The RNA in the remaining lanes were transferred to nitrocellulose filters which were hybridized with potato α-amylase specific probes and used to expose X-ray films. Saturna sprout RNA was hybridized to nick-translated EcoRI fragment 1 from AmyZ3 (FIG. 10); the three other RNAs were hybridized to nick-translated EcoRI fragments 2, 3 and 4 from AmyZ3. Dianella sprout RNA was the polyA-rich fraction used for construction of the cDNA library, whereas the three other lanes contained total RNA. Thick arrows mark the position of α-amylase specific bands seen in the original autoradiogram, and their approximate sizes are listed in the table in Example 17.

Figure 22:
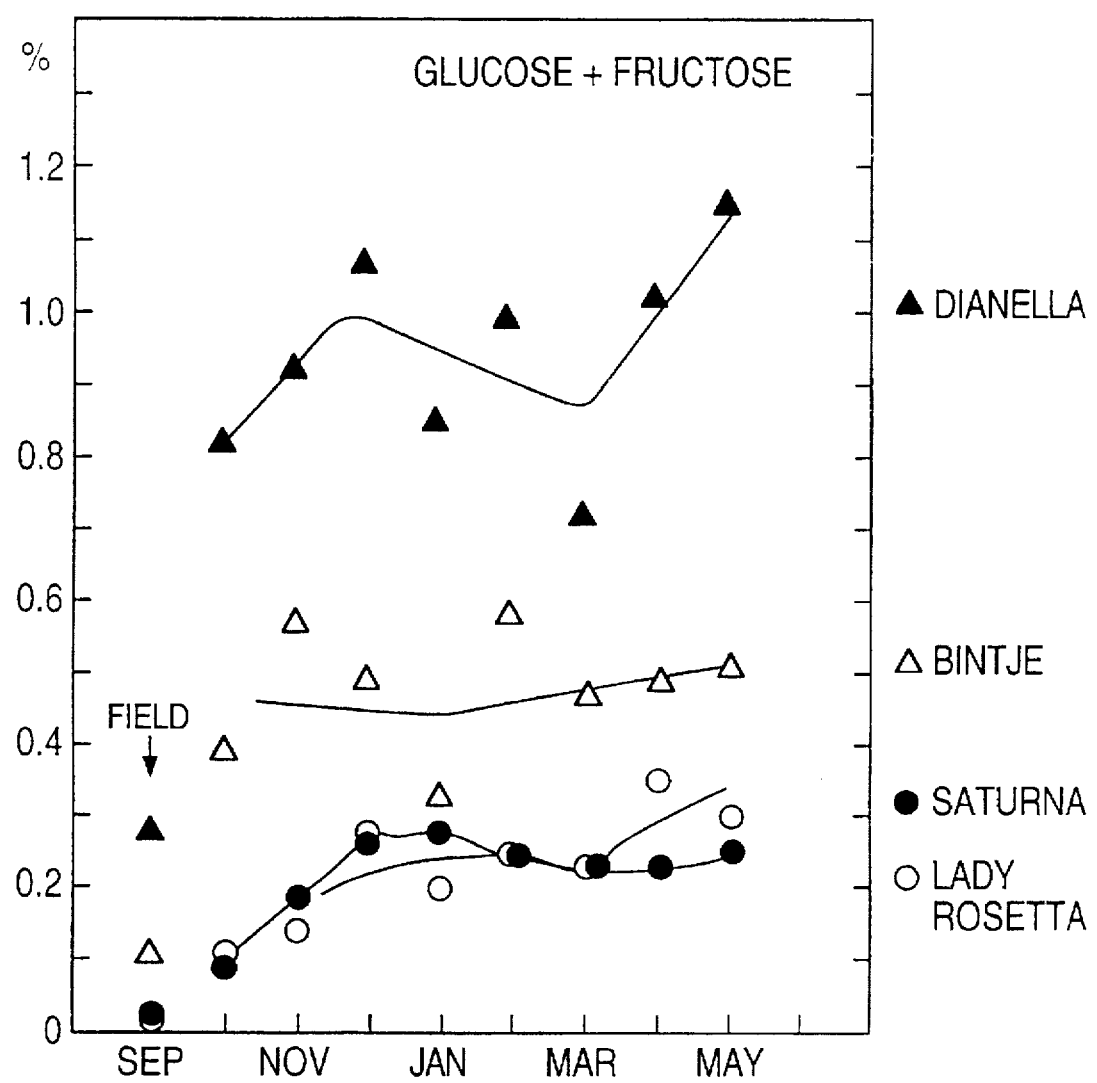
FIG. 22 shows reducing sugar levels in four varieties of potatoes stored at 8° C.

FIG. 22 shows reducing sugar levels in stored potatoes. The levels of glucose and fructose (including the phosphorylated forms) were determined in four varieties of potato at the time of harvest and during subsequent long term storage at 8° C. The figure shows the sum of the glucose and fructose levels.

Figure 23:
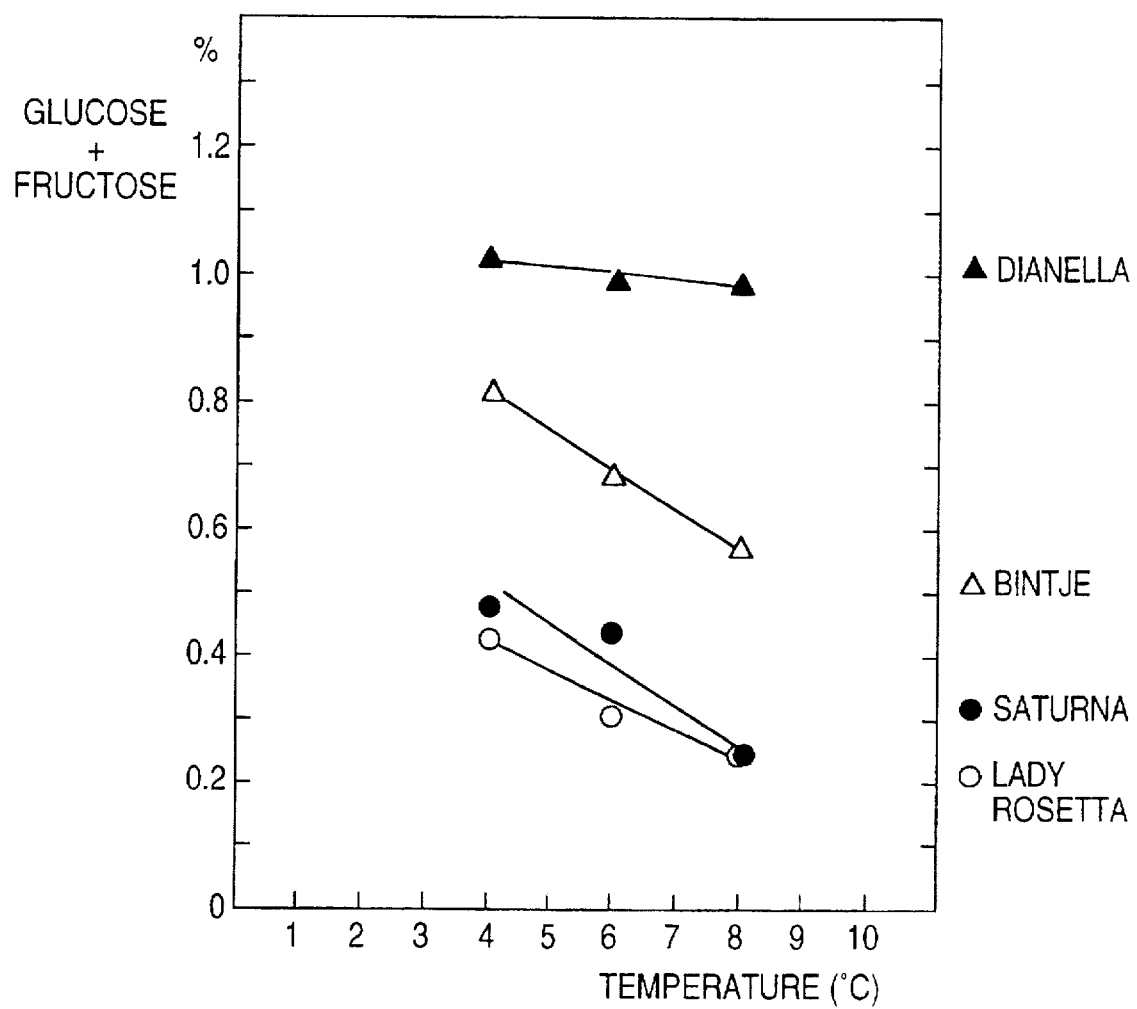
FIG. 23 shows reducing sugar levels in four varieties of potatoes stored at 4° C., 6° C., or 8° C.

FIG. 23 shows reducing sugar levels at different storage temperatures. The levels of glucose and fructose (including the phosphorylated forms) were determined in four varieties of potato stored for 19 weeks at 8° C. or 6° C., and 6 weeks at 4° C. All potatoes were sampled on the same day. The figure shows the sum of the glucose and fructose levels.

Figure 24:
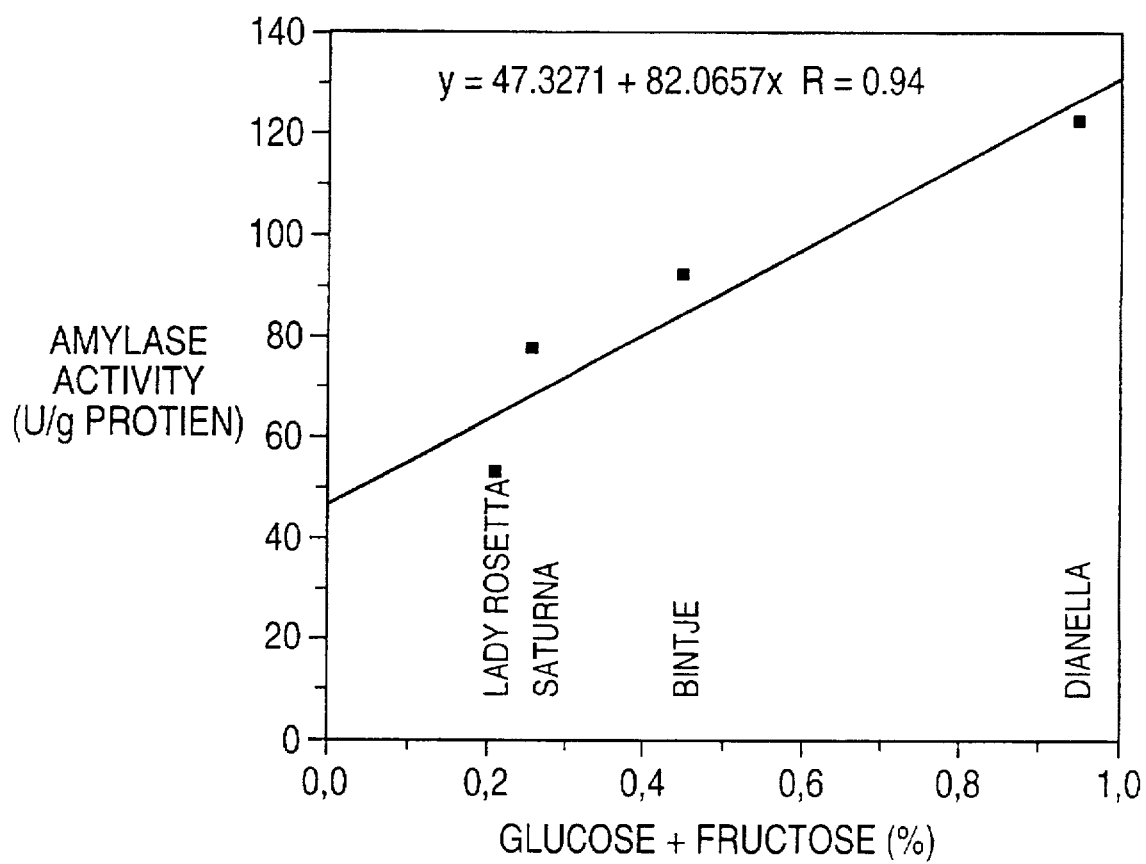
FIG. 24 shows levels of α-amylase activity in juice of four varieties of potatoes stored at 6° C. or 8° C.

FIG. 24 shows levels of α-amylase in stored potatoes. The activity of α-amylase was determined (method 2) in the juice of four varieties of potatoes stored for 19 weeks at 8° C. and at 6° C. The figure shows the average values obtained at the two temperatures as a function of the level of the reducing sugars at 8° C. after 19 weeks of storage.

MATERIALS AND METHODS
Potato varieties

The following potato varieties were used: Dianella, Saturna, Bintje, Lady Rosetta.

These potato varieties were chosen in order to illustrate the relation between reducing sugar and α-amylase activity and to identify the variety and/or tissue, from which α-amylase clones could be isolated in the most advantageous manner.

Dianella is a variety used as a starting material for alcohol fermentation, due to its high content of starch. Dianella was chosen because it is a well-known variety and because it probably represents an extremity as regards sugar metabolism in potatoes generally.

Saturna is known for its low content of reducing sugars, making it particularly suitable for use in the production of e.g. potato chips. It is one of the few potato varieties with a sugar content low enough to make it suitable for producing potato chips after prolonged storage. However, it is a relatively sensitive variety with respect to cultivation, especially with regard to its demand for water. It is therefore desirable that new potato varieties with a low reducing sugar content equivalent to that of Saturna may be produced.

Bintje is a well-known established variety which is primarily used for potatoes intended for normal consumption. Its content of reducing sugars lies between that of Dianella and Saturna.

Lady Rosetta is a new variety for use in the production of e.g. potato chips. It is one of the few potato varieties with a reducing sugar content low enough for use in the production of chips, but it is still in the experimental stage.

Bacterial strains

HB101: hsm, hrs, recA, gal, pro stz$^R$

JM109: recA1, endA1, gyrA96, thi, hsd R17, supE44, relA1, λ$^-$, Δ(lac$^-$proAB), [F', traD36, proAB, LacI$^q$ZΔM15]

XL1-Blue: endA1, hsdR17 ($r_k^-$, $m_k^+$), supE44, thi-1, λ$^-$, recA1, gyrA96, relA1, Δ(lac), [F', proAB, lacI$^q$ ZΔM15, Tn10 (tet$^R$)]

BB4 recA$^+$, lacI$^q$, ZΔM15, tet$^R$

JM109: see reference (48)

XL1: see reference (20, 49)

BB4: see reference (31)

HB101: see reference (50)

Phages and plasmids

λZap: see reference (31)

R408 Interference Resistant Helper Phage: see reference (31)

pBR327: see reference (51)

pBS+, pBS−: see reference (31)

Medium and places

L-Broth (LB) medium:

Per liter: 5 g of yeast extract, 5 g of NZ-amide, 5 g of NaCl, 5 g of bacto-peptone. Autoclave.

LB-plates:

LB medium plus 15 g of Bacto agar per liter. Autoclave. Pour into plastic petri dishes (25 ml/dish).

Tet-plates:

As LB-plates plus 17 mg tetracycline per liter after autoclaving.

Amp-plates:

As LB-plates plus 35 mg ampicillin per liter after autoclaving.

AXI-plates:

As LB-plates plus 35 mg ampicillin, 120 mg IPTG (isopropylthiogalactoside), 40 mg Xgal (dissolved in dimethylformamide) per liter after autoclaving.

Xgal: 5-bromo-4chloro-3indolyle-β-D-galactoside.

Minimal medium: 400 ml of $H_2O$, 1 ml of solution B, 100 ml of solution A, 5 ml (0.5 mg/ml) of thiamin, 5 ml of 20% glycerol. Solution A is 10 g of $(NH_4)_2SO_4$, 24 g of $Na_2HPO_4$, 15 g of $KH_2PO_4$, 15 g of NaCl per liter of $H_2O$. Solution B is 200 g of $MgCl_2.2H_2O$, 7.2 g $CaCl_2.2H_2O$ and 20 ml of micronutrient solution per liter. Micronutrient solution is 10 µM $FeCl_2$, 500 nM of $CaCl_2.2H_2O$, 400 nM of $H_3BO_3$, 80 nN of $MnCl_2$, 30 nM $CoCl_2$, 10 nM $CuCl_2$, 3 nM of $(NH_4)_6Mo_7O_{24}$. For plates add 15 g of agar per liter autoclave.

Freezing of potato samples

In order to be able to measure amylase activity, the potato samples were first frozen. A metal bucket was filled ⅔ full with liquid $N_2$, and a plastic bowl filled halfway up with the potato material was placed in the bucket with liquid $N_2$. A blender bowl which had been cooled with liquid $N_2$ was filled with the cooled potato material, and 2 teaspoons of ascorbic acid were added. The material was blended in a blender until the potato material had a flour-like consistency. An 800 ml beaker was cooled with liquid $N_2$ and a potato sample was poured into the beaker. Each sample was divided into 2 portions which were placed in 2 plastic bags, and the bags were placed in a freezer as quickly as possible. This frozen potato material is referred to in the following as "pretreated material".

Determination of reducing sugar levels in potatoes 25 g of the above pretreated material was weighed and ice-water was added to 125 ml. The mixture was blended for 1 min. and then centrifuged for 10 min. at a temperature of 0° C. and 14,000 rpm. The supernatant was decanted from the precipitate and filtered through a sterile filter, heated in a water bath for 10 min., and filtered again through a sterile filter. Determination of levels of D-glucose before and after enzyme hydrolysis of sucrose, and determination of D-fructose after the determination of D-glucose, were carried out using a sucrose/D-glucose/D-fructose test kit from Boehringer Mannheim according to the manufacturer's instructions.

Qualitative measurement of amylase activity in potato

Potato tubers (varieties Saturna and Dianella) were placed in a dark cupboard for 14 days at 20° C.

Tissue extracts of these tubers and their white sprouts were prepared by grinding 2 g of fresh tissue (or in some cases 10 g of frozen tissue) with 5 ml of 0.1M Tris.HCl (pH 6.2), 1 mM $CaCl_2.6H_2O$. The homogenate was centrifuged for 5 min at 10,000 rpm and 4° C. in 15 ml corex tubes. 5 µl of the supernatant was spotted on a glass plate covered with a thin film of 1% starch (w/v). The glass plate (with the thin film facing up) was placed in a petri dish on 4 pieces of pre-wetted filter paper. Care was taken to ensure that the starch plate was held moist under the incubation, so that the enzyme could function adequately. The petri dish was incubated at either 20° C. or 37° C. for 16 h. The starch plates were submerged in $I_2$/kI solution and rinsed under deionized water. The $I_2$/kI solution gives the starch a dark blue colour, which disappears if the starch has been digested to glucose and maltose (a "strong" reaction). In cases where there is a "weak" reaction, the spot is reddish, with a clear change in the surface compared to the surroundings (more smooth) (7).

Quantitative Determination of α-amylase activity (method 2)

The following procedure was used for each sample of pretreated potato material. All determinations were carried out in duplicate, with 4 samples and 8 determinations from each sample of pretreated potato material.

A 75 ml beaker was filled with the above pretreated material and sealed with parafilm. The material was allowed to thaw in the beaker, optionally in a water bath. After thawing, the liquid was poured into a centrifuge test tube and centrifuged at 14,000 rpm for 10 min. 10 ml of buffer with a pH of 5.5 was added to an Erlenmeyer flask with a 10 ml pipette, after which a tablet comprising Phadabas blue starch powder (Pharmacia Diagnostics Ltd.) was added to the buffer. The tablet was dissolved by gently shaking the flask. Finally, 5 ml of supernatant from the centrifuged liquid was added to the solution with a 5 ml pipette, being careful not to disturb the precipitate. Penicillin was added to the flask to achieve an activity of 10,000 I.U., and the flask was sealed with parafilm.

The flasks were placed in a 45° C. water bath for 48 hours, after which they were cooled in a tub with cold water. The optical density of the samples were measured with a spectrophotometer at 620 nm using a buffer with a pH of 5.5 as a blind sample. The concentration of α-amylase in the samples was calculated automatically on the basis of these measurements.

The protein concentration was determined in the supernatants according to Lowry (52)

Harvest of potato tissue for RNA/DNA isolation

Tubers (Dianella, Saturna) were placed in a dark cupboard at 20° C. The white sprouts which developed were harvested after 14 days and cut into smaller pieces. The tissue was frozen with dry ice immediately after cutting and stored at −80° C. until use. Tubers (Dianella, Saturna, Bintje, Lady Rosetta) were peeled, grated (with a grater) directly onto tin foil placed on dry ice. 10 g portions were stored at −80° C. until use.

Extraction of RNA from potato sprouts

Total RNA was extracted and purified from potato (*Solanum tuberosum*, Dianella and Saturna varieties) white sprouts after grinding under liquid $N_2$, using the following guanidine thiocyanate/N-sarcosine method of Kaplan et al. (8).

10 g of frozen sliced potato sprouts were homogenized in 6 vol. (w/v) of 5.0M guanidine thiocyanate, 50 nM Tris-HCl (pH 7.5), 10 mM. EDTA and 5% 2-mercaptoethanol. The homogenate was made 4% (w/v) with respect to N-lauroylsarcosine and solid CsCl was added to 0.15 g/ml. The homogenate was centrifuged for 20 minutes at 10,000 rpm, 4° C. to remove debris. The supernatant was gently layered over a 2.5 ml cushion of 5.7M CsCl, 0.1M EDTA and centrifuged in a Beckman SW-41 rotor at 37,000 rpm for 18 hours at 20° C. After centrifugation, the homogenate was carefully removed with a pasteur pipette and the polyallomer tubes were washed three times with water. After removal of the CsCl cushion, the RNA pellets were suspended in 10 mM Tris-HCl (pH 7.5) and precipitated by the addition of 2.5 vol. of cold ethanol.

The pellet was resuspended in 10 mM Tris-HCl, adjusted to 100 mM NaCl and precipitated with 2.5 vol. cold ethanol. The final RNA pellet was suspended in 10 mM Tris-HCl (pH 7.5) 2 mM EDTA, 100 mM NaCl and the RNA concentration was determined by measuring $OD_{260}$ (OD=1 for a solution with 40 µg RNA/ml).

The total RNA used for the isolation of polyA-rich RNA was suspended in 10 mM Tris-HCl (pH 7.5), 2 mM EDTA, 100 mM NaCl and 0.5% sodium dodecyl sulphate (SDS).

Extraction of RNA from tubers

It was not possible to isolate RNA from tuber tissue using the above explained conventional method, i.e. with the guanidine thiocyanate/N-sarcosine method. The guanidine thiocyanate reacted with the starch and the products had a jelly-like consistency. From this turbid liquid it was impossible to centrifuge the RNA through the CsCl cushion. Thus, the present inventors had to develop another method: the tuber tissue ground under liquid $N_2$ was suspended in 10 mM Tris-HCl (pH 7.5), 50 mM EDTA, 500 mM NaCl, 5% 2-mercaptoethanol, 1% SDS and placed at 65° C. for 20 min. The homogenate was made 3% (w/v) with respect to N-lauroylsarcosine and solid CsCl was added to 0.15 g/ml. The homogenate was centrifugated for 20 min at 10,000 rpm, 4° C. (International) to remove debris. The RNA was then isolated by centrifugation over a CsCl cushion as described above (9).

RNA electrophoresis

The RNA samples were denatured in 0.5M glyoxal (deionized, stored at −20° C.), 10 mM $Na_2HPO_4/NaH_2PO_4$ (pH 6.5), 50% DMSO (dimethylsulfoxide, stored at 4° C.) (10). They were then incubated at 50° C. for 1 hour and placed for 5 to 10 minutes on ice before adding tracking dye (35% ficoll, MW 400,000, 0.01M $Na_2HPO_4/NaH_2PO_4$ (pH 6.5), 0.4% Bromophenol Blue. The samples were loaded onto a 1.5% agarose gel in 10 mM $Na_2HPO_4/Na_2PO_4$ (pH 6.5) and subjected to electrophoresis in the presence of 10 mM $Na_2HPO_4/NaH_2PO_4$ (pH 6.5) with buffer recirculation, at 35 mA for approximately 2 ½ hours (11). One or two lanes were cut from the gel and the RNA was stained overnight in Methylene Blue solution (33.5 ml 3M Na-acetate, 100 ml 1M acetic acid, $H_2O$ up to 500 ml and 10 mg Methylene Blue).

Northern blotting

A glass plate was placed in a trough on a support that lifted the glass plate 5–6 cm. A piece of filter paper, wetted in 0.025M $Na_2HPO_4/NaH_2PO_4$ (pH 6.5), was placed on the glass plate with the ends and sides touching the bottom of the trough.

0.025M $Na_2HPO_4/NaH_2PO_4$ (pH 6.5) was poured into the trough so that the surface barely touched the glass plate, and the RNA gel was placed on top of the wet filter paper. A Gene Screen (New England Nuclear) membrane was cur to the exact size of the gel, soaked in 0.025M $Na_2HPO_4/NaH_2PO_4$ (pH 6.5) and placed on top of the gel (avoiding trapping air bubbles). Four pieces of parafilm covered the edges of the membrane and a piece of filter paper wetted in 0.025 $Na_2HPO_4/NaH_2PO_4$ (pH 6.5) was placed on top of it. Several pieces (20–25) of filter paper were layered on top, and on top of these were layered several paper towels (6–8 cm). The filter paper and paper towels were cut to the size of the gel. A glass plate and a weight were placed on top of the paper towels. The transfer took place over a period of 16 hours. The paper towels, filter paper and parafilm were removed. The membrane was marked for size markers (18S rRNA and 28S rRNA) using the piece of gel stained in Methylene Blue overnight. The membrane was washed in 0.025M $Na_2HPO_4/NaH_2PO_4$ (pH 6.5) air dried and baked for 2 h. at 80° C. (11).

Hybridization of RNA

The Gene Screen membrane was prewetted in 6×SSC for 30 minutes at room temperature with constant agitation. Then the membrane was prehybridized in a solution of 50% formamide (deionized), 0.2% polyvinyl-pyrrolidone (MW 40,000), 0.2% bovine serum albumin, 0.2% ficoll (NW 400,000), 0.05M Tris-HCl (pH 7.5), 1.0M NaCl, 0.1% $Na_4P_2O_7$, 1.0% SDS, 10% dextran sulphate (MW 500,000), denatured sonicated salmon sperm DNA (50 μg/ml) and 10 μg/ml polyA RNA. The volume of the prehybridization solution was 100 μl/cm$^2$ of the membrane placed in a sealable plastic bag. Prehybridization took place in a sealed plastic bag which was incubated for 6 hours at 42° C. with constant agitation. To the bag was added ⅕ of its liquid volume of the following solution: 50% formamide (deionized), 0.2% polyvinyl-pyrrolidone (MW 40,000), 0.2% bovine serum albumin, 0.2% ficoll (MW 400,000), 0.05M Tris-HCl (pH 7.5), 0.1% $Na_4P_2O_7$, 1.0% SDS, denatured sonicated salmon sperm DNA (50 μg/ml), poly A (10 μg/ml) and the denatured radioactive probe (5 ng/ml prehybridization and hybridization solution). The bag was resealed and incubated with constant agitation for 16–20 hours at 42° C. The hybridization solution was removed and the membrane was washed at room temperature in 2×SSC, 1 mM EDTA, 10 mM Tris-HCl, pH 7.59 2×5 min., at 67° C. in 2×SSC, 10% SDS, 1×10 min and 1×30 min., and finally at room temperature in 0.1×SSC, 1×5 min. and 1×30 min., always with constant agitation (11). The membrane was air dried, covered with plastic film and autoradiographed with and without intensifying screen at −80° C. The salmon sperm DNA and the radioactive probe were denatured by boiling for 10 min. in a water bath and placed on ice before being added to the hybridization solution.

Isolation of poly(A)-rich RNA

An oligo(dT) column was made as follows 2 g oligo(dT)-cellulose/Type 2 (purchased from Collaborative Research, Inc., Research Product Division, 1365 Main Street, Waltham, Mass., USA) was washed once with 10 nM Tris-HCl (pH 7.5), washed once with 0.5M KOH and neutralized by 8–10 washes with 10 mM Tris-HCl (pH 7.5). The column was poured and preserved at room temperature in 1% SDS. The column was run at 30° C. and the buffers were warmed to 30° C. before use. The 1% SDS was removed by passing 2 vol. 10 mM Tris-HCl (pH 7.5) over the column. Before adding the RNA sample the column was adjusted to high salt buffer by passing 2 vol. 10 mM Tris-HCl (pH 7.5), 500 mM NaCl over it. The total RNA dissolved in 2 mM EDTA, 10 mM Tris-HCl (pH 7.5), 100 mM NaCl and 0.5% SDS was heated to 65° C. for 10 minutes (to remove aggregations), cooled to 30° C. and adjusted to 500 mM NaCl. The solution was then gently applied to the top of the column and the column was washed with 10 mM Tris-HCl (pH 7.5), 500 mM NaCl until the $OD_{260}$ of the eluent was less than 0.01. The enriched poly(A)RNA was eluted with 10 mM Tris-HCl (pH 7.5), and 10 fractions of 1 ml were collected. The poly(A)-rich RNA was precipitated from the peak fractions (measuring $OD_{260}$) by adjusting to 100 mM NaCl and adding 2.5 vol. cold ethanol. The RNA was centrifuged at 10,000 rpm for 20 minutes at 4° C. (Sorvall cooling centrifuge) and dried under vacuum. The dry pellet was suspended in sterile water (1 μg poly(A)-rich RNA/μl) kept on ice and stored at −20° C. (12).

Isolation of genomic DNA

Genomic DNA was isolated from white potato sprouts. 10 g of frozen sliced potato sprouts was ground under liquid $N_2$ and homogenized in 4 vol. (w/v) proteinase K buffer (10 mM Tris-HCl (pH 7.5), 100 mM NaCl, 5 mM EDTA, 1% SDS and 0.2 mg/ml proteinase K). The mixture was incubated for 1 h at 30° C. with stirring from time to time and then centrifuged at 10,000 rpm for 15 min. at 4° C. 1 vol. of chloroform/isobutanol (24:1) was added to the supernatant. This was followed by thorough mixing (6 to 7 times with standing in between periods of mixing, total about 20 min.) and centrifuging for 20 min. at 10,000 rpm and 4° C. The organic phase (with chlorophyll, if present, and proteins in the interphase) was discarded and the mixture was extracted again with 1 vol. of chloroform/isobutanol (24:1) and centrifuged for 20 min. at 10,000 rpm and 4° C. 2.5 vol. cold ethanol was added to the upper phase and the mixture was stored overnight at −20° C. it was then centrifuged for 10 min. at 10.000 rpm and 4° C., the pellet was thoroughly vacuum-dried and resuspended in 20 ml TE-buffer (10 mM Tris-HCl (pH 8.0), 1 mM EDTA). The solution was stored at 4° C. before CsCl banding. To test that the genomic DNA had a high molecular weight, 1 to 10 μl of the genomic DNA was run on, a 1% agarose gel; DNA which has not been degraded will migrate close to the slot in a broad band. The genomic DNA was then banded on a CsCl gradient: 20 g of CsCl was poured into the 20 ml of genomic DNA and 1.25 ml ethidium bromide solution (stock: 5 μg/ml) was added. Another solution (A) was prepared: solid CsCl was mixed with TE-buffer (w/v) and 0.2 mg ethidium bromide/ml was added. The DNA solution was poured into quick-seal polyallomer tubes, which were then filled up with solution (A) and sealed. The tubes were centrifuged in a Beckman VTI 65 rotor at 15° C. and 45.000 rpm for 48 h. The centrifuge was stopped without using the brake. The genomic band was removed under UV-light with a syringe, and the ethidium bromide was extracted with CsCl-saturated isopropanol (7 to 8 times). The CsCl was then removed from the DNA by dialysis in TE-buffer for 72 h with 6 changes of buffer. It was generally not necessary to precipitate the DNA at this stage (precipitation was avoided, since high molecular weight DNA is very hard to resuspend) unless very little DNA was isolated. The DNA concentration was measured at $OD_{260\ nm}$ assuming 50 μg DNA/ml at $OD_{260}=1$. The genomic DNA, which was used for restriction enzyme digestion, was stored at 4° C. (45).

Preparation of plasmid DNA

Small scale preparation of plasmid DNA was performed as follows: bacterial strains harboring the plasmids were grown overnight in 2 ml L-Broth (LB) medium with either 15 μg/ml tetracycline (tet) or 35 μg/ml ampicillin added. The operations were performed in 1.5 ml Eppendorf tubes and centrifugation was carried out in an Eppendorf centrifuge at 4° C. The cells from the overnight culture were harvested by centrifugation for 2 min., washed with 1 ml 10 mM Tris-HCl (pH 8.5), 1 mM EDTA and centrifugated for 2 min. The pellet was suspended in 150 μl of 15% sucrose, 50 mM Tris-HCl (pH 8.5), 50 mM EDTA by vortexing. 50 μl of 4 mg/ml lysozyme was added and the mixture was incubated for 30 min. at room temperature and 30 min. on ice. 400 μl ice cold $H_2O$ was added and the mixture was kept on ice for 5 min. incubated at 70°–72° C. for 15 min. and centrifuged for 15 min. To the supernatant was added 75 μl 5.0M Na-perchlorat and 200 μl isopropanol (the isopropanol was stored at room temperature), and the mixture was centrifuged for 15 min. at 5° C. The pellet was suspended in 300 μl 0.3M Na-acetate and 2–3 vol. cold ethanol was added. Precipitation was accomplished by storing at either 5 min. at −80° C. or overnight at −20° C., centrifuging for 5 min., drying by vacuum for 2 min. and redissolving the pellet in 20 μl $H_2O$. The yield was 5–10 μg plasmid DNA (46).

Large scale preparation of plasmid DNA was accomplished by simply scaling up the small scale preparation ten times. Working in 15 ml corex tubes, all the ingredients were scaled up ten times. The centrifugation was carried out in a Sorvall cooling centrifuge at 4° C. Only changes from the above will be mentioned in the following. After incubation at 70°–72° C., the centrifugation was for 30 min. at 17.000 rpm. After adding isopropanol and after adding cold ethanol, the centrifugation was for 15 min. at 17.000 rpm. The final plasmid DNA pellet was suspended in $H_2O$ and transferred to an Eppendorf tube and then given a short spin to remove debris. The supernatant was adjusted to 0.3M Na-acetate and 2–3 vol. cold ethanol were added. The pellet was resuspended in 40 μl $H_2O$. The yield was usually 20–80 μg plasmid DNA.

To obtain very pure plasmid DNA, 200–300 μg of isolated plasmid DNA from the upscaled method were banded on a CsCl gradient. Solid CsCl was mixed with $H_2O$ (1:1 w/v) and 0.2 mg ethidium bromide/ml was added. The solution was poured into a quick-seal polyallomer tube and the plasmid DNA, mixed with solid CsCl (1:1 w/v), was added. The tube was filled, sealed and centrifuged in a Beckman VTI 65 rotor at 15° C., 48.000 rpm for 16–18 hours. The centrifuge was stopped by setting the timer at zero without using the brake. The banded plasmid DNA was withdrawn from the tubes by using a syringe and the ethidium bromide was extracted with CsCl-saturated isopropanol 7–8 times. The CsCl was removed by dialysis in 10 mM Tris-HCl (pH 8.0), 1 mM EDTA for 48 hours with three changes of buffer. The DNA was precipitated by adjusting to 0.3M Na-acetate and adding 2–3 vol. cold ethanol (12).

Restriction Enzyme Digestions

All restriction endonucleases were from Biolabs or Boehringer Mannheim and were used according to the supplier's instructions. 1 unit of enzyme was used for 1 μg of DNA and incubation was for 2 hours. The buffer was changed in double digestions, either by changing the volume or by adding the necessary ingredient according to the enzyme instructions.

Electrophoretic fractionation of DNA fragments

Non-denaturing gels

Agarose gels were used for estimating the concentration of plasmid DNA, for separation of restriction enzyme digested genomic DNA (0.8 or 1% agarose gels), for mapping restriction enzyme digested plasmid DNA and for Southern blotting (2% agarose gels) and Northern blotting (1.5% agarose gels). The Northern blotting gels have been described above. The other gels were prepared in a horizontal slab gel apparatus, and electrophoresis was either carried out in 2×McArdle buffer (2×McArdle:80 mM Tris, 36 mM NaCl, 24 mM Na-acetat, 4.4 mM EDTA, adjusted to pH 8.0 with glacial acetic acid) at 45 mA for 18 h, or carried out in 1×TBE buffer (1×TBE:89 mM Tris-borate, 89 mM boric acid, 2 mM EDTA) at 70 mA for 2–3h. The gels contained 5 μg ethidium bromide/ml gel. Tracking dye (35% ficoll (M.W 40.000), 5 mM EDTA, 0.04% Bromophenol Blue) was added to the DNA samples before loading. The gels were photographed using long wave UV light with an orange filter and Polaroid film No. 665 (13, 14).

5% acrylamide gels were used for mapping restriction enzyme digested plasmid DNA and for isolation of specific DNA fragments. The gel (0.1×12×15 cm) was formed between two glass plates held apart by spacers. One gel contains 37 ml $H_2O$, 17.5 ml 19% acrylamide, 1% bisacrylamide, 4.4 ml TEMED (0.5% $N_1N_1NN$-tetraethylethylenediamine) 7 ml 10×TBE, 4.4 ml amper (1.6% ammoniumperoxodisulphate). Electrophoresis was carried out for 2 h at 180–200 V in a vertical slab gel apparatus. tus. The gel was stained in 5 μg/ml ethidium bromide for 30 min., after which the bands were visualized using long wave UV light and photographed as described above (13).

DNA sequencing gels

8% acrylamide—8M urea gels (0.035×20×47 cm) were used for separation of DNA fragments after sequence reactions. The gel contained the following: 15.75 ml 38% acrylamide, 2% bis-acrylamide, 36 g urea and $H_2O$ up to 70 ml. The solution was deionized (one spoonful ion exchanger, with stirring for 30 min and removal by filtration) and 7.5 ml 10×TBE, 1 ml H₂O, 2.7 ml amper (1.6%) were added. The mixture was degassed, cooled on ice and 40 µl concentrated TEMED was added. The gel was immediately poured between two glass plates held apart by spacers. The gel was run at 40 W for 1 ½–4 hours, then dried by a gel drier and autoradiographed for 3–48 h at room temperature (12).

Recovery of DNA from gels

DNA fragments were eluted from acrylamide gels to circumvent problems with enzyme-toxic compounds found in agarose. A DNA fragment cut from a 5% acrylamide gel was placed in a dialysis bag with 200 µl ½×TBE. The bag was placed parallel to the electrodes in a horizontal gel apparatus and soaked with ½×TBE. Electrophoresis was at 150 V for 2–4 hours. The current was inverted 30 sec. and the bag was controlled under UV light. The DNA solution was adjusted to 0.3M Na-acetate and precipitated with 2–3 vol. of cold ethanol (12).

Southern Transfer

A 2% agarose gel was soaked in denaturation buffer (0.5M NaOH, 1.5M NaCl) for 2×15 min. The liquid was constantly stirred with a magnetic stirrer. The gel was then soaked in neutralization buffer (0.5M Tris-HCl (pH 7.0), 3.0M NaCl) for 3×10 min. The neutralized gel was placed on a solid support covered with a piece of filter paper prewetted in 20×SSC (1×SSC: 0.15M NaCl, 0.015M Na₃-citrate, pH 7.0), the ends of the filter paper having been dipped into a tray with 20×SSC to form a wick. A nitrocellulose filter, cut to the size of the gel, was wetted in H₂O and in 20×SSC and laid on top of the gel, avoiding air bubbles. Four pieces of parafilm (an "umbrella") were placed on the edges of the nitrocellulose filter. A piece of filter paper prewetted in 20×SSC was placed on top of this and over the filter paper was placed a stack of dry filter paper. On this stack were placed several layers of paper towels cut to the size of the gel. Finally, a glass plate and a weight were placed on top. The blotting took place for a period of 16–18 hours, after which the nitrocellulose filter was marked, washed for 10 minutes in 3×SSC, air dried and baked in a vacuum oven for 2 hours at 80° C. The procedure was identical for 0.8% agarose gels with large DNA fragments, except that the gels were pretreated by soaking 2×15 minutes in 0.25M HCl (15).

Nick translation

The following was mixed in an Eppendorf tube:

3 µl of 10×nick buffer (500 mM Tris-HCl (pH 8.0), 50 mM MgCl₂, 100 mM β-mercaptoethanol)

2 µl of a mix containing 1 mM dCTP, 1 mM dGTP and 1 mM dTTP in H₂O 0.4–2 µg of an isolated DNA fragment (from 5% acrylamide gel)

4 µl of DNase (1 mg/ml) diluted to $10^{-4}$

25 µCi of $\alpha^{32}$P-dATP

1 µl DNA polymerase I (Kornberg)

The total volume was adjusted to 30 µl with H₂O.

The mixture was incubated at 14° C. for 2–3 h (16).

A column was made from a pasteur pipette, plugged with ordinary glass wool, and filled to a height of 7 to 8 cm with Sephadex G-100 (the Sephadex G-100 is equilibrated in TE-buffer (10 mM Tris-HCl (pH 8.0), 1 mM EDTA).

The nick-translated DNA was passed over the column using TE-buffer, the first peak was collected and the incorporated radioactivity was estimated by liquid scintillation counting. Probes having a specific activity of $2\times10^7$ to $8\times10^8$ cpm/µg DNA were used. They were heat denatured before being added to the hybridization solutions.

For hybridization to λ-ZAP phage filters, the amounts of the ingredients in the nick were doubled, except for the $\alpha^{32}$p-dATP, which was used in an amount of 100 µCi (double nick translation). This usually gave $1.7\times10^8$ cpm/5 µl of probe used (1.6 µg), which was enough for one plastic bag with filters with a size of 22×22 cm.

Labelling of cDNA

Radioactive cDNA for hybridization experiments was prepared by first strand synthesis of polyA-mRNA in the presence of a radioactive nucleotide.

The following was mixed in an autoclaved Eppendorf tube:

1 µl of 20×cDNA stock (1×cDNA stock: 50 mM Tris-HCl (pH 8.3), 100 mM KCl, 10 mM MgCl₂, 5 mM dithriothreitol), 1 µl of each of dCTP (10 mM), dGTP (10 mM) and dTTP (10 mM), 1 µl of dATP (100 µM plus 50 µCi $\alpha^{32}$-PdATP, 2 µl of oligo (dT) (P.L. Biochemical), 2–3 µg of polyA-rich RNA, 20 units of RNasin (an RNase inhibitor, Biotec Inc.)

40 units of avian myeloblastosis virus reverse transcriptase (J. W. Beard, Life Science Inc.) and sterile H₂O up to 20 µl.

The mixture was incubated for 45 min. at 37° C., after which 1 µl of dATP (10 mM) was added and the mixture was kept at 37° C. for 15 min. (chase 15). The RNA-DNA hybrids were purified on a Sephadex G-100 column (7 to 8 cm in a pasteur pipette plugged with ordinary glass wool and equilibrated in TE-buffer (10 mM Tris-HCl (pH 8.0), 1 mM EDTA)). The first peak was collected and the hybrids were precipitated with 5 µl tRNA (1 mg/ml), 80 mM NaCl (final concentration) and 2.5 vol. cold ethanol. The reaction was checked by running $5\times10^5$ cpm of the RNA-DNA hybrids on a 5% acrylamid gel. The gel was exposed to an X-ray film overnight at room temperature and it showed a smear which was strongest near the slots. The RNA was hydrolysed with 0.4M NaOH (final concentration) for 1 h at 50° C. and neutralized with HCl. The cDNA was then ready to add to the hybridization solution (17).

Employing another method of preparing radioactive cDNA, a small portion of polyA-rich RNA was used for constructing the λ-ZAP library. The radioactive cDNA was prepared to ensure that the RNA had not been degraded during its isolation. Both the first and the second strand were synthesized from 2 µg polyA-rich RNA and 20 µCi $\alpha^{32}$P-dATP by using a Boehringer Mannheim cDNA synthesis kit. ¹⁄₂₀ of the double-stranded cDNA was run on a 5% acrylamid gel. The gel was dried, and exposed to X-ray film at room temperature. The resultant band and smear showed that the cDNA had a high molecular weight (12).

Hybridization of DNA

The nitrocellulose filters from Southern transfer or λ-ZAP plaque filters were wetted in 2×SSC [1×SSC: 0.15M NaCl, 0.015M Na₃-citrate, pH 7.0] and placed in a heat-sealed plastic bag with prewarmed 67° C.) prehybridization solution. Prehybridization took place for 2 h at 67° C., the bag being gently shaken. The solution was exchanged with prewarmed (67° C.) hybridization solution, the radioactive probe was added and hybridization was carried out at 67° C. for 18 h. The bag was gently shaken to ensure constant movement of the liquid over the nitrocellulose filters. After hybridization, a washing procedure was carried out. Different stringency conditions were used:

Low stringency conditions

Prehybridization and hybridization solutions: 10×Denhardt (0.2% polyvinyl-pyrrolidone (MW 40.000), 0.2% ficoll (MW 400.000), 0.2% bovine serum albumin), 6×SSC, 0.1% SDS, 10 µg/ml polyA, 50 µg/ml of denatured (heat) sonicated *E. coli* DNA (not salmon DNA), and the denatured (heat) radioactive probe. The filters were washed in prewarmed (67° C.) solutions: 2×15 min in 10×Denhardt, 4×SSC, 0.1% SDS; 4×15 min in 4×SSC, 0.1% SDS. The filters were air-dried and covered with plastic film. Autoradiography was carried out for 3 h to 24 h at −80° C. with and without intensifying screens.

Medium high stringency conditions

Prehybridization and hybridization solutions were the same as above, except that 6×SSC was replaced with 4×SSC. The following wash solutions were prewarmed to 67° C.:

10×Denhardt, 2×SSC, 0.1% SDS for 2×15 min. and 1×SSC, 0.1% SDS for 4×15 min. The filters were air-dried and covered with plastic wrap, and X-ray film was exposed to the filters for 3 h to 3 weeks with and without intensifying screens.

The procedure for genomic filters was as follows (medium high stringency):

Prehybridization and hybridization solution: 10×Denhardt, 3×SSC, 0.1% SDS, 10% (w/v) Dextransulphate, 10 µl/ml polyA and 50 µg/ml denatured sonicated *E. coli* DNA. The filters were washed in prewarmed (67° C.) hybridization solution without Dextransulphate for 5×10 min at 67° C., and for 4×15 min. in 10×Dehnhardt, 1×SSC, 0.1% SDS. The filters were rinsed in 3×SSC and air-dried, and X-ray film exposed to the filters as described above (12 and 18).

Filling of recessed 3' ends (for subcloning Hinf fragment from pO36)

The following was combined in an Eppendorf tube: 10 µl containing up to 1 µg of DNA fragment, 1 ml of a 2 mM solution of the four dNTP's, 2 µl of a 10×nick translation buffer (0.5M Tris-HCl (pH 7.2), 0.1M $MgSO_4$, 1 mM dithiotreitol, 500 µg/ml bovine serum albumin) and $H_2O$ up to 20 µl. 2 units of Klenow polymerase were added and the mixture was mixed and incubated for 30 min at 22° C. The mix was heated for 5 min at 70° C. to inactivate the polymerase, extracted twice with saturated phenol (the phenol was first mixed with 0.1M Tris-HCl, then mixed twice with TE-buffer (10 mM Tris-HCl (pH 8.0), 1 mM EDTA) and once with chloroform, precipitated with 0.3M Na-acetate and 2.5 vol. cold ethanol and rinsed twice with 70% cold ethanol. The blunt-ended DNA fragment was then ligated to a blunt-ended vector in T4-DNA ligase buffer (12).

Subcloning

Preparation of vectors

Vectors (pBS− or pBS+) were digested with one or two restriction enzymes, extracted twice with saturated phenol (the phenol was first mixed with 0.1M Tris-HCl, then mixed twice with TE-buffer (10 mM Tris-HCl (pH 8.0), 1 mM EDTA) and once with chloroform and precipitated with 0.1M NaCl and 2.5 vol. cold ethanol. The pellet was rinsed in 80% cold ethanol and dissolved in $H_2O$, giving a concentration of 25–50 ng/µl. The vectors were always tested for background before use (self-ligation with and without T4-DNA-ligase).

Ligation

The plasmid comprising the fragment to be subcloned was digested with one or more appropriate restriction enzymes and run on a 5% acrylamid gel, after which the fragment was isolated as described under "Recovery of DNA from gels". 1 µl (25 ng/µl) of a solution containing the vector was combined with the fragment (ratio of vector: fragment 1:2 based on the number of molecules),. 2 µl of T4-ligation buffer (5×(50 mM Tris-HCl (pH 7.6), 10 mM $MgCl_2$, 1 mM ATP, 1 mM dithiothreitol, 5% (w/v) polyethylene glycol-8000)) 0.5 µl of T4-DNA ligase (BRL) and $H_2O$ up to 10 µl. The mixture was incubated for 20 h at 14° C. if the ligated DNA fragments had sticky ends. If the DNA had blunt ends, then 1 µl of T4-DNA ligase was added and the incubation was for 1 h at room temperature. The ligation mix was stored at −20° C. if not used immediately. Usually only 5 µl of the ligation mix was used for transformation.

Preparation of competent cells

JM109 cells (or other cells, for example HB101) were inoculated in 4 ml L-Broth made to 10 mM $MgSO_4$ and 10 mM $MgCl_2$ (from 1M $MgSO_4$, 1M $MgCl_2$; autoclaved). The cells were grown overnight at 37° C. 1 ml of the overnight culture was added to 40 ml of prewarmed (37° C.) LB medium (10 mM $MgSO_4$, 10 mM $MgCl_2$). The culture was shaken at 250–275 rpm. The cells were harvested from 30 ml of culture when the $OD_{450}$ had reached 0.8 to 0.9 by centrifugation at 5000 rpm for 10 min at 4° C. It was important that the OD was below 1 to ensure that the cells were aerated as much as possible. The pellet was very gently suspended in 30 ml of cold 0.1M $CaCl_2$ (autoclaved) in a centrifuge tube, the tube being cooled by an ice-bath during the process, followed by centrifuging for 10 min at 5000 rpm and 4° C. The pellet was suspended very gently in 15 ml of cold 0.1M $CaCl_2$, kept on ice for 20 min and centrifuged for 10 min at 5000 rpm and 4° C. The cells were gently suspended in 3 ml of cold 0.1M $CaCl_2$ and kept for at least 1 h on ice before being ready for use (19).

Transformation

5 µl of ligation mix was combined with 95 µl of cold sterile TCM (10 mM Tris-HCl (pH 7.5), 10 mM $CaCl_2$, 10 mM $MgCl_2$), and 200 µl of competent JM109 cells (or another type of cells). The mixture was allowed to stand for at least 40 min on ice, then 5 min at 37° C. (or 2 min at 42° C.). The mixture was then transferred to a sterile glass tube containing 0.8 ml of L-Broth, 10 mM $MgSO_4$, 10 mM $MgCl_2$ and incubated for 45 min at 37° C. with gentle shaking, then plated out (sterile technique) on 5 AXI plates (or other suitable plates, for example amp or tet) at 0.2 ml/plate. The plates were allowed to stand for 10 min before being inverted and incubated overnight at 37° C. They were stored in plastic bags upside down at 4° C.

Isolation and testing of subclones 1 to 6 recombinant clones (white on AXI plates when the vector is pBlueScript) from each plate were isolated and plasmid prepared from the clones were digested with the appropriate restriction enzyme(s) and run on a 2% agarose gel to ensure that the inserted fragment had the right size. If this was the case, then the clone was cultivated overnight in 4 ml of L-Broth, mixed with 25% sterile glycerol and stored at −80° C. For sequencing of an inserted fragment, see "plasmid sequencing". For fragment isolation (probes) and nick translation, see the relevant sections (12, 20).

Screening of the λ-ZAP library

The liter of the amplified λ-ZAP library's titer was determined in duplicate prior to the screening. Infection competent BB4 cells were prepared by inoculating the cells in 30 ml fresh L-Broth containing 300 µl of 20% maltose and cultivating them overnight at 37° C. The cells were harvested at 10.000 rpm for 10 min and 4° C. and resuspended gently in cold sterile 10 mM $MgSO_4$ (30 ml), and kept on ice until use. 100 µl of λ-ZAP phages, diluted in φ-buffer (22 mM $KH_2PO_4$, 49 mM $Na_2HPO_4$, 85 mM NaCl, 1 mM $MgSO_4$, 0.1 mM $CaCl_2$, 0.001% of gelatine; autoclaved) were mixed with 0.2 ml of freshly made BB4 cells, incubated for 30 min. at room temperature, mixed with 2.5 ml warm (42° C.) 0.6% top agar containing 10 mM $MgCl_2$ and plated out on LB plates.

For screening of the library, 22×22 cm LB plates (dried for 3-4 h at 37° C.) were used. Each plate can carry about 1×10$^5$ λ-ZAP plaques, and they were mixed with 1 ml of BB4 cells (prepared as above) and allowed to stand for 30 min at room temperature. This mixture was then added to 25 ml of warm (42° C.) 0.3% top agarose+10 mM MgCl$_2$ and the solution was poured onto a fresh dry LB plate. The large LB plates were incubated (not upside down) overnight at 37° C. Phages from the plaques were transferred to nitrocellulose filters in duplicate. The plates were placed at 4° C. for 1 to 2 h to prevent the agarose layer from sticking to the nitrocellulose filters. Just before use, they were placed on ice and they remained on ice when working with the nitrocellulose. Two nitrocellulose filters (A and B) plus the plate were marked at three sites for orientation of the filters. Filter A was laid on the plaques for 45 sec; then floated on denaturation buffer (0.5M NaOH, 1.5M NaCl), with the phages facing up, for 45 sec, then floated on neutralization buffer (0.5M Tris-HCl (pH 7.5), 3.0M NaCl) for 5 min and finally floated on 2×SSPE (1×SSPE: 180 mM NaCl, 10 mM NaH$_2$PO$_4$, 1 mM EDTA, pH 7.4) for at least 2 min. The filter was air-dried and baked in a vacuum oven for 2 h at 80° C. Filter B was laid on the same plate, after filter A, for 120 sec and then treated as filter A (12). These filters were used in the hybridization. X-ray film from both filters was orientated so that the signals from filter A fit the signals from filter B. The positive plaques were cut out with a scalpel (1×1 cm blocks) and submerged in 1 ml of φ-buffer (shaking the tube before use). All tubes with phages in φ-buffer were stored airtight (parafilm) at 4° C. after 2-3 drops of chloroform had been added. The plaque plates (22×22 cm) were stored by placing a piece of soaked (chloroform) Wattman filterpaper in the lid, then making the plates airtight (parafilm) and letting them stand with the plaques facing up at 4° C. To isolate a positive plaque from the 1×1 cm block (containing about 2000 plaques), dilutions in φ-buffer were made and plated with BB4 cells on round fresh LB plates (8.5 cm diameter) with 2.5 ml of 1% warm (42° C.) top-agar+10 mM MgCl$_2$. The dilution which gave 1500-3000 plaques was used to make the nitrocellulose filter prints. The method was exactly as described for the large (22×22 cm) LB plates, except that the filters (A and B) were marked by sticking a syringe needle through the filter down into the plate. After hybridization to the round filters and autoradiography, the positive signals form A and B were matched. The plaques were isolated by sticking the tip of a pasteur pipette through the plate and releasing the plaques (by blowing the other end) in 1 ml of φ-buffer. Again, dilutions were made, and a dilution with 150-300 plaques was used to make the nitrocellulose prints. The procedure was the same as described for the dilution with the 1500-3000 plaques. The positive plaques were isolated and diluted, and the dilution giving 15-30 plaques was used to make nitrocellulose prints. At this point, all plaques on the filters (A and B) generally hybridized, showing that the isolated phages were pure. If this was not the case, another round was necessary, after which the phages were pure. The phages were then ready for the "Excision Protocol for λ-ZAP phages".

Excision Protocol for λ-ZAP phages

XL1-Blue cells were inoculated in 4 ml of fresh LB medium for an overnight culture (gently shaken at 37° C.). 0.5 ml of the overnight culture was added to 25 ml of fresh LB medium and placed, with continuous shaking, at 37° C. until OD$_{450}$=0.5. To a prewarmed sterile glass tube was added:

100 μl of XL1-Blue cells OD=0.5

100 μl of a clean λ-ZAP phage stock (containing >1×10$^5$ phage particles,

5 μl of R408 helper phage (1×10$^6$ pfu/ml)

2 μl of 1M sterile MgSO$_4$.

The tube was held for 15 min at 37° C. 2.5 ml of fresh LB medium was added, and the tube was shaken vigorously for 4 h at 37° C. The tube was then heated for 20 min. at 70° C. before transferring 1.5 ml to an autoclaved Eppendorf tube. The tube was given a short spin, after which the supernatant was transferred to a new autoclaved Eppendorf tube. The rescued phages can be stored at this point for 1 to 2 months at 4° C. To transfer the packaged, rescued plasmid to cells, the following procedure was followed: XL1-Blue cells were inoculated in 4 ml of fresh LB medium for an overnight culture and cultivated as described above. Two sterile glass tubes containing 100 μl of XL1-Blue cells OD=0.5 were prepared. To the first glass tube, 200 μl of the packaged plasmid was added and to the second glass tube 2 μl were added. The tubes were allowed to stand at 37° C. for 15 min. 100 μl from each glass tube was transferred to a new sterile glass tube containing 100 μl of fresh LB medium. The 200 μl was plated out on a dry (dried at 37° C. for 20 min) LB-ampicillin plate and incubated upside down overnight at 37° C. (31).

The colonies appearing on the plates contained the pBlue Script plasmid with the inserted cDNA. The colonies from these plates were grown in LB medium containing 35 mg of ampicillin per liter.

DNA sequencing

The plasmid (double stranded template) to be sequenced was purified by the plasmid small scale preparation method. The DNA was denatured in 0.2M NaOH (5 min at room temperature), the mixture was neutralized by adding 0.4 vol of 5M ammonium acetate (pH 7.5) and then precipitated with 4 vol. of cold ethanol (5 min at −80° C.). The pellet was rinsed with 70% cold ethanol and resuspended in 10 μl H$_2$O. Two reactions were set up for each plasmid, one for each primer that was used. A 17-mer sequencing primer #1212 (Biolabs) and reverse sequencing primer #1201 (Biolabs) were used.

Sequencing was accomplished with a Sequenase™ DNA Sequencing Kit from United States Biochemical Corp., following the sequencing Protocol enclosed in the kit (22).

EXAMPLE 1

Amylase activity in potato tissue

It is desirable to know in which tissue amylase is active, since presumably amylase mRNA is present in such tissue. Growing tuber sprouts demand nutrition (such as sucrose) from the tuber, and starch is broken down to accommodate this demand. Different tissues from sprouting potatoes were therefore tested for amylase activity. Thin slices of sprouting tubers (Dianella, Saturna) were placed in I$_2$/kI solution. The periderm (cells making up the tuber skin), the vascular tissue and the sprouts were not coloured, while the rest of the tuber tissue (parenchyma, storage cells) was coloured. While this test indicates where starch is present (dark blue colour) and where starch is absent (the colourless areas), it does not show where amylase is present. There was no visible difference in the colour pattern of Saturna and Dianella potatoes.

Thin slices of the sprouts were placed on a 1% starch plate, and incubated for 1 h at 37° C. with no visible effect. For comparison, mouse urine spotted on a 1% starch plate gives a clear spot after incubation for 20 min at 37° C. (23). Although the slices were very thin, the distance the enzyme has to travel to come into contact with the substrate may still be too long. On the basis of the colouring pattern seen for the sprouting tubers, it was decided to make extracts of the different regions indicated in FIG. 6.

The extracts were prepared as described above ("Materials and Methods") from both Dianella and Saturna. After incubation at 20° C. for 16 h, only Dianella sprouts showed a weak reaction (orange spot). Another set of extracts was incubated at 37° C. and here Dianella sprouts showed a strong reaction (clear spot), demonstrating the presence of amylase in these sprouts. Saturna sprouts showed a weak reaction after incubation at 37° C., weaker than the reaction seen for Dianella sprouts at 20° C. The clear difference observed in the amylase level of Dianella and Saturna sprouts is correlated with the sugar level seen in these varieties (cf. Example 20 and FIG. 22). In order to obtain a stronger reaction from Saturna sprouts, 10 g were frozen (−70° C. for 5 min, −20° C. for 1 h) before grinding in 5 ml extraction buffer (see Materials and Methods). After incubation at 37° C., the spot was pink-red, but the reaction was still not as evident as the reaction seen with the 2 g of fresh Dianella sprouts.

The rest of the tissue extracts (B, C and D from both Dianella and Saturna) showed a darker blue colour than the surroundings (on the 1% starch plate) after staining with $I_2/kI$ solution. There is thus more starch in these spots than in the surroundings. The parenchym tissue (D on the drawing) from both varieties was also tested after having been frozen, and the spots were still darker than the surroundings. The frozen parenchym tissue was then ground without extraction buffer and the resulting potato juice (after centrifugation to remove debris) was tested. A very weak reaction was seen after incubation at 37° C. for juice from both Saturna and Dianella. This reaction may be due to there being so much substrate (i.e. starch) for the amylase in the parenchym tissue that the enzyme needs much more time to degrade the starch at the plate. A maximum incubation time of about 16 h was used, since the plates curl up if they are incubated much longer than 16 h at 37° C.

On the basis of the above, if may be concluded that amylase activity is present in both sprouts and tuber parenchym tissue of Saturna and Dianella potatoes. The highest activity is seen with Dianella sprouts.

EXAMPLE 2
Preparation of barley α-amylase probes

Two plasmids (050 and 036), each of which codes for a barley α-amylase, were provided by John C. Rogers of Washington University Medical Center, St. Louis, USA. The two plasmids were originally constructed from cDNA derived from polyA-rich RNA isolated, after hormone induction, from the aleurone cell layer of barley grains. Plasmid 050 codes for a type A (=clone E) (27) α-amylase, and plasmid 036 codes for a type B (=pM/C) (24) α-amylase. According to information received with the plasmids p050 contains the barley PstI insert from clone E inserted into the PstI site in the polylinker of the vector pSP64 (26). To increase plasmid DNA yields the same PstI fragment was inserted into the vector pBS- (31). This new clone pBS050 thus contains the identical barley insert cloned in clone E. According to information received, plasmid 036 contains a BamHI-HindIII fragment from clone pM/C inserted into the polylinker of the vector pSP64 (FIG. 7). The complete sequence of the fragment has not been published, and as shown in Example 3, the fragment includes sequences that give rise to a strong false hybridization signal. In heterologous hybridizations at low stringency ("Materials and Methods") the signal to noise ratio can be increased if the heterologous probe only includes sequences that will hybridize in control experiments (Example 3). The barley insert in p036 contains two SacI sites that divide the coding region and cut near the termination codon (positions 599 and 1388 in FIG. 2 of reference 24). The 5' leader sequence and the start of the coding region encoding the signal peptide of the barley α-amylase was not expected to be conserved between barley and potato, and a HinfI site at position 152 in the above-mentioned figure was used to remove the first 152 nucleotides from the barley probe as follows. The HinfI fragment shown in FIG. 7, in which the righthand site is in the vector pSP64, was subcloned in the vector pBS- and from the recombinants one was chosen in which the fragment cloned has the orientation shown in FIG. 7. This plasmid, pBS036, liberates after digestion with SacI two fragments containing essentially only regions coding for mature barley α-amylase. In addition, pBS036 gives a better yield of plasmid DNA than 036.

EXAMPLE 3
Detection of hybridization between barley α-amylase gene sequences and potato nucleotide sequences PolyA-rich DNA prepared from Dianella sprouts as described under "Materials and Methods" was selected since this tissue was found to have the highest α-amylase activity (Example 1). In order to elucidate whether the complex mixture of messengers in the polyA RNA preparation contains sequences that will hybridize with the barley α-amylase sequences, plasmids pBS050 and pBS036 were hybridized with radioactive copy DNA synthesized from the polyA-rich RNA, using a method similar to first strand synthesis for cDNA cloning as described in "materials and Methods". The hybridization conditions (hybridization at 67° C. in 6×SSC, wash at 67° C. in 4×SSC) were selected based on previous experience with heterologous hybridizations in complex mixtures of molecules (28, 29).

The result of the experiment is shown in FIG. 8. It shows that the potato copy DNA does hybridize specifically with α-amylase coding regions from barley. In particular, the 800 bp SacI fragment from pBS036 that encodes the C-terminal part of barley α-amylase type B hybridizes well, whereas the 350 bp SacI fragment encoding the N-terminal part does not hybridize. That the hybridization is specific is indicated by the lack of hybridization of a similar size DNA fragment from a control plasmid (lane 1, FIG. 8). The barley insert from plasmid pBS050 encoding α-amylase type A also hybridizes, albeit weakly, with the potato copy DNA. As a positive control for the hybridization a plasmid encoding a highly conserved, ubiquitous protein, ubiquitin, was used, and as expected it hybridizes with the potato copy DNA. The intensity of the hybridization to the ubiquitin coding fragment, the 800 bp SacI fragment from pBS036, and the Pst insert from pBS050 is weak compared with the hybridization of two strong bands seen in lanes containing pBS036, and it was concluded that the strong bands are due to hybridization of the copy DNA to the small region indicated by a star in FIG. 7. The sequence of the region is not known but it is proposed that the strong hybridization is the result of a chance homology with ribosomal RNA sequences (found in even the most purified polyA-rich RNA). This suggestion is supported by the finding that the barley copy DNA gives a similar strong hybridization.

The results of the experiment show that 1) Dianella sprout polyA-rich RNA contains sequences that hybridize specifically with barley α-amylase coding sequences, 2) the 800 bp SacI fragment from pBS036 is the most suitable probe, and 3) the hybridization conditions are sufficiently permissive to detect hybridization without creating an excessive background hybridization. It was concluded that the 800 bp SacI fragment (the probe in FIG. 7) could be used to screen a cDNA library made from polyA-rich RNA from Dianella sprouts with hybridization at 67° C. in 6×SSC and washing at 67° C. in 4×SSC.

EXAMPLE 4
Construction of a potato sprout cDNA library

PolyA-mRNA was prepared from Dianella sprouts as described under "Materials and Methods". The quality of the polyA-mRNA was tested by synthesizing a small portion into cDNA as described above.

The polyA-mRNA was cloned into the vector λ-ZAP with the aid of EcoRI linkers (30).

λ-ZAP is a hybrid vector consisting of a λ vector with the pBlue Script SK(−) plasmid inserted. λ-ZAP has six unique cloning sites that can accommodate inserts from 0–10 Kb in length. It has the ability to automatically excise the inserted region with a helper phage and to circularize it, forming the pBlueScript SK(−) plasmid. The inserted cDNA is situated in the polylinker of the pBlueScript SK(−)plasmid (31). The estimated titer of the primary library was approximately $7.0 \times 10^6$ pfu (plaque forming units), of which approximately 9% were non-recombinants. The stock of the unamplified library was $8.0 \times 10^5$ pfu/ml and the stock of the amplified library (amplified $10^6$ pfu from the primary library) was $4.0 \times 10^{10}$ pfu/ml.

Preparation of the Sac 800 probe $3 \times 10$ μg of very pure (CsCl-banded) pBS 036 (FIG. 7) plasmid was digested with SacI and run on a 5% acrylamide gel. pBR327 digested with BstNI was size marker giving 3 bands: 1855 bp, 928 bp and 475 bp. The Sac 800 band was isolated, suspended in 30 μl $H_2O$ and stored at −20° C. Each time a double nick was made (i.e. using double the amount of the ingredients), 5 μl of the store probe was used.

EXAMPLE 5
Isolation of α-amylase cDNA clones from potato

One set of nitrocellulose filters (3A and 3B, with $1 \times 10^5$ plaques) was hybridized at low stringency (hybridized at 6×SSC and washed at 4×SSC as described above) with approximately $1.7 \times 10^8$ cpm of the radioactive Sac800 probe. Another set of nitrocellulose filters (2A and 2B, with $1 \times 10^5$ plaques) was hybridized at a somewhat higher stringency (hybridization and washing at 2×SSC), again with approximately $1.7 \times 10^8$ cpm of the radioactive Sac 800 probe. After 3 hours of autoradiography with two intensifying screens, the X-ray film from filters 3A and 3B (the low stringency filter) showed positive signals, while the X-ray film from filters 2A and 2B (the higher stringency filters) showed no signals. Even after 18 hours of autoradiography of 2A and 2B, they still did not show positive signals.

Among about 100,000 clones, eight positive signals from filters 3A and 3B were found and an additional positive signal was found on filter 3A in a region where the two filters did not overlap. The frequency of α-amylase cDNA clones in the library gives an indication of the prevalence of α-amylase messenger RNA in total Dianella sprout messenger RNA. The frequency was $8 \times 10^{-5}$, whereby the α-amylase mRNA was fairly rare, constituting approximately 0.008% of the total mRNA. All nine signals were located on the original L-Broth plate (22×22 cm) and isolated therefrom (Step 1) (see "Materials and Methods"). They were given the names ZAP1 and ZAP9. They were plated out, after serial dilutions, and two duplicate replicas (A, B) were made from each plate (with 1500–3000 plaques per plate). The nitrocellulose filters were hybridized at low stringency with the radioactive sac800 fragment ($1.5 \times 10^7$ cpm to $3.0 \times 10^7$ cpm added to each bag with 4 or 6 round filters, the filters always being in pairs in one bag, i.e. filters A and B from the same plate). ZAP2, 3, 4, 5, 6 and 7 showed positive signals (one to many candidates) and they were serially diluted from this step (Step 2). Zap1, 8 and 9 had been too much diluted too much and showed no signals; they were therefore serially diluted again from the original isolate (step 1). An appropriate dilution, 200–500 plaques for ZAP2, 3, 4, 5, 6, and 7 and 1500–3000 plaques for ZAP 1, 8 and 9, was used to make replicas of A and B. The resulting nitrocellulose filters were hybridized with the radioactive Sac800 fragment as described above.

ZAP1 and ZAP8 showed positive signals at this point (step 2), but ZAP 9 showed not positive signals and was nor further investigated. It was possible to isolate a single positive plaque from the plates with ZAP2, 3, 4, 5, 6 and 7, and they were at this point ready for excision from the plasmid.

ZAP1 and ZAP8 were serially diluted (step 2) and an appropriate dilution from each was used to make replicas. ZAP2, 3, 4, 5, 6 and 7 were also diluted, plates with 20–50 plaques being used for replicas. This step (step 3) was performed as an extra control of these phages. All filters were hybridized with the radioactive Sac800 fragment at low stringency. ZAP1 and ZAP8 showed positive signals and it was possible to isolate a single positive plaque from each. ZAP1 gave a weaker signal throughout the isolation process than the others; Nevertheless, it was present throughout the entire process.

ZAP1 and ZAP8 were also plated for control hybridization of purity. All eight phages ZAP1–8 were pure, since all plaques on the plates hybridized. The plasmids from each of ZAP1 to ZAP8 were excised following the excision protocol under "Materials and Method".

A large number of ampicillin-resistant colonies were obtained and two colonies from each of ZAP1–8 were grown overnight for plasmid preparation. The plasmids were named AmyZ1 to AmyZ8. The colonies all contained plasmids. Plasmids AmyZ2-7 were digested with EcoRI and run on a 2% agarose gel with pBR327 digested with either BstNI or HinfI as size markers (FIG. 9). The gel also contained SacI digested pBS036 (FIG. 7). The gel was used for southern transfer as described in "Materials and Methods" and the nitrocellulose filter was hybridized at low stringency with the radioactive Sac800 fragment ($1 \times 10^6$ cpm added). All plasmids showed at least one positive fragment (FIG. 9), confirming that the correct cDNA-clones had been isolated. AmyZ2, 3, 4, 5, 6 and 7, and subsequently AmyZ1 and 8, have all been frozen in 25% sterile glycerol for prolonged storage (−80° C.).

EXAMPLE 6
Mapping of the α-amylase cDNA clones and DNA sequence analysis

AmyZ2, 3, 4, 5, 6 and 7 were digested with EcoRI and run on a 5% acrylamide gel, yielding the same fragments seen in FIG. 9. AmyZ1 and 7 were treated the same way and the resulting EcoRI fragments from all eight clones are illustrated in FIG. 10.

The EcoRI fragments as well as fragments obtained by digestion with other restriction enzymes were isolated and subcloned in the pBS-vector (see "Materials and Methods"). The fragments were cloned into the polylinker region situated between the sequence priming sites. The subclones were tested for correct insert size and frozen in 25% sterile glycerol for prolonged storage.

The strategy for sequencing the potato inserts of AmyZ3 and Z4 is shown in FIG. 11, the strategy for the inserts of AmyZ1 and AmyZ6 is shown in FIG. 12, and the strategy for sequencing AmyZ2 and AmyZ7 is shown in FIG. 13. EcoRI fragments from AmyZ5 and AmyZ8 were also sequenced and the results showed that these two clones are identical to AmyZ7.

The nucleotide sequences were analyzed with the aid of Beckman Micro-Genie Sequence Software, and the sequences of the potato inserts are shown in FIGS. 1–5 as follows: FIG. 1=AmyZ3/4, FIG. 2=AmyZ7, FIG. 3=AmyZ1, FIG. 4=AmyZ6 and FIG. 5=AmyZ2.

EXAMPLE 7

At least five α-amylase genes of two dissimilar types are active in potato sprout tissue The cDNA in AmyZ1–8 contains copies of α-amylase messenger RNAs from potato sprout tissue and are thus copies of products of potato α-amylase genes. The sequences shown in FIGS. 1–5 are all different and are therefore products of different genes. This shows that at least five different genes are active in potato sprouts from the variety Dianella. Pairwise comparisons of the five sequences from FIGS. 1–5 show that they fall into two groups as illustrated in the following table. The sequences were aligned and the table shows the percentage homology between pairs of sequences to the extent that they overlap. Gaps were introduced to optimize the alignments and the gaps were included in the total length for the calculation of the homoglogy.

| | % Nucleotide Sequence Homology | | | |
|---|---|---|---|---|
| | AmyZ1 | | | |
| AmyZ6 | 91,1 | AmyZ6 | | |
| AmyZ3/4 | 55,5 | 55,4 | AmyZ3/4 | |
| AmyZ7 | 55,5 | 55,4 | 98,9 | AmyZ7 |
| AmyZ2P | 60,1 | 59,2 | 98,5 | 99,2 |

It is seen that the sequences of AmyZ3/4, AmyZ7 and AmyZ2, including the 3' untranslated regions, are very homologous indeed. This finding suggests that the three corresponding genes are alleles of the same gene, which is possible because the potato variety used (as well as other commercial potato varieties) are tetraploid. In the following, the clones/sequences AmyZ3/4, AmyZ7 and AmyZ2 will be referred to as the AmyZ3/4 type. AmyZ1 and AmyZ6 are likewise very homologous, but in this case the homology is slightly lower and the differences between the genes are concentrated in 3' untranslated regions. AmyZ1 and AmyZ6 may be the products of alleles of one gene but they may also be different genes belonging to a sub-gene family. In the following, the clones/sequences AmyZ1 and AmyZ6 will be referred to as the AmyZ1 type. From the above table it can be seen that the homology between the nucleotide sequences of any of the AmyZ3/4 type and either of the AmyZ1 type is low, 55–60%, and the result shows that two distinctly different types of potato α-amylase cDNA clones have been isolated.

Nucleotide sequences are characterized by an additional parameter, the nucleotide composition. This parameter, usually expressed as the CG content, is particularly useful for discriminating between coding regions and non-coding regions. It has been found that coding regions have CC contents 15–20% higher than non-coding regions (Salinas, J., Matassi, G., Montero, L. M., and Bernardi, G. (1988), Compositional compartmentalization and compositional patters in the nuclear genomes of plants, Nucleic Acids Res. 16, pp. 4269–4285) and this information is helpful in locating introns and exons in genes. Moreover, the coding regions (and genomes) of different plant species have different CC contents and there is a relatively sharp division between monocotyledon plants and dicotyledon plants. The CC content of the coding regions of the potato α-amylase cDNAs is in all cases below 50% whereas the CG content of cereal α-amylase coding regions is above 50%. The examples indicate that α-amylase coding regions from other plants may be allocated to the monocotyledon or dicotyledon group of the angiosperms on the basis of the CC content.

EXAMPLE 8

Nucleotide sequence of potato α-amylase AmyZ3/4 messenger including leader, main coding region, and 3' untranslated region FIG. 1 shows the sequence of the messenger RNA-like strand of the combined inserts of potato α-amylase cDNA clones AmyZ3 and AmyZ4, and FIG. 11 gives a summary of the structure of the two clones. AmyZ3 and AmyZ4 have identical nucleotide sequences in the regions where they overlap (compare FIG. 11), except that AmyZ3 has an intron sequence of 128 nucleotides in the 5' leader sequence (sometimes called the 5' untranslated region). The intron terminates in consensus 5' and 3' splice junction nucleotides, GT and AG, respectively, and the intron contains a consensus branch point. Consensus splice junctions and branch points for plant introns have been compiled by Brown (32). The nucleotide sequence of the 3' leader up to nucleotide 540 contains four open reading frames shown in detail in FIG. 17. The region encoding the α-amylase precursor starts at nucleotide 541 and terminates at nucleotide 1761, and the derived length of the α-amylase precursor is 407 amino acids. The 3' untranslated region is at least 200 nucleotides in length, not including the polyA tail, but probably not much longer since a putative polyA signal is found 30 nucleotides from the end. PolyA signals are extremely well conserved in animals in which practically all genes have AATAAA about 20 base pairs from the polyadenylation site (33), but are quite degenerate in plants, although AT-rich (34).

EXAMPLE 9

Special features of the nucleotide sequences of the potato α-amylase AmyZ3/4 messenger RNA FIG. 11 illustrates the unusual structure of the potato α-amylase AmyZ3/4 messengers: they have very long 5' leader regions containing open reading frames (FIG. 17). In addition, two different types of transcripts from the same gene have been isolated in the AmyZ3 and AmyZ4 clones, one containing an intron in the leader region. Normally, unspliced transcripts constitute a very minor fraction of PolyA RNA, and the fact that an unspliced transcript has been isolated (in a cDNA clone) indicates that they are fairly abundant and may have a specific function. In other systems such introns have been found to have a stabilizing effect on the messenger (Callis, J., Fromm, M. and Walbot, V. (1987), Genes and Development 1, pp. 1183–1200; Huang, M. T. F. and Gorman, C. M. (1990); Nucleic Acids Res. 18, pp. 937–94). The amount of protein produced from the messenger may thus be regulated by the degree to which the leader intron is spliced out. Long leaders with open reading frames have also recently been found in Pea phytochrome transcripts (47). It is not known whether the reading frames in the potato α-amylase or the pea phytochrome 5' leaders are actually translated in the plants. This might be tested by raising antibodies against artificial peptides having the sequences shown in FIG. 17 and reacting such antibodies with plant cell extracts.

EXAMPLE 10

The nucleotide sequences of potato α-amylase AmyZ7 and AmyZ2 messengers

FIG. 2 shows the nucleotide sequence of the messenger RNA-like strand of the insert of potato α-amylase cDNA clone AmyZ7. The sequence is very homologous to the sequence of AmyZ3/4, but the clone is shorter in the 5' end and the first nucleotide in FIG. 2 aligns with nucleotide 543 in FIG. 1, which is the third nucleotide of the initiation codon. The alignment continues without gaps beyond the translation stop codon, and the α-amylase precursor encoded by AmyZ7 is 407 amino acids long as for AmyZ3/4. The 3' untranslated region is 187 nucleotides long followed by a polyA tail nine residues long.

FIG. 5 shows the nucleotide sequence of the messenger RNA-like strand of the insert of potato α-amylase cDNA clone AmyZ2. The sequence is denoted AmyZ2P to indicate that a string of 76 T residues erroneously inserted during the cloning in the 5' end is not included in FIG. 5. The sequence is very homologous to the sequence of AmyZ3/4, but the clone is shorter both in the 5' and 3' end. The first nucleotide in FIG. 5 aligns with nucleotide 1023 in FIG. 1, and the last nucleotide in FIG. 5 aligns with nucleotide 1756 in FIG. 1, unexpectedly, the alignment requires that two gaps are introduced into the AmyZ2 sequence (shown as blank spaces in FIG. 5). It follows that the α-amylase open reading frame is interrupted and AmyZ2 does not encode a partial potato α-amylase. AmyZ2 has two deletions relative to AmyZ3/4; one deletion could have been ascribed to a mistake made by the enzymes during the synthesis of the double-stranded cDNA in the cloning process, but two such mistakes in one clone is very unlikely and it may be concluded that the gene corresponding to AmyZ2 has suffered at least two deletions in the coding region. In other words, the AmyZ2 has undergone fatal mutations and has become a pseudo-gene.

During further evolution such genes suffer more mutations, against which there is no selection, and in time, the gene will also lose the ability to be transcribed. Thus, it is relatively rare that pseudo-genes are active. Although AmyZ2 no longer encodes a partial potato α-amylase, its isolation contributes to the elucidation of the structure of potato α-amylase genes and gene families and it can be employed in hybridization studies in the same way as AmyZ3/4 and AmyZ7 or fragments thereof.

EXAMPLE 11
Nucleotide sequences of potato α-amylase AmyZ1 and AmyZ6 messengers

FIG. 3 shows the sequence of the messenger RNA-like strand of potato α-amylase cDNA clone AmyZ1. The sequence is significantly different from the AmyZ3/4 type (Example 7), but the first nucleotide in FIG. 3 aligns approximately with nucleotide 740 in FIG. 1. The first codon in frame with the α-amylase reading frame is a stop codon, but this stop codon is so close to the cloning site that it is ascribed to a cloning error and it is not likely that AmyZ1 is the product of a pseudo-gene as described for AmyZ2 in Example 10. The α-amylase open reading frame is 350 codons long and the sequence terminates with a 163 nucleotides long 3' untranslated region that does not have a polyA tail.

FIG. 4 shows the sequence of the messenger RNA-like strand of potato α-amylase cDNA clone AmyZ6. It is 91% homologous to the sequence of AmyZ1, but half of the nucleotide differences between AmyZ1 and AmyZ6 are concentrated in the region downstream from the stop docon in AmyZ1. AmyZ6 is shorter than AmyZ1 in the 5' end; nucleotide 1 in FIG. 4 aligns with nucleotide 201 in FIG. 3. AmyZ6 has a one nucleotide deletion corresponding to position 816 in FIG. 3 with the result that the AmyZ6 α-amylase open reading frame is 66 codons shorter than the AmyZ1 open reading frame in the 3' end. This finding is further discussed in Example 14. The AmyZ6 sequence terminates with a 360 nucleotides long 3' untranslated region and since AmyZ6 and AmyZ1 are very homologous, the first part of the 3' untranslated region in AmyZ6 corresponds to the region in AmyZ1 that encodes the terminal 66 amino acids.

EXAMPLE 12
Borderline homology between potato and barley α-amylase sequences

Having determined the nucleotide sequence of potato α-amylase cDNA clones, the actual homology was determined between the SacI fragment of the barley α-amylase probe (FIG. 7) with which the isolation of corresponding potato cDNA clones was accomplished. In FIG. 10, the EcoRI fragments from AmyZ clones that hybridize with the barley probe are indicated. In FIG. 14, the nucleotide sequence of the hybridizing EcoRI fragment from AmyZ4 is aligned with the corresponding sequence of the barley probe. It is seen that the homology is only 63.5%. However, within these sequences there is a shorter region, 146 nucleotides long with a homology of 73% that includes a core of 46 nucleotides with 80% homology. The same type of comparison was carried out between the ExoRI fragment from AmyZ6 that hybridizes to the barley probe (FIGS. 9 and FIG. 10). The overall homology is 66%, a shorter region of 110 nucleotides has 77% homology and a core of 62 nucleotides has 84% homology. Levels of homology of this magnitude have previously been determined to be just sufficient to allow detection of sequences in heterologous hybridizations at low stringency of hybridization (29 and 35). This analysis demonstrates the importance of the careful optimization of 1) the source of messenger used for the potato cDNA library, 2) the conditions of hybridization, and 3) the limitation of the length of the barley probe to the subfragment that includes the regions of sufficient homology for the isolation of the potato α-amylase clones.

EXAMPLE 13
Properties of the α-amylase precursor encoded by AmyZ3, AmyZ4 and AmyZ7

The nucleotide sequence shown in FIG. 1 contains one long open reading frame of 407 codons and the derived amino acid sequence is shown below the nucleotide sequence. To confirm the identity of the potato α-amylase clone, the derived amino acid sequence was compared with the sequence of the barley α-amylase derived from the sequence of pM/C (24) and the comparison is shown in FIG. 15. The percentage of identical amino acids is 45.6 and at 72 positions similar amino acids are found. This degree of similarity is significant, in spite of a number of gaps introduced to maximize the similarity, and indicates that the two sequences have a common evolutionary origin (36). The plasmids AmyZ3 and AmyZ4 are therefore potato α-amylase cDNA clones. Furthermore, the peptide indicated by a box in FIG. 15 is even conserved in α-amylases found in mammals and insects (see 55).

The nucleotide sequence shown in FIG. 2, which is 99.2% homologous to the sequence shown in FIG. 1 in the region where they overlap, like AmyZ3/4 encodes a 407 amino acids long peptide (except that the first two nucleotides of the initiation codon are lacking in AmyZ7). The sequences of the α-amylase precursors encoded by AmyZ3/4 and AmyZ7 differ at three residues and in each case similar amino acids are found: position 37 has leucine to isoleucine, position 333 has phenylalanine to tyrosine and position 385 has valine to methionine.

α-Amylase is synthesized as a precursor in barley and wheat with a so-called signal peptide in the N-terminal of the peptide. Signal peptides mediate the transport across membranes and have common properties which are partly conserved between prokaryotes and eukaryotes (37). They are 15 to 30 amino acids long and include a hydrophobic region near the middle. The residues before and just after the processing site have a distinct pattern used to predict the processing site in precursors in which it has not been determined experimentally (38). To illustrate the structure of the complete α-amylase precursor as well as of the signal peptide, a hydrophilicity profile was calculated for the peptide (FIG. 18). The figure shows the short hydrophobic region near the N-terminal of the precursor and the residues are indicated. The most likely processing site is indicated, the site being found using the rules proposed by von Heijne: the glycine at position −1 is most significant, but the arginine at position −3 is unusual. The hydrophobic region is short compared with other eukaryotic signal peptides, and short hydrophobic regions are more often found in prokaryotic signal peptides. It is concluded that the potato α-amylase precursor starts with a signal peptide and that the probable processing site is after glycine 18. However, the structure of the signal peptide is atypical and may signify a special transport mechanism. The final location of the mature enzyme is not known precisely in potato sprouts or in cereals.

The hydrophilicity profile of the mature α-amylase (FIG. 18) does not show pronounced hydrophobic or hydrophilic regions and the analysis predicts that the enzyme is soluble.

The amino acid composition of the mature α-amylase encoded by AmyZ3 and AmyZ4 is compared with the composition of the two types of barley α-amylase in the following table:

α-AMYLASES: AMINO ACID COMPOSITION (%)

| Amino Acid | Potato | Barley A (low pI) (Amy2) | Barley B (high pI) (Amy1) |
|---|---|---|---|
| Ala | 6.7 | 11.4 | 8.7 |
| Arg | 4.9 | 3.6 | 4.5 |
| Asn | 4.6 | 4.1 | 4.0 |
| Asp | 6.9 | 8.9 | 9.2 |
| Cys | 0.8 | 1.0 | 0.7 |
| Gln | 4.1 | 2.9 | 3.2 |
| Glu | 4.1 | 3.1 | 4.0 |
| Gly | 8.2 | 10.6 | 10.9 |
| His | 3.9 | 2.9 | 4.0 |
| Ile | 6.4 | 5.6 | 6.2 |
| Leu | 6.4 | 6.0 | 7.2 |
| Lys | 6.2 | 5.3 | 5.9 |
| Met | 1.8 | 2.9 | 1.5 |
| Phe | 4.4 | 3.6 | 4.0 |
| Pro | 4.4 | 4.1 | 4.7 |
| Ser | 7.5 | 5.1 | 3.2 |
| Thr | 5.1 | 4.1 | 4.2 |
| Trp | 4.1 | 3.9 | 4.0 |
| Tyr | 4.4 | 3.9 | 3.7 |
| Val | 5.1 | 6.8 | 6.2 |
| Mw | 44397 | 45288 | 45083 |
| Acidic (D,E) | 11.1 | 12.1 | 13.1 |
| Basic (R,K) | 11.1 | 8.9 | 10.4 |
| Aromatic (F,W,Y) | 12.9 | 11.4 | 11.6 |
| Hydrophobic (F,W,Y,I,L,M,V) | 32.6 | 32.6 | 32.7 |
| Net charge at pH 7.0 | 0 | −13 | −11 |

The barley (and wheat) amylases are acidic (pIs 4.9–6.0) and acidic to neutral (pIs 6.3–7.5). In the newer nomenclature, the higher pI types are preferably called Amy1 and the lower pI types are called Amy2. The potato α-amylase type AmyZ3/4 is neutral, and as described in Example 15, the sequence is equally different from the cereal type 1 and type 2 sequences.

The amino acid sequences are in all cases deduced from nucleotide sequences. The N-terminal amino acid of the mature peptides have been determined in the case of barley amylase A, and is deduced from the structure of the precursor peptides in the two other cases.

EXAMPLE 14

Properties of the partial α-amylase encoded by AmyZ1 and AmyZ6

The low nucleotide sequence homology between the potato AmyZ3/4 type and the AmyZ1 type (55–60%, Example 7) suggests that they encode distinctly different α-amylases. This is indeed the case: the amino acid sequence homology between the AmyZ3/4 α-amylase and the partial AmyZ1 α-amylase is only 45.9%. α-Amylase has been purified from potato (Fan, M. L., Taiwania 1975, 20, pp. 71–76), but it is not possible to deduce if the preparation was a mixture of the AmyZ3/4 types and the AmyZ1 types or only contained one type (which again presumably would be a mixture of the closely related α-amylases found for each type and represented in FIGS. 1–2 and FIGS. 3–4, respectively).

As shown in FIGS. 3 and 4 and described in Example 11, the AmyZ6 α-amylase is 66 amino acids shorter in the C-terminal end than the AmyZ1 α-amylase. Variable lengths of the C-terminal region have also been found for barley α-amylases (Huang, J.-K., Swegle, M., Dandekar, A. M., and Muthukrishnan, S. (1984), Plant Mol. Biol. 9, pp. 3–17). This indicates that the C-terminal portion is not important for the catalytic function of the enzyme, but the variations in length may well influence other properties of the enzymes, such as specific activity, temperature dependency and pH optimum.

FIG. 16 shows a comparison of the amino acid sequences decoded from barley α-amylase clone pM/C and potato α-amylase clone Amy21. The numbering of the amino acids refers to the barley α-amylase precursor. Despite the finding that the local nucleotide sequence homology between the pM/C sequence and the Amy23/4 and Amy Z1 type sequences, respectively, are not significantly different (Example 12), the amino acid sequence homology between the barley pM/C α-amylase and the potato AmyZ1 α-amylase is 64.1% and thus significantly greater than between the barley α-amylase and the potato AmyZ3/4 type α-amylases (45.6%, FIG. 15). However, like AmyZ3/4 α-amylase, the AmyZ1 α-amylase is preferably not homologous with one of the types of cereal α-amylases (Example 15).

About 87% of the complete mature amino acid sequence of potato α-amylase type AmyZ1 is shown in FIG. 3, and a comparison of this peptide with the corresponding peptide in AmyZ3/4 α-amylase indicates that the AmyZ1 type α-amylase is more acidic than the AmyZ3/4 α-amylase but less acidic than the two barley α-amylases listed in the table in Example 13. Thus, the charge of the partial α-amylase shown in FIG. 3 is approximately −6 at pH 7.

EXAMPLE 15

A survey of cereal α-amylase gene sequences and comparisons of the deduced amino acid sequences and their relationship to the potato α-amylases In the following table, the plant α-amylase gene/cDNA sequences found in the GenBank and EMBL sequence databases are listed with their types as far as deduced, the database identifications, the clone napes, and the literature references.

| Type  | Name                    | Clone          | Reference |
|-------|-------------------------|----------------|-----------|
| Amy1  | BLYAMY1 (HVAMY1)        | amy1           | Knox, C.A.P., Sonthayanon, B., Chandra, G. R. and Muthukrishnan, S. (1987) Plant Mol. Biol. 9, 3–17. |
|       | BLYAMY1A (HVAMY1A)      | p 141.117      | Knox, C.A.P., Sonthayanon, B., Chandra, G. R. and Muthukrishnan, S. (1987) Plant Mol. Biol. 9, 3–17. Muthukrishnan, S. (1988) Unpublished. |
|       | BLYAMYABE (HVAMYABE)    | pHV19          | Chandler, P. M., Zwar, J. A., Jacobsen. J. V., Higgins, T. J. V. and Inglis, A. S. (1984) Plant mol. Biol. 3, 407–418. |
|       | BLYAMYABD (HVAMYABD)    | pM/C           | Rogers, J. C. (1985) J. Biol. Chem. 260, 3731–3738 |
|       | BLYAMYABA (HVAMYABA)    | 103            | Huang. J. K., Swegle. M., Dandekar, A. M. and Muthukrishnan, S. (1984) J. Mol. Appl. Genet 2, 579–588. |
|       | BLYAMYABB (HVAMYABA)    | 168            | |
|       | BLYAMYABC (HVAMYABC)    | 96             | |
| Amy2  | BLYAMY2 (HVAMY2)        | amy2           | Knox, C.A.P., Sonthayanon, B., Chandra, G. R. and Muthukrishnan, S. (1987) Plant Mol, Biol. 9, 3–17. |
|       | BLYAMYG (HVAMYG)        | Lambda.amy32b  | Rogers. J. C. and Milliman, C. (1984) J. Biol. Chem. 259. 12234–12240, Whittier, R. F., Dean, D. A. and Rogers, J. C. Nucl. Acid Res (1987). |
|       | BLYAMYAA (HVAMYA)       | E              | Rogers, J. C. and Milliman, C. (1983) J. Biol. Chem. 258, 8169–8174. |
|       | BLYAMY2A (HVAMY2A)      | p 155.3        | Knox, C. A. P., Sonthayanan. B., Chandra, G. R. and Muthukrishnan, S. (1987) Plant Mol. Biol. 9, 3–17. |
| Amy1  | M24286                  | M24286         | O'Neill, S. D., Kumagai, M. H., Majumdar, A., Huang, N., Sutliff T. D. Rodriguez, R. L. (1989) unpublished. |
| Amy3? | (OSAMYA)                | M24941         | Sutliff, T. D., Huang. N., Rodriguez, R. L. (1989) unpublished. |
| ?     | (OSAAMYB)               | pOS137         | O'Neill, S. D., Kumagai. M. H., Majumdar, A., Huang, N., Sutliff, T. D. Rodriguez. R. L., (1989) unpublished. |
| Amy1  |                         | Amy1/13        | |
| Amy2  |                         | Amy2/54        | Baulcombe, D. C., Huttly, A. K., Martienssen, R. A., Barker, R. F. and Jarvis, M. G. (1987) Mol. Gen. Genet 209, 33–40. |
| Amy3  | WHTAMYA (TAMY3 or TAAMYA) | lambda.amy3/33 | |

The name is the one given the clone in the database: Gen Bank. compiled by the National Institues of Health. The The name in parentheses is the one given the clone in the database: EMBL. compiled by the European Molecular Biology laboratory. The first 11 clones has been isolated from barley (*Hordeum vulgare*), the next 3 are isolated from rice (*Oryza saliva*) and the last 3 has been isolated from wheat (*Triticum sestivum*).

The table shows that a number of α-amylase gene sequences have been determined in barley, wheat and rice. The cereals are, like all grasses, monocotyledon plants, whereas potato is a dictyledon plant—no α-amylase gene sequences from dicotyledon plants were in the databases.

All nucleotide sequences listed in the table were decoded and paired homologies of all α-amylase amino acid sequences were calculated. The amino acid sequences of the potato α-amylase shown in FIGS. 1–4 were similarly compared to each other and to all the cereal amino acid sequences. The result is shown in the following table.

| | % AMINO ACID HOMOLOGY | | | | |
|---|---|---|---|---|---|
| | BARLEY → BLYAMY1 | | | | |
| BLYAMY1A  | 91.6 | BLYAMY1A | | | |
| BLYAMYABE | 98.4 | 92.7 | BLYAMYABE | | |
| BLYAMYABD | 99.8 | 91.4 | 98.6 | BLYAMYABD | |
| BLYAMY2   | 72.8 | 70.8 | 75.6 | 73.0 | BLYAMY2 |
| BLYAMYG   | 72.8 | 70.1 | 76.1 | 73.0 | 96.4 |
| BLYAMYAA  | 73.0 | 71.0 | 75.9 | 73.2 | 99.8 |
| BLYAMY2A  | 69.7 | 62.2 | 73.4 | 69.9 | 87.9 |
| M24286    | 81.8 | 80.5 | 85.0 | 82.1 | 74.6 |
| OSAMYA    | 70.0 | 68.6 | 72.5 | 70.3 | 67.8 |
| OSAMYB    | 69.1 | 68.1 | 72.2 | 69.4 | 67.2 |
| Amy1/13   | 93.0 | 92.8 | 94.5 | 93.2 | 73.4 |
| Amy2/54   | 72.2 | 70.3 | 75.3 | 72.5 | 94.3 |
| WHTAMYA   | 62.3 | 63.3 | 67.8 | 66.0 | 62.6 |
| AmyZ1     | 64.1 | 62.2 | 68.1 | 64.1 | 63.3 |
| AmyZ6     | 67.1 | 65.1 | 68.6 | 67.1 | 67.8 |
| AmyZ3/4   | 45.9 | 45.1 | 47.2 | 46.2 | 44.3 |
| AmyZ7     | 45.9 | 45.1 | 47.5 | 46.2 | 44.3 |
| | RICE → M24286 | | | | |
| OSAMYA    | 70.3 | OSAMYA | | | |
| OSAMYB    | 67.8 | 75.8 | OSAAMYB | WHEAT → | |

| % AMINO ACID HOMOLOGY | | | | | |
|---|---|---|---|---|---|
| Amy1/13 | 82.7 | 69.8 | 69.7 | Amy1/13 | |
| Amy2/54 | 73.5 | 67.5 | 66.4 | 72.5 | Amy2/54 |
| WHTAMYA | 69.5 | 72.1 | 66.8 | 64.8 | 64.2 |
| AmyZ1 | 61.6 | 62.7 | 61.0 | 64.4 | 62.8 |
| AmyZ6 | 64.1 | 68.3 | 68.3 | 67.1 | 67.8 |
| AmyZ3.4 | 45.0 | 43.3 | 42.7 | 46.2 | 44.6 |
| AmyZ7 | 45.0 | 43.3 | 42.7 | 46.2 | 44.6 |

| | | | | |
|---|---|---|---|---|
| BLYAMY1A | | | | |
| BLYAMYABE | | | | |
| BLYAMYABD | | | | |
| BLYAMY2 | | | | |
| BLYAMYG | BLYAMYG | | | |
| BLYAMYAA | 96.7 | BLYAMYAA | | |
| BLYAMY2A | 87.6 | 88.1 | BLYAMY2A | |
| M24286 | 66.9 | 74.8 | 70.6 | |
| OSAMYA | 66.9 | 67.8 | 63.3 | |
| OSAMYB | 64.2 | 67.4 | 63.6 | |
| Amy1/13 | 73.3 | 73.6 | 69.3 | |
| Amy2/54 | 93.3 | 94.5 | 84.9 | |
| WHTAMYA | 63.0 | 64.0 | 60.4 | |
| AmyZ1 | 62.7 | 63.3 | 59.9 | |
| AmyZ6 | 67.3 | 67.8 | 61.5 | |
| AmyZ3/4 | 45.7 | 44.3 | 41.5 | |
| AmyZ7 | 45.7 | 44.3 | 41.5 | |
| OSAMYA | | | | |
| OSAMYB | | | | |
| Amy1/13 | | | | |
| Amy2/54 | | | | |
| WHTAMYA | WHTAMYA | | POTATO → | |
| AmyZ1 | 56.0 | AmyZ1 | | |
| AmyZ6 | 59.5 | 91.7 | AmyZ6 | |
| AmyZ3.4 | 43.6 | 45.9 | 56.6 | AmyZ3 4 |
| AmyZ7 | 43.9 | 45.9 | 57.1 | 99.3 |

Among the many observations that can be made from the homology matrix, the following are particularly relevant for the potato α-amylases. Barley and wheat are closely related and in the table the figures in bold face show that barley and wheat have closely related sub-gene families that code for Amylase type 1 and type 2, respectively. In wheat a third type of 3-amylase, Amylase type 3, has been found that has not yet been found in barley. Rice is more distantly related to barley and wheat than they are to each other and the assignment of the rice α-amylase to the three types of wheat α-amylases is less clearcut. Potato is very distantly related to wither the cereal plants and it is observed that the homology of each of the potato sequences is approximately the same to all the cereal sequences, and the potato α-amylases cannot on the basis of amino acid comparisons be categorized as belonging to any of the three cereal types of amylases. On the other hand, it is striking that the potato AmyZ1 type α-amylases are more homologous to the cereal α-amylases than to the potato Amy23/4 type α-amylases.

EXAMPLE 16

Arrangement of α-amylase genes in potato

DNA from potato was analyzed by Southern hybridizations (15) and two sets of experiments were carried out. In the first experiment (FIG. 19), separate EcoRI fragments from AmyZ3 were hybridized to DNA from potato variety Saturna and in this experiment the alleles/genes belonging to the AmyZ3/4 type of sequences were investigated. In the second experiment (FIG. 20), DNA from two potato varieties were hybridized separately with complete inserts from AmyZ3/4 and AmyZ1 type sequences. This experiment demonstrates that the two types of sequences do not cross hybridize at normal hybridization stringency due to the low sequence homology between the two types of sequences. In addition, the second experiment demonstrates DNA fragment polymorphisms of the α-amylase genes in different potato varieties.

In FIG. 19, DNA from potato variety Saturna was digested with EcoRI, HindIII, and BamHI, fractionated on agarose gels and the fragments transferred to nitrocellulose filters. One filter was hybridized to labelled EcoRI fragments No. 2, 3, and 4 from AmyZ3 (compare FIG. 10) and another, identical filter was hybridized to EcoRI fragment No. 1. The EcoRI patterns show four strong bands (approximately 6.0, 4.0, 2.2 and 1.5 kb) and six weaker bands (approximately 7.7, 6.8, 4.5, 3.1, 2.8, 2.5, and 1.0 kb) with probes 2, 3, and 4. Some of the bands also hybridize with probe 1, and two additional bands can be seen (1.7 and 1.2 kb). The HindIII patterns show three strong bands (approximately 15, 7.0 and 1.4 kb) and three weaker bands (5.4, 4.4, 1.8 kb) with probes 2, 3 and 4. The 1.8 kb and especially the 1.4 kb bands are very prominent with probe 1 and these fragments contain the part of the AmyZ3/4 type genes that harbors the start of the α-amylase open reading frame. In FIG. 20, DNA from potato varieties Saturna and Dianella was digested with ExoRI, HindIII, or BamHI, and two identidal filters were prepared as described above. One filter was hybridized to a labelled complete insert from AmyZ3 and the other filter was hybridized to a labelled complete insert from AmyZ6. The fragments hybridizing to Saturna DNA with AmyZ3 sequences are seen to be the same in FIG. 19 and FIG. 20, except that the weaker bands in FIG. 19 are not clearly seen in FIG. 20. When the DNA fragment pattern obtained with the AmyZ3 probe in FIG. 20 is compared in Saturna and Dianella DNA, som bands are seen to be the same, but sometimes with altered relative intensity, whereas other bands are not seen in one of the DNAs. One example is the absence of the 15 kb HindIII fragment in Dianella DNA, which instead has a stronger, clearly double 7.0 kb fragment. This type of DNA fragment polymorphism can be explored in RFLP mapping as described in Example 27.

For the AmyZ3/4 type amylase sequences in variety Dianella, the isolation of three different, but highly homologous cDNA clones suggested that these three sequences were derived from three alleles of the same α-amylase gene. The very simple fragment pattern seen in FIGS. 19 and 20 combined with the knowledge that the AmyZ3/4 type sequences contain both EcoRI and HindIII sites suggests that potato only has one α-amylase gene of the AmyZ3/4 type, but up to four different alleles may be present in one variety. However, the limitations of Southern analyses must be taken into account—both very large and small DNA fragments may escape detection.

In FIG. 20, Saturna and Dianella DNA was hybridized with complete inserts from AmyZ3 and AmyZ6. It is seen that the DNA fragment patterns are completely different for the two different types of α-amylase sequences, showing that they do not cross hybridize, as is expected from the low sequence homology between the two types of genes. As described in Example 7, AmyZ1 and AmyZ6 may be the products of alleles of one gene, but they may also be different genes belonging to a sub-gene family. The fragment pattern seen with the AmyZ6 probe is more complex than the pattern seen with the AmyZ3 probe, which may indicate that there is more than one AmyZ1 type gene in potato, and the Southern analysis therefore does not rule out that AmyZ1 and AmyZ6 represent two genes (with the possibility of up to eight different alleles). As with the AmyZ3 probe, the fragment patterns are seen to be different in the two varieties of potato also with the Amy26 probe. Thus, both types of α-amylase sequences can be employed in RFLP mapping.

EXAMPLE 17

α-amylase messenger RNA in potato sprouts and tubers

Saturna Sprout RNA was hybridized in two different experiments with AmyZ3 EcoRI fragment No. 1 and EcoRI fragments Nos. 2+3+4 (see FIG. 10). In both experiments a band of 1500 nucleotides was detected. The other RNA samples were hybridized with AmyZ3 EcoRI fragments Nos. 2+3+4. The result of the hybridizations is shown in FIG. 21 and the sizes of the transcripts detected are given in the following table.

| Potato variety | Tissue | Transcript size, nucleotides ± 100 |
|---|---|---|
| Dianella | Sprout | 1950 |
| Saturna | Sprout | 1500 |
| Dianella | Tuber | (1950) |
| Saturna | Tuber | 1700 and 2400 |

The transcript size estimates are approximate, but the differences in the transcript sizes are clear. In addition, the one band seen in Dianella sprout RNA is known to contain at least three types of α-amylase transcripts: nature messenger and a precursor with an intron 128 nucleotides long, corresponding to AmyZ3 and AmyZ4 (FIG. 11), and a messenger corresponding to AmyZ2 (FIG. 12).

The tuber RNAs were isolated from tubers stored at 8° C. for 19 weeks. α-Amylase transcripts were detected in both Saturna and Dianella, but the Dianella RNA quality was sub-optimal, and it is possible that Dianella tubers also contain large transcripts in addition to mature size α-amylase messenger.

The hybridization was performed under stringent conditions and therefore only α-amylase sequences of the AmyZ3/4 type were detected, but from the cloning results it is known that at least two transcripts of the AmyZ1 type are present in Dianella sprouts. The large transcript in Saturna tuber RNA is likely to be an abundant unspliced α-amylase transcript precursor and the presence of this transcript suggests that control of α-amylase gene expression in part may be controlled at the level of RNA maturation.

EXAMPLE 18

Isolation of additional potato α-amylase cDNA clones and potato α-amylase genes

Two very different types of α-amylase cDNA clones have been isolated from potato with a barley α-amylase probe using particular low stringency hybridization conditions. The AmyZ3/4 type clones (AmyZ2,3,4,5, and 7) or parts thereof on the other hand and the AmyZ1 type clones (AmyZ1 and 6) or parts thereof on the other hand now allow the isolation of all of the two types of potato α-amylase sequences, either genes, pseudo-genes, or messengers (including cDNAs) using standard methods (12). Standard conditions implies reasonable high stringency of hybridization (e.g. hybridization at 67° in 2×SSC, final wash at 67° C. in 1×SSC), which lowers the hybridization background and occurence of false signals and therefore greatly facilitates the isolation of additional α-amylase sequences.

EXAMPLE 19

Isolation of α-amylase genes and cDNA clones from other dicotyledon plants

The nucleotide sequence homology between the potato α-amylase cDNA clones type AmyZ3/4 and type AmyZ1 and any other α-amylase genes or messengers from a dicotyledon plant, in particular from the Solanaceae family, is better than between such dicotyledon α-amylase coding sequences and the barley (monocotyledon) α-amylase probe.

α-Amylase genes and cDNA clones from dicotyledon plants other than potato are therefore isolated with AmyZ3/4 type or AmyZ1 type sequences, or parts thereof as a probe under hybridization conditions identical to or more stringent than those described above for the isolation of the AmyZ series of clones with the barley α-amylase probe.

EXAMPLE 20

Levels of reducing sugars in four potato varieties stored at 8° C.

A series of biochemical studies was carried out to characterize potato varieties with respect to reducing sugar levels in stored potatoes (this example), the effect of cold induction (Example 21), and activities of α-amylase (Example 22). The results constitute the basis for methods for increasing or decreasing reducing sugar levels in potatoes, employing α-amylase gene constructs in transgenic potato varieties. Reducing sugar levels were determined in potatoes from the time they are taken from the field and during the winter storage period in the four potato varieties described in "Materials and Methods". The results for potatoes stored at 8° C. are shown in FIG. 22. The curves illustrate the substantial differences in reducing sugar levels found in the different varieties. The varieties represent approximately the known spectrum of levels of reducing sugars in cultivated potato.

EXAMPLE 21

Reducing sugar levels at different storage temperatures

Potatoes stored for 19 weeks at 8° C. or at 6° C. or for 6 weeks at 4° C. were sampled on the same day and the levels of glucose and fructose were measured. The result (FIG. 23)

shows the so-called cold-induced sweetening of potatoes, a response which is a natural reaction to low temperatures. The comparison of the reducing sugar levels in four different varieties of potatoes shows that the relative increase in sugar level is highest in low-sugar varieties and lowest in the high-sugar variety, but the relationship between the sugar levels in the four varieties stays the same. This indicates that a method that decreases the intrinsic level of reducing sugars also will improve the storage characteristics at low temperatures.

EXAMPLE 22

Correlation between reducing sugar levels and α-amylase activity in stored potatoes In the experiment described in the preceding Example the α-amylase activity was determined (method 2) in four potato varieties after 19 weeks of storage at 6° C. or 8° C. As far as the present inventors are aware, these are the first successful measurements of α-amylase activity in stored potatoes (3, 62). The activities were similar at 6° C. and 8° C., and in FIG. 24 the average activity at the two temperatures is correlated with the reducing sugar levels at 8° C. The figure shows a good correlation between reducing sugar levels and α-amylase activity. This observation is the basis for methods of reducing and increasing the level of reducing sugars in stored potatoes by controlling the production of α-amylase.

EXAMPLE 23

Correlation between reducing sugar levels and α-amylase gene activity

To further substantiate the notion that α-amylase activity is genetically determined such that α-amylase activity is determined by the level of expression of the α-amylase genes, RNA samples prepared from the four potato varieties mentioned above are assayed by semiquantitative Northern hybridizations using inserts from the isolated potato α-amylase cDNA clones as probes. Relative transcript levels are determined by scanning of autoradiograms resulting from the Northern hybridizations (40).

EXAMPLE 24

A method for decreasing the α-amylase (reducing sugar) level in potatoes

A plasmid is constructed in *E. coli*, the plasmid containing the following elements in said order 1) a plant promoter, 2) the α-amylase insert from e.g. AmyZ4 in orientation opposite to the orientation shown from left to right in FIG. 7, 3) a plant transcription termination sequence, e.g. from the nopaline synthetase (NOS) gene as provided between multiple cloning sites on pCaMVCN (Pharmacia LKB Biotechnology). The promoter may be the CaMV promoter or the NOS promoter (gene cartridges, Pharmacia LKB Biotechnology) for strong and medium strong constitutive expression of the antisense strand of the α-amylase sequence. The promoter may also be from a potato polyubiquitin gene isolated using pKG3730 as a heterologous probe (see Example 3) for low constitutive expression of the antisense strand of the α-amylase sequence, or a potato α-amylase promoter which is specifically active in the same plant cells as the α-amylase gene from which the promoter is taken. These examples of promoters and terminators are illustrative, and other sequences can fulfil the same roles.

An antisense construction including the entire sequence of AmyZ4 was made using the pBSK vector sites SacI and EcoRV of the AmyZ4 clone. The potato fragment was cloned into the plasmid pEnhanced-Peter-Linker (pEPL, (63)), which was first digested with SacI and then with SmaI. The resultant plasmid is called p(anti-AmyZ4).

pEPL was constructed from pCaMVCN (64,65) in which the CAT gene was removed by a PstI digestion. A small linker (linker: PstI-BamHI-BalI-PstI) has been inserted into this plasmid PstI site, giving the plasmid called pLise (pL). pL was digested with HincII and BglII and the resultant fragment containing the 35S promoter and the NOS terminator was cloned into another pL plasmid digested with EcoRV and BglII. Both EcoRV and HincII are blunt ended sites. The resulting construct is called pEnhanced-Lise (pEL). pEL differs essentially from pCaMVCN in that it contains a variant 35S promoter with a tandem duplication of the 250 base pairs of the upstream sequence of the promoter. The variant 35S promoter has a transcriptional activity approximately ten times higher than the natural 35S promoter (66). pEL was digested with PstI and BglII, thereby removing the NOS terminator, and a CaMV terminator (DW2t) was inserted instead. The plant virus terminator functions more efficiently than the plant gene terminator (67). Finally, a linker (PstI-BamHI-SmaI-SacI-SalI-SphI) was inserted into the PstI site situated between the enhanced 35S promoter and the CaMV terminator. This plasmid is called pEPL.

An antisense construction was also made with AmyZ6 in which the potato clone was digested with SacI and EcoRV (as AmyZ4). The potato fragment was cloned into pEPL, first digested with SacI and then with SmaI. The resultant plasmid is called p(anti-AmyZ6). Both p(anti-AmyZ4) and p(anti-AmyZ6) were digested with HindIII in order to isolate the fragments containing the entire enhanced 35S promoter, the inserted AmyZ4 or AmyZ6 in the antisense direction and the CaMV terminator. It was necessary to make a partial digestion with p(antiAmyZ4) since the AmyZ4 potato insert contains a HindIII site. The isolated fragments were cloned into the HindIII site of the binary vector pBI121 (68, 69, 70). The HindIII site in pBI121 is situated between a kanamycin resistance gene and the β-Glucuronidase (GUS) gene. The antisense construction (anti-AmyZ4 or anti-AmyZ6), the kanamycin resistance gene and the GUS gene all have their own promoter and terminator. The constructed pBI121-anti-AmyZ4 (or-anti-AmyZ6) is isolated from *E. coli* and transformed into the *Agrobacterium tumefaciens* strain LBA4404 which contains the disarmed helper plasmid pAL4404 (71,72) by the triparental mating method (73). A *Solanum tuberosum* transformation model system has been made with the potato varieties Dianella and Saturna. A pBI121 plasmid containing a herbicide resistance marker gene was used to create the model system in these potato varieties. The pBI121 with the marker gene was mated with LBA4404 as described above, and the resultant *A. tumefaciens* strain was grown overnight in LB medium with 50 μg/ml kanamycin. The cells were centrifuged and resuspended in Murashige and Skoog medium (MS medium) before transformation (Murashige, T. and Skoog, F. (1962), *Physiol. Plant* 15, pp. 473–497). Potato tubers were peeled, washed briefly in distilled water and surface sterilized for 15 min. in a 10% solution of Na-hypochlorite with a few drops of "tween®20". The potatoes were then washed extensively in sterile distilled water, and immersed in MS medium. Cylindrical samples were taken from the tubers using a sterile cork borer, and these samples were sliced into 1–2 mm thin discs with a scalpel. The tuber discs were floated in 20 ml of MS medium containing Agrobacterium and completely wetted by gentle shaking. 20 min. later, the tuber dics were transferred to supplemented MS plates (supplemented MS medium contains in addition to the MS salts 1 mg/l thiamine HCL, 0.5 mg/l nicotinic acid and 0.5 mg/l pyridoxine HCL (the vitamins) and 3% sucrose, 5 μM zeatin riboside and 3 μM IAA aspartic acid, pH 5.9. The medium was solidified with 0.8% Difco agar) and after 48 hours, they were transferred to new plates supplemented with 500 μg/ml carbencillin (to eliminate Agrobacterium) and 100 μg/ml kanamycin for selection of transformed potato issue. The sealed plates were incubated at 25° C. under a day-night light cycle. The tuber discs were subcultured every 3 weeks onto fresh supplemented MS medium with 200 μg/ml carbencillin. Developing shoots were removed and planted in large test tubes with MS medium containing vitamins, 200 μg/ml carbencillin and 100 μg/ml kanamycin for induction of roots. The shoots were investigated for GUS expression (70) and a blue color indicated that the shoots have been transformed with the marker gene. This model system is used for carrying the anti-AmyZ4 construct or the anti-AmyZ6 construct into the genome of e.g. both Dianella and Saturna, by co-cultivation with the pBI21-anti-AmyZ4 or pBI121-anti-AmyZ6 in pAL4404 and following the method already described for the marker gene.

Successfully transformed potato plantlets express α-amylase anti-messenger from the inserted tripartite gene construction which inhibits the translation of α-amylase by base pairing with α-amylase messenger. The lower level of α-amylase will in turn limit the degradation of starch, thereby limiting the formation of reducing sugars. An even greater inhibition of translation of α-amylase is obtained using constructs containing both anti-AmyZ4 and anti-AmyZ6.

EXAMPLE 25

A method for increasing the α-amylase (reducing sugar) level in potatoes

A plasmid is constructed in *E. coli*, the plasmid containing the following elements in said order 1) a plant promoter, 2) a potato α-amylase gene isolated as described in Example 18 from which the promoter is removed up to the transcription initiation site±approximately 20 bp. The plant promoters used are the same as specified in Example 24. In addition, a patatin promoter can be used. Patatin genes are highly expressed in the parenchym tissue of tubers (44) (region D in FIG. 6).

AmyZ4 (the cDNA clone containing the full length copy of the α-amylase messenger-RNA) was digested with BamHI and SalI (these sites are situated in the pBSK polylinker) and the resultant potato fragment was cloned into the pEPL (described in Example 24) plasmid digested with the same enzymes. This construct, called p(senseAmyZ4) has the enhanced 35S promoter (described in Example 24) followed by the AmyZ4 insert in the sense direction and after this, the CaMV terminator (described in Example 24). The tripartite fragment just described was isolated by a partial HindIII digestion of p(sense-AmyZ4) and was then cloned into the unique HindIII site of pBI121 and then transferred into e.g. the Dianella potato genome by the method described in Example 24.

Successfully transformed plantlets express α-amylase messenger at a higher level than untransformed plants, thus producing more α-amylase than the parent plant. The increased level of α-amylase will in turn enhance the degradation of starch, thereby increasing the level of reducing sugars. Using a construction with a patatin promoter, the excess α-amylase will accumulate in the middle of the tubers, converting some of the starch to sugars, and will be available for starch degradation during the first heating step prior to fermenation.

EXAMPLE 26

Production of potato α-amylase in microorganisms

The complete open reading frame for potato α-amylase precursor is excised from AmyZ4 with HaeII and DraI. HaeII cuts between the initiation codon ATG and codon number 2, and the HaeII site is filled in and ligated to a filled-in NcoI site (yielding CCATG), restoring the initiation codon. NcoI single sites are commonly found in initiation codon of *E. coli* expression vectors (e.g. pKK233-2, Pharmacia LKB Biotechnology). DraI cuts 51 bp after the termination codon, directly yielding a blunt end. The NcoI site is also restored in the expression plasmid for easy transfer of the complete potato α-amylase precursor open reading frame to other expression vectors for *E. coli*, other prokaryotes or eukaryotes such as yeast. Since signal peptides have similar features in prokaryotes and eukaryotes (Example 13), the potato α-amylase precursor may be processed correctly in the new host to yield mature α-amylase. Alternatively, coding regions for other signal peptides are used to replace the region coding for the potato α-amylase signal peptide.

To produce the AmyZ1 type α-amylase, a full length cDNA clone is isolated as described in Example 18 and appropriate restriction enzymes are used to excise the open reading frame precisely for insertion into an expression vector as described above.

EXAMPLE 27

Dot blot quick screening of potato varieties in breeding programmes

Based on the observations that the reducing sugar content in stored potatoes is correlated with α-amylase activity (Example 22) and that the correlation extend to sprouts (Example 17) and therefore probably to leaves, potato varieties can be screened for their tendency to accumulated sugar in stored potatoes already at a stage when young plantlets have formed a few leaves. RNA extracted from 0.1 to 0.5 grams of leaf material is spotted on filters suitable for hybridization and hybridized with radioactively or biotin labeled α-amylase cDNA sequences. As a reference, hybridization with similarly labeled ubiquitin coding regions from any organism, e.g. barley, can be used since ubiquitin sequences are extremely well-conserved and the ubiquitin genes are constitutively expressed in different plant tissues (17). The results are compared with similar dot blots of potato varieties with known sugar characteristics (e.g. the four varieties described in "Materials and Methods"). Such a dot blot assay can be carried out on a large amount of breeding material and can lead to an early assessment of quality as regards sugar characteristics.

EXAMPLE 28

RFLP mapping with α-amylase gene sequences

Restriction fragment length polymorphisms are increasingly used to follow specific alleles of genes, so far primarily in humans, but also in plants (58). The results of genomic Southern hybridization of potato DNA with the isolated α-amylase sequences showed (FIGS. 19 and 20) that potato has few α-amylase genes and therefore yields a simple fragment pattern that makes polymorphisms easy to evaluate. Examples of polymorphisms are shown in FIG. 20. Polymorphisms in α-amylase sequence hybridizing fragment length as in corresponding studies with other probes, is used either to follow the α-amylase alleles themselves or as (linked or unlinked) markers in crosses involving other characteristics, e.g. pathogen resistance and morphological characteristics such as tuber colour.

EXAMPLE 29
Controlled expression of other enzymes

α-Amylase genes from potato are expressed in a developmental and tissue (cell) specific fashion as is the case with most other plant genes. α-Amylase gene expression is characteristic for genes encoding enzymes (as opposed to structural proteins or storage proteins). The level of expression is relatively low, on the order of 0.01% of the total messenger in sprouts being α-amylase messenger (Example 5). Using an α-amylase promoter fused to genes without promoters encoding enzymes not found in potato or enzymes made in potatoes in small, but suboptimal amounts or in cells other than the cells that produce α-amylase, the intermediate metabolism and the metabolism of e.g. phytohormones may be fine-tuned. The fusion construct may be inserted into an A. tumefaciens vector for the production of transgenenic plants as described in Example 24.

1. Nowak. J. (1977), Zeitschrift für Pflanzenphysiologie 81, 125–140.
2. Sowokinos, J. R., Lulai, E. C. & Knoper, J. A. (1985), Plant Physiology 78, 489–494.
3. Ross, H. A. & Davies, H. V. (1987), Potato Research 30, 675–678.
4. Randall et al. (1985), Science 230, 1350–1354.
5. Randall et al. (1988), Science 239, 487–491.
6. Merrifield, R. B. (1963), J. Am. Chem. Soc. 85, p. 2149.
7. Cornford. C. A. Black, M., Doussant, J. & Murdoch, K. M. (1987), J. Exp. Bot. 38, 277–285.
8. Kaplan, B. B., Bernstein, S. L. & Gioio, A. E. (1979), Biochem. J. 183, 181–184.
9. Stovgaard-Jensen, J., Marcker, K. A., Otten, L. & Schell, J. (1986), Nature 321, 669–674.
10. McMaster, G. K. & Carmichael, G. G. (1977), Proc. Natl. Acad. Sci. USA 74, 4835–4838.
11. Gene Screen Instruction Manual 1983, New England Nuclear.
12. Maniatis, T., Fritsch, E. F. & Sambrook J. (1982), Molecular Cloning: A Laboratory Manual, Cold Spring Harbor Laboratory, Cold Spring Harbor, New York.
13. Causing. K. (1981), Mol. Gen. Genet. 184, 265–271.
14. Peacock, A. C. & Dingman, C. W. (1968). Biochemistry 7, 668–674.
15. Southern, E. M. (1975), J. Mol. Biol. 98, 503–517.
16. Rigby, W. J. P., Dieckmann M., Rhodes, C. & Berg, P. (1977), J. Mol. Biol. 113, 237–251.
17. Gausing. K. & Barkardottier, R. (1986), Eur. J. Biochem. 158, 57–62.
18. Denhardt, D. (1986), Biochem. Biophys. Res. Commun. 23, 541–552.
19. Mandell, M. & Higa, A. (1970), A. J. Mol. Biol. 53, 159–162.
20. Hanahan, D. (1983), J. Mol. Biol. 166, 557–580.
21. Cloning Kit. Instruction Manual from Stratagene, 11099 North Torrey Pines Road, La Jolla, Calif. 92037, U.S.A.
22. Sequenase™, Step-by-Step Protocols for DNA Sequencing with Sequenase™, 3rd Edition, United States Biochemical Corporation, P.O. Box 22400, Cleveland, Ohio 44122.
23. The potato crop. The scientific basis for improvement. Edited by P. M. Harris. Wiley, New York, 1978.
24. Rogers, J. C. (1985), J. Biol. Chem. 260, 3731–3738.
25. Hopp & Woods (1981), Proc. Natl. Acad. Sci. 76, 3824.
26. Melton, D. A., et al. (1984), Nucleic Acids Res., 12, 7035–7056.
27. Rogers, J. C., Milliman, C. (1983), J. Biol. Chem. 258, 8169–8174.
28. Gausing & Barkardottir (1986), Eur. J. Biochem. 158, 57–62.
29. Nielsen & Gausing (1987), FEBS letters 225, 159–162.
30. Stratagene Cloning system, Custom library, 11099 North Torrey Pines Road, La Jolla, Calif. 92037.
31. Short, J. M., Fernandez, J. M., Sorge, J. A., and Huse, W. D. (1988), Nucleic Acids Res. 16, 7583–7600.
32. Brown (1986), Nucleic Acids Res. 14, 9549–9559.
33. Proudfoot & Brownlee (1976), Nature 263, 211–214.
34. Hunt et al. (1987), Plant Molecular Biology 8, 23–35.
35. Nielsen, P. S. (1987), Thesis, University of Aarhus.
36. Doolittle (1981), Science 214, 149–159.
37. Watson (1984), Nucleic Acids Res. 12, 5145–5164.
38. von Heijne (1983), Eur. J. Biochem. 133, 17–21.
39. Baulcombe et al. (1987), Mol Gen Genet 209, 33–40.
40. Barkardottir et al. (1987), Developmetal Genetics 8, 495–511
41. An et al. (1988), Plant Molecular Biology Manual A3, 1–19.
42. An et al. (1986), Plant Physiol. 81, 301–305.
43. Block et al. (1987), EMBO J. 6, 2513–2518.
44. Rocha-Sosa et al. (1989), EMBO J. 8, 23–29.
45. Kirsten Paludan Thesis (1980), University of Aarhus
46. Gough & Murray (1982), J. Mol. Biol., 162: 43–67.
47. Sato (1988), Plant Mol. Biol. 11, 697–710.
48. Yanisch-Perron, C., Vieira, J. Messing, J. (1985), Gene 33, 103–119.
49. Bullock, W. et al. (1987), Biotechniques 5, 376–380
50. Boyer (1969), J. Mol. Biol. 41, 459.
51. Soberon, Covarrubias, Bolivar (1980), Gene 9, 287.
52. Lowry et al. (1951), J. Biol. Chem 193, 265–275.
53. Gynheung An et al. (1988), Binary Vectors, Plant Molecular Biology Manual A3, 1–19.
54. Butcher D. N. et al. (1980), Tissue Culture Methods for Plant Pathologists, eds.; D. S. Ingrams and J. P. Helgeson, 203–208.
55. Poppo H. Boer and Donal A. Hickey (1986), The α-amylase gene in Drosophila melanogaster: nucleotide sequence, gene structure and expression motifs, Nucleic Acids Research 21, Vol. 14, pp. 8399–8411.
56. Tanksley, S. D. et al. (March 1989)., RFLP Mapping in Plant Breeding: New Tools for an Old Science, Bio/Technology, Vol. 7, pp. 257–264.
59. van der Krol, A. R., et al. (1988), Gene 72, 45–50.
60. Sheeny R. E. et al. (1988), Proc. Natl. Acad. Sci., USA, 8805–8809.
61. Smith C. J. S. et al. (25 Aug., 1988), Nature, Vol. 334, pp. 724–726.
62. Davies H. V. and Ross H. A. (1987), J. Plant Physiol. Vol. 126, pp. 387–396.
63. The plasmid pEPL was kindly provided by Peter Stougaard, BKL, DANISCO A/S, Denmark.
64. Fromm, M. et al. (1985), Proc. Natl. Acad. Sci., USA 82, p. 5824.
65. Fromm, M. et al., (1986), Nature, 319, p. 791.
66. Kay R., Chan, A., Daly, M. and McPheson, J. (1987), Science 236, pp. 1299–1302.
67. Hernandez, G., Cannon, F., and Cannon, M. (1989), Plant Cell Report 8, pp. 195–198.
68. CLONTECH Laboratories, Inc.
69. Bevan, M. W. (1984), Nucleic Acids Res., 12, pp. 8711–8721.
70. Jefferson, R. A. Kavanagh, T. A., and Bevan, M. W. (1987), The EMBO J., 6, pp. 3901–3907.
71. Hockema, A., Hirsch, R. R., Hooykaas, P. J. J., and Schilperoort, R. A. (1983), Nature, 303, pp. 179–180.
72. Ooms, G., Hooykaas, P. J. J., Van Veen, R. J. M., Van Beelen, P., Regensburg-Tvink, T. J. G., Schilperoort, R. A. (1982), Plasmid, 7, pp. 15–29.

73. Ditta et al. (1981), *Proc. Natl. Acad. Sci., USA* 77, pp. 7347–7351.

74. Sheerman, S. and Bevan, M. W. (1988), *Plant Cell Reports*, 7, pp. 13–16.

We claim:

1. An expression vector for producing antisense α-amylase RNA comprising:

(a) a promoter, (b) a DNA molecule encoding an antisense α-amylase RNA, wherein said DNA molecule comprises a nucleotide sequence that is complementary to:

(i) a nucleotide sequence selected from the group consisting of the nucleotide sequence shown in FIG. 1, the nucleotide sequence shown in FIG. 2, the nucleotide sequence shown in FIG. 3, the nucleotide sequence shown in FIG. 4 and the nucleotide sequence shown in FIG. 5, or (ii) a fragment of (i), wherein said fragment consists of at least 50 nucleotides, and (c) a transcription termination DNA sequence operably linked to said DNA molecule encoding an antisense α-amylase RNA, wherein said promoter is operably linked to said DNA molecule encoding an antisense α-amylase RNA.

2. The expression vector of claim 1, wherein the antisense α-amylase-encoding strand of said DNA molecule has a nucleotide sequence that is complementary to a fragment of the nucleotide sequence shown in FIG. 1, and wherein said nucleotide sequence is contained in the cDNA clone AmyZ3 deposited in *E. coli* K-12 as DSM 5275.

3. The expression vector of claim 1, wherein the antisense α-amylase-encoding strand of said DNA molecule has a nucleotide sequence that is complementary to a fragment of the nucleotide sequence shown in FIG. 1, and wherein said nucleotide sequence is contained in the cDNA clone AmyZ4 deposited in *E. coli* K-12 as DSM 5276.

4. The expression vector of claim 1, wherein the antisense α-amylase-encoding strand of said DNA molecule has a nucleotide sequence that is complementary to a fragment of the nucleotide sequence shown in FIG. 3, and wherein said nucleotide sequence is contained in the cDNA clone AmyZ1 deposited in *E. coli* K-12 as DSM 5882.

5. The expression vector of claim 1, wherein the antisense α-amylase-encoding strand of said DNA molecule has a nucleotide sequence that is complementary to a fragment of the nucleotide sequence shown in FIG. 4, and wherein said nucleotide sequence is contained in the cDNA clone AmyZ6 deposited in *E. coli* K-12 as DSM 5883.

6. The expression vector of claim 1, wherein the antisense α-amylase-encoding strand of said DNA molecule has a nucleotide sequence that is complementary to a fragment of the nucleotide sequence shown in FIG. 2, and wherein said nucleotide sequence is contained in the cDNA clone AmyZ7 deposited in *E. coli* K-12 as DSM 5884.

7. The expression vector of claim 1, wherein said promoter is functional in a plant.

8. The expression vector of claim 7, wherein said promoter is regulatable by at least one factor selected from the group consisting of a developmental, a chemical, a physical and a physiological factor.

9. The expression vector of claim 7, wherein said promoter is a constitutive promoter selected from the group consisting of a NOS promoter, an ubiquitin promoter and a plant virus promoter.

10. The expression vector of claim 7, wherein said promoter is selected from the group consisting of a plant α-amylase promoter and a patatin promoter.

11. A genetically modified plant comprising, in its genome, the expression vector of claim 1.

12. The genetically modified plant of claim 11, wherein said plant comprises cells having reduced α-amylase activity, compared with a corresponding non-modified plant.

13. The genetically modified plant of claim 11, wherein said promoter activates the transcription of said DNA molecule encoding an antisense α-amylase RNA at temperatures below about 8° C.

14. The genetically modified plant of either claim 11 or claim 13, wherein said DNA molecule encoding an antisense α-amylase RNA is expressed in the tissue or cell in which at least one α-amylase gene is expressed.

15. The genetically modified plant of claim 14, wherein said plant is a dicotyledonous plant.

16. The genetically modified plant of claim 15, wherein said plant is a member of the family Solanaceae.

17. A vector system comprising at least one expression vector that carries a DNA molecule encoding an antisense α-amylase RNA, wherein said vector system operates to introduce said DNA molecule encoding an antisense α-amylase RNA into the genome of a plant, and wherein the antisense α-amylase-encoding strand of said DNA molecule has a nucleotide sequence that is complementary to:

(i) a nucleotide sequence selected from the group consisting of the nucleotide sequence shown in FIG. 1, the nucleotide sequence shown in FIG. 2, the nucleotide sequence shown in FIG. 3, the nucleotide sequence shown in FIG. 4 and the nucleotide sequence shown in FIG. 5, or (ii) a fragment of (i), wherein said fragment consists of at least 50 nucleotides, and wherein expression of said vector system results in synthesis of antisense α-amylase RNA.

18. The vector system of claim 17, wherein said vector system is a binary vector system.

19. The vector system of claim 17, wherein said vector system comprises a virulence function capable of infecting said plant and at least one border part of a T-DNA sequence, and wherein said border part is located on the same expression vector as said DNA molecule encoding an antisense α-amylase RNA.

20. The vector system of claim 17, wherein said vector system comprises an *Agrobacterium tumefaciens* Ti or Ri plasmid or an *Agrobacterium rhizogenes* Ri plasmid.

21. A microorganism of the genus Agrobacterium capable of infecting a plant, wherein said microorganism comprises the vector system of any one of claims 17–20.

22. The microorganism of claim 21, wherein said microorganism is an *Agrobacterium tumefaciens* strain.

23. An expression vector for producing antisense α-amylase RNA comprising:

(a) a promoter, (b) a DNA molecule encoding an antisense α-amylase RNA consisting of at least 50 nucleotides, said DNA molecule hybridizing under high stringency conditions of hybridization in 2×SSC at 67° C. and final washing in 1×SSC at 67° C. to a DNA molecule having a nucleotide sequence selected from the group consisting of the nucleotide sequence shown in FIG. 1, the nucleotide sequence shown in FIG. 2, the nucleotide sequence shown in FIG. 3, the nucleotide sequence shown in FIG. 4 and the nucleotide sequence shown in FIG. 5, and (c) a transcription termination DNA sequence operably linked to said DNA molecule encoding an antisense α-amylase RNA, wherein said promoter is operably linked to said DNA molecule encoding an antisense α-amylase RNA.

24. A vector system comprising at least one expression vector, including at least one expression vector according to claim 23, wherein said vector system is capable of introducing DNA encoding an antisense α-amylase RNA into the genome of a plant.

25. A genetically modified plant comprising, in its genome, the expression vector of claim 23.

* * * * *

UNITED STATES PATENT AND TRADEMARK OFFICE
CERTIFICATE OF CORRECTION

PATENT NO. : 5,789,657
DATED : August 4, 1998
INVENTOR(S) : Kirsten GAUSING et al.

It is certified that error appears in the above-identified patent and that said Letters Patent is hereby corrected as shown below:

Please note that assignment information needs to be added as follows:

[73] Assignee: A/S DE DANSKE SPRITFABRIKKER
(DANISCO A/S), Copenhagen K, Denmark.

Signed and Sealed this

Fifth Day of October, 1999

Attest:

Q. TODD DICKINSON

*Attesting Officer*  Acting Commissioner of Patents and Trademarks